United States Patent
Myung et al.

(10) Patent No.: US 8,679,190 B2
(45) Date of Patent: Mar. 25, 2014

(54) HYDROGEL ARTHROPLASTY DEVICE

(75) Inventors: David Myung, Santa Clara, CA (US); Lampros Kourtis, San Francisco, CA (US); Laura Hartmann, Berlin (DE); Curtis W. Frank, Cupertino, CA (US); Stuart B. Goodman, Los Altos, CA (US); Dennis R. Carter, Stanford, CA (US)

(73) Assignees: The Board of Trustees of the Leland Stanford Junior University, Palo Alto, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/418,294

(22) Filed: Mar. 12, 2012

(65) Prior Publication Data

US 2012/0232657 A1 Sep. 13, 2012

Related U.S. Application Data

(63) Continuation of application No. 12/148,534, filed on Apr. 17, 2008, now abandoned, and a (Continued)

(51) Int. Cl.
*A61F 2/30* (2006.01)

(52) U.S. Cl.
USPC .................... 623/23.58; 623/23.6; 623/13.11; 623/18.11

(58) Field of Classification Search
USPC .......................................... 623/11.11–23.76
See application file for complete search history.

(56) References Cited

U.S. PATENT DOCUMENTS

| 3,030,327 A | 4/1962 | Hosch |
| 3,053,251 A | 9/1962 | Black et al. |

(Continued)

FOREIGN PATENT DOCUMENTS

| EP | 1779875 A1 | 5/2007 |
| GB | 2372707 A | 9/2002 |

(Continued)

OTHER PUBLICATIONS

Kim et al. Journal of Applied Polymer Science. vol. 92, Issue 3 pp. 1731-1736.*

(Continued)

*Primary Examiner* — Liam Heincer
*Assistant Examiner* — Michael A Salvitti
(74) *Attorney, Agent, or Firm* — Shay Glenn LLP

(57) ABSTRACT

An arthroplasty device is provided having an interpenetrating polymer network (IPN) hydrogel that is strain-hardened by swelling and adapted to be held in place in a joint by conforming to a bone geometry. The strain-hardened IPN hydrogel is based on two different networks: (1) a non-silicone network of preformed hydrophilic non-ionic telechelic macromonomers chemically cross-linked by polymerization of its end-groups, and (2) a non-silicone network of ionizable monomers. The second network was polymerized and chemically cross-linked in the presence of the first network and has formed physical cross-links with the first network. Within the IPN, the degree of chemical cross-linking in the second network is less than in the first network. An aqueous salt solution (neutral pH) is used to ionize and swell the second network. The swelling of the second network is constrained by the first network resulting in an increase in effective physical cross-links within the IPN.

11 Claims, 29 Drawing Sheets

Related U.S. Application Data continuation-in-part of application No. 12/070,336, filed on Feb. 15, 2008, and a continuation-in-part of application No. 11/243,952, filed on Oct. 4, 2005, now Pat. No. 7,857,849, said application No. 12/070,336 is a continuation-in-part of application No. 11/636,114, filed on Dec. 7, 2006, now Pat. No. 7,857,447, and a continuation-in-part of application No. 11/409,218, filed on Apr. 20, 2006, now abandoned, and a continuation-in-part of application No. 11/639,049, filed on Dec. 13, 2006, now Pat. No. 7,909,867.

(60) Provisional application No. 60/923,988, filed on Apr. 17, 2007, provisional application No. 60/901,805, filed on Feb. 16, 2007, provisional application No. 60/616,262, filed on Oct. 5, 2004, provisional application No. 60/673,172, filed on Apr. 20, 2005, provisional application No. 60/843,942, filed on Sep. 11, 2006, provisional application No. 60/783,307, filed on Mar. 17, 2006, provisional application No. 60/673,600, filed on Apr. 21, 2005, provisional application No. 60/843,942, filed on Sep. 11, 2006.

(56) References Cited

U.S. PATENT DOCUMENTS

| | | |
|---|---|---|
| 3,702,611 A | 11/1972 | Fishbein |
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,678,468 A | 7/1987 | Hiroyoshi |
| 4,680,336 A | 7/1987 | Larsen et al. |
| 4,693,715 A | 9/1987 | Abel, Jr. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,067,961 A | 11/1991 | Kelman et al. |
| 5,087,392 A | 2/1992 | Burke et al. |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-LaBarre |
| 5,290,548 A | 3/1994 | Goldberg |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,476,515 A | 12/1995 | Kelman |
| 5,556,429 A | 9/1996 | Felt |
| 5,562,738 A | 10/1996 | Boyd et al. |
| 5,589,563 A | 12/1996 | Ward |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,763,529 A | 6/1998 | Lucas |
| 5,770,669 A | 6/1998 | Robertson et al. |
| 5,800,412 A | 9/1998 | Zhang et al. |
| 5,824,079 A | 10/1998 | Siegler et al. |
| 5,836,313 A | 11/1998 | Perez et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 6,001,894 A | 12/1999 | Ottersbach et al. |
| 6,005,160 A | 12/1999 | Hsiue et al. |
| 6,027,742 A | 2/2000 | Lee et al. |
| 6,031,017 A | 2/2000 | Waki et al. |
| 6,057,406 A | 5/2000 | Pojman et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |
| 6,224,893 B1 | 5/2001 | Langer et al. |
| 6,231,605 B1 | 5/2001 | Ku |
| 6,231,611 B1 | 5/2001 | Mosseri |
| 6,239,209 B1 | 5/2001 | Yang et al. |
| 6,251,965 B1 | 6/2001 | Wang et al. |
| 6,254,637 B1 | 7/2001 | Lee et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,331,578 B1 | 12/2001 | Turner et al. |
| 6,368,315 B1 | 4/2002 | Gillis et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Ikada et al. |
| 6,428,576 B1 | 8/2002 | Haldimann |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,679,917 B2 | 1/2004 | Ek |
| 6,689,165 B2 | 2/2004 | Jacob et al. |
| 6,726,322 B2 | 4/2004 | Andino et al. |
| 6,733,533 B1 | 5/2004 | Lozier |
| 6,740,087 B2 | 5/2004 | Knox |
| 6,755,865 B2 | 6/2004 | Tarabishy |
| 6,846,875 B2 | 1/2005 | Pennings et al. |
| 6,852,125 B2 | 2/2005 | Simon et al. |

(56) References Cited

U.S. PATENT DOCUMENTS

| | | |
|---|---|---|
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalal et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 2002/0055007 A1 | 5/2002 | Soane et al. |
| 2002/0082699 A1* | 6/2002 | Ward et al. .......... 623/17.16 |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0022216 A1 | 1/2003 | Mao et al. |
| 2003/0083389 A1 | 5/2003 | Kao et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1* | 8/2003 | Wang et al. .......... 623/22.21 |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1* | 7/2004 | Mansmann .......... 623/14.12 |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1* | 2/2005 | Kim et al. .......... 623/17.13 |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1* | 11/2005 | Winterbottom et al. ... 623/23.63 |
| 2005/0251268 A1 | 11/2005 | Truncale |
| 2005/0267482 A1 | 12/2005 | Hyde, Jr. |
| 2005/0267584 A1 | 12/2005 | Burdulis, Jr. et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0003179 A1* | 1/2006 | Wang et al. .......... 428/613 |
| 2006/0008506 A1 | 1/2006 | De Sousa et al. |
| 2006/0052878 A1 | 3/2006 | Schmieding |
| 2006/0083773 A1 | 4/2006 | Myung et al. |
| 2006/0093648 A1* | 5/2006 | Coury et al. .......... 424/426 |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0188487 A1 | 8/2006 | Thomas et al. |
| 2006/0188940 A1 | 8/2006 | Cima et al. |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde, Jr. et al. |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1* | 8/2007 | Winterbottom et al. ...... 623/23.5 |
| 2007/0198022 A1 | 8/2007 | Lang et al. |
| 2007/0202148 A1 | 8/2007 | Ringeisen et al. |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |

(56) References Cited

U.S. PATENT DOCUMENTS

| | | | |
|---|---|---|---|
| 2007/0270783 | A1 | 11/2007 | Zumsteg et al. |
| 2007/0276394 | A1 | 11/2007 | Johnson et al. |
| 2008/0058954 | A1 | 3/2008 | Trieu |
| 2008/0070086 | A1 | 3/2008 | Fukuchi et al. |
| 2008/0077249 | A1 | 3/2008 | Gradel |
| 2008/0103505 | A1 | 5/2008 | Fransen |
| 2008/0124376 | A1 | 5/2008 | Pruitt et al. |
| 2008/0241214 | A1* | 10/2008 | Myung et al. ............ 424/423 |
| 2008/0269370 | A1* | 10/2008 | Myung et al. ............ 523/105 |
| 2008/0317818 | A1 | 12/2008 | Griffith et al. |
| 2009/0035344 | A1 | 2/2009 | Thomas et al. |
| 2009/0062408 | A1 | 3/2009 | Liu et al. |
| 2009/0062423 | A1 | 3/2009 | Betz et al. |
| 2009/0088846 | A1* | 4/2009 | Myung et al. ........... 623/14.12 |
| 2009/0142508 | A1 | 6/2009 | Lai |
| 2009/0163860 | A1 | 6/2009 | Patrick et al. |
| 2009/0176891 | A1 | 7/2009 | Chogle et al. |
| 2009/0209966 | A1 | 8/2009 | Chandler |
| 2009/0221730 | A1 | 9/2009 | Kowalski et al. |
| 2009/0233887 | A1 | 9/2009 | Shalaby et al. |
| 2009/0240337 | A1 | 9/2009 | Myung et al. |
| 2010/0010114 | A1* | 1/2010 | Myung et al. ............ 523/114 |
| 2010/0032090 | A1* | 2/2010 | Myung et al. ............ 156/275.5 |
| 2010/0056646 | A1 | 3/2010 | Shalaby et al. |
| 2011/0152868 | A1 | 6/2011 | Kourtis et al. |
| 2012/0045651 | A1 | 2/2012 | Myung et al. |
| 2012/0277807 | A1 | 11/2012 | Myung et al. |
| 2013/0096691 | A1 | 4/2013 | Myung et al. |
| 2013/0138210 | A1 | 5/2013 | Myung et al. |
| 2013/0138211 | A1 | 5/2013 | Myung et al. |

FOREIGN PATENT DOCUMENTS

| | | |
|---|---|---|
| JP | 06-287443 A | 10/1994 |
| JP | 09-077809 A | 3/1997 |
| JP | 10-500038 | 1/1998 |
| JP | 2002-514233 A | 5/2002 |
| JP | 2002-518564 A | 6/2002 |
| JP | 2002-518565 A | 6/2002 |
| JP | 2003-171475 A | 6/2003 |
| WO | WO 94/01468 A1 | 1/1994 |
| WO | WO 00/02937 A1 | 1/2000 |
| WO | WO 00/43050 A1 | 7/2000 |
| WO | WO 02/26848 A2 | 4/2002 |
| WO | WO 2004/055057 A1 | 7/2004 |
| WO | WO 2004/091685 A2 | 10/2004 |
| WO | WO2007/067697 A2 | 6/2007 |
| WO | WO 2007/112305 A2 | 10/2007 |
| WO | WO 2009/071937 A1 | 6/2009 |

OTHER PUBLICATIONS

Bobyn et al., The optimum pore size for the fixation of porous-surfaced metal implants by the ingrowth of bone. Clin Orthop Relat Res, Jul./Aug. 1980(150): p. 263-70.

Borden et al.; The sintered microsphere matrix for bone tissue engineering: In vitroosteoconductivity studies; J. Biomed. Mat. Res.; 61(3); pp. 421-429; Sep. 2002.

Brodbeck et al., Biomaterial adherent macrophage apoptosis is increased by hydrophilic and anionic substrates in vivo. Proc Natl Aced Sci U S A, Aug. 6, 2002. 99(16): p. 10287-92.

Covert et al.; Friction characteristics of a potential articular cartilage biomaterial. Wear, Aug. 2003. 255: p. 1064-1068.

Dror et al.; Gradient interpenetrating polymer networks. I. Poly(ether urethane) and polyacrylamide IPN; J of Applied Polymer Science; 26; pp. 1741-1757; Jun. 1981.

Elmer's Products Inc.; Material Safety Data Sheet; "Elmer's Nano Glue"; Jun. 13, 2007.

Elsabee et al.; Gradient interpenetrating polymer networks. II. Polyacrylamide gradients in poly(ether urethane); J of Applied Polymer Science; 28(7); pp. 2151-2166; Jun. 1983.

Evans et al.; The use of corneal organ culture in biocompatibility studies; Biomaterials; vol. 23; pp. 1359-1367; Mar. 2002.

Frank, Curt; Structure-property relationships for hydrogels with applications to biomedical devices; Presentation at American Chemical Society Mtg; San Francisco, CA; Sep. 11, 2006.

Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.

Gong et al.; Double-network hydrogels with extremely high mechanical strength; Adv. Mater.; vol. 15; No. 14; pp. 1155-1158; Jul. 17, 2003.

Gorna et al.; Preparation, degradation, and clarification of biodegradable polyurethane foams for bone graft substitutes; J. Biomed Mater Res A; 67(3); pp. 813-827; Dec. 1, 2003.

Guelcher et al.; Synthesis and in vitro biocompatibility of injectable polyurethane foam scaffolds; Tissue Engineering; 12(5); pp. 1247-1259; May 2006.

Guelcher et al.; Synthesis of biocompatible segmented polyurethanes from aliphatic diisocyanates and diurea diol chain extenders; Acta biomaterialia; 1(4); pp. 471-484; Jul. 2005.

Gunatillake et al.; Designing biostable polyurethane elastomers for biomedical implants; Aust. J. Chem.; vol. 56; pp. 545-557; Jun. 2003.

Hern et al.; Incorporation of adhesion peptides into nonadhesive hydrogels useful for tissue resurfacing; J. Biomed. Materials Research; vol. 39; No. 1; pp. 266-276; Feb. 1998.

Iwasaki et al., Hydrogel like elastic membrane consisting of semi-interpenetrating polymer networks based on a phosphorylcholine polymer and a segmented polyurethane; J. Polym. Sci Part A: Polym Chem; 41; pp. 68-75; Jan. 2003.

Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.

Kim et al.; Water sorption of ploy(propylene glycol)/poly(acrylic acid) interpenetrating polymer network hydrogels; Reactive & Functional Polymers; vol. 55; pp. 69-73; Feb. 2003.

Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.

Lamba et al.; Polyurethanes in Biomedical Application; CRC Press; pp. 11, 14, 16, 18-20, 57-59, 73, 79 & 104; Nov. 1997.

Lee et al.; Interpenetrating polymer network hydrogels based on poly (ethylene glycol) macromer and chitosan; Carbohydrate Polymer; vol. 41; No. 2; pp. 197-205; Feb. 2000.

Lipatov et al.; Gradient interpenetrating polymer networks; Journal of Materials Science; 30(4); pp. 1095-1104; Feb. 1995.

Lu et al.; Release behavior of high molecular weight solutes from poly(ethylene glycol)-based degradable networks; Macromolecules; vol. 33(7); pp. 2509-2515; Mar. 2000.

Maroudas et al.; Permeability of articular cartilage; Nature; vol. 219(5160); pp. 1260-1261; Sep. 21, 1968.

Mow et al., fBasic Orthopaedic Biomechanics and Mechano-Biology, Lippincot Williams and Wilkins, 3rd Edition, Apr. 2005, pp. 459-461.

Myung, David; Structure, properties, and medical device applications of mechanically enhanced, biometric hydrogel alloys; Doctoral Thesis; Stanford University; Dec. 2007.

Myung et al.; Biomimetic strain hardening in interpenetrating polymer network hydrogels; Polymer, ; vol. 48; No. 18; pp. 5376-5387; Jun. 2007.

Park et al.; Synthesis of PVA/PVP hydrogels having two-layer by radiation and their physical properties; Radiation Physics and Chemistry; 67(3-4); pp. 361-365; Jun. 2003.

Saito et al.; Preparation and properties of transparent cellulose hydrogels; J. Applied Polymer Science; 90(11); pp. 3020-3025; Dec. 2003.

Scholes et al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596; Jul. 2006.

Shalaby; U.S. Appl. No. 61/069,046 entitled "Hydroswellable, segmented, aliphatic polyurethanes and polyurethane ureas," filed Mar. 12, 2008.

(56) References Cited

OTHER PUBLICATIONS

Spector et al.; Porous polymers for biological fixation. Clin Orthop Relat Res, Oct. 1988 (235): p. 207-19.

Stammen et al., Mechanical properties of a novel PVA hydrogel in shear and unconfined compression. Biomaterials, Apr. 2001. 22(8): p. 799-806.

Tariq et al.; (Abstract) Sodium benzoate attenuates iminodipropionitrile-induced behavioral syndrome in rats. Behav pharmacol; Dec. 2004.

Tawfik, Dan; Amidation of carboxyl groups; The Protein Protocols Handbook, 2nd Ed.; Humana Press; pp. 477-478; Feb. 2002.

The Engineering Toolbox; Polyurethane insulation: {http://www.engineeringtoolbox.com/polyurethane-insulation-k-values-d_1174.html} pp. 1-3; printed Oct. 21, 2011.

The Engineering Toolbox;Thermal conductivity of some common materials and gases; {http://www.engineeringtoolbox.com/thrmal-conductivity-d_429.html} pp. 1-2; printed Oct. 21, 2011.

The Gorilla Glue Company; Material Safety Data Sheet; "New Fast Cure-Dries White Gorilla Glue®"; Jan. 30, 2007.

The Gorilla Glue Company; Material Safety Data Sheet; "New Stronger-Faster Gorilla Glue®"; Jan. 26, 2007.

Wittemann et al.; Adsorption of proteins on spherical polyelectrolyte brushes in aqueous solution; Phys. Chem. Chem. Phys., Mar. 2003, vol. 5(8), pp. 1671-1677.

Wright et al., Wear studies on prosthetic materials using the pin-on-disc machine. Biomaterials, vol. 3, Issue 1, Jan. 1982, pp. 41R48.

Yang et al.; Preparation of poly(acrylic acid) modified polyurethane membrane for biomaterial by UV radiation without degassing; J. Biomed. Mater. Res.; vol. 45(2); pp. 133-139; May 1999.

Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

Myung et al.; U.S. Appl. No. 13/347,647 entitled "Orthopedic implants having gradient polymer alloys," filed Jan. 10, 2012.

Causton et al.; Dental materials: 1981 literature review Part 1; Journal of Dentistry; vol. 12; Issue 1; pp. 1R28; Mar. 1984.

Charnley, J.; Anchorage of the femoral head prosthesis to the shaft of the femur; J Bone Joint Surg Br.; 42-B:28-30; Feb. 1960.

Depuy Orthopaedics; Bone Cement Time Setting Chart; product file; date of publication unknown; available to applicants at least as of Jul. 2012.

Kwong et al.; A comparison of the shrinkage of commercial bone cements when mixed under vacuum; J Bone Joint Surg Br.; 88(1):120-2; Jan. 2006.

Lewis G.; Properties of acrylic bone cement: state of the art review; J Biomed Mater Res.; 38(2):155-82; Summer(Jun.-Aug.) 1997.

Morgan et al.; Dependence of yield strain of human trabecular bone on anatomic site; J Biomech.; 34(5):569-77; May 2001.

Ohman et al.; Mechanical testing of cancellous bone from the femoral head: experimental errors due to off-axis measurements; J Biomech.; 40(11);2426-33; (year of publication is sufficiently earlier than the effective U.S. filing date and any foreign priority date) 2007.

Orr et al.; Shrinkage stresses in bone cement; Biomaterials; 24 (17):2933-40; Aug. 2003.

Puska et al.; Exothermal Characteristics and Release of Residual Monomers from Fiber-reinforced Oligomer-modified Acrylic Bone Cement; J Biomat App; 20:51-64; Jul. 2005.

Stryker Orthopaedics; SimplexTM P Bone Cement; Product Literature LSB Rev. 3, Mar. 2006.

Kourtis et al.: U.S. Appl. No. 13/573,788 entitled "Polymeric adhesive for anchoring compliant materials to another surface," filed Oct. 3, 2012.

Kourtis et al.: U.S. Appl. No. 13/683,731 entitled "Systems, Devices, and Methods for Anchoring Orthopaedic Implants to Bone," filed Nov. 21, 2012.

Myung et al.; U.S. Appl. No. 13/816,537 entitled "Hydrophobic and Hydrophilic Interpenetrating Polymer Networks Derived From Hydrophobic Polymers and Methods of Preparing the Same," filed Apr. 24, 2013.

Chen et al.; Mechanical Properties of Polyepichlorohydrin Polyurethane/Poly(methyl methacrylate) IPNs; Chinese J Appl Chem; 12(4):66-69; Aug. 1995 (wEngAbs).

Ithaca College Gross Anatomy; Joints of the Back; 4 pgs. (downloaded Dec. 1, 2013 from http://www.ithaca.edu/faculty/lahr/LE2000/Back/Jointpage.htm).

Jones et al.; Sequential Polyurethane-Poly(Methylmethacrylate) Interpenetrating Polymer Networks as Ureteral Biomaterials: Mechanical Properties and Comparative Resistance to Urinaryencrustation; J Mater Sci Mater Med; 8(11):713-717; Nov. 1997.

Lam et al.; Update on Ureteral Stents; Urology; 64:9-15; Jul. 2004.

MIT.edu; Material Modulus Properties; 2pgs.; Feb. 8, 2007 (downloaded Nov. 27, 2013 from http://web.archive.org/web/*/http://web.mit.edu/course/3/3.11/www/modules/props.pdf).

Neurosurgical.com; Spinal Anatomy: The Regions of the Spine; 5pgs. (downloaded Dec. 1, 2013 http://www.neurosurgical.com/neuro_medical_info/spinal_anatomy.htm).

Realdictionary; Definition of Implant; 4pgs. (downloaded Dec. 1, 2013 from www.realdictionary.com/?q=implant).

Van Landuyt et al.; Reinforcement of Osteosynthesis Screws with Brushite Cement; Bone; 25(2)(Suppl 1):95S-98S; Aug. 1999.

\* cited by examiner

FIG. 6
FIG 6A
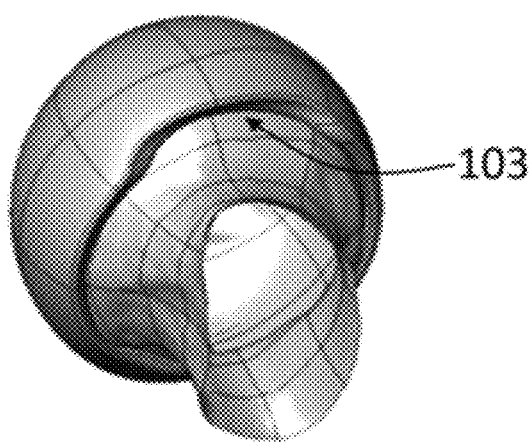
FIG 6B
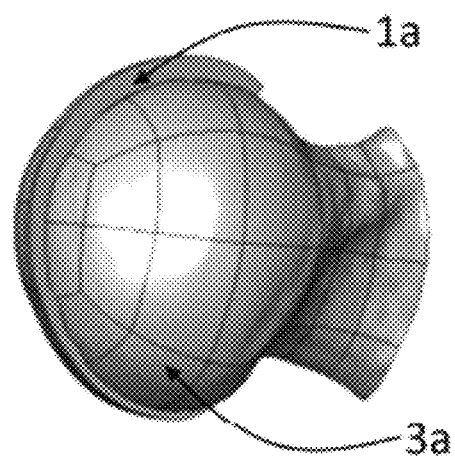
FIG 6C
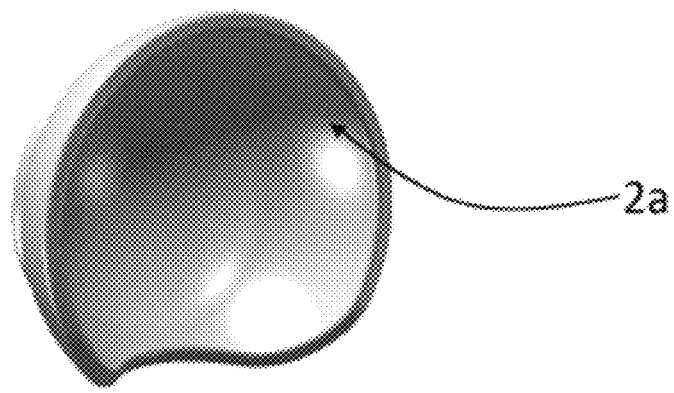

FIG. 18
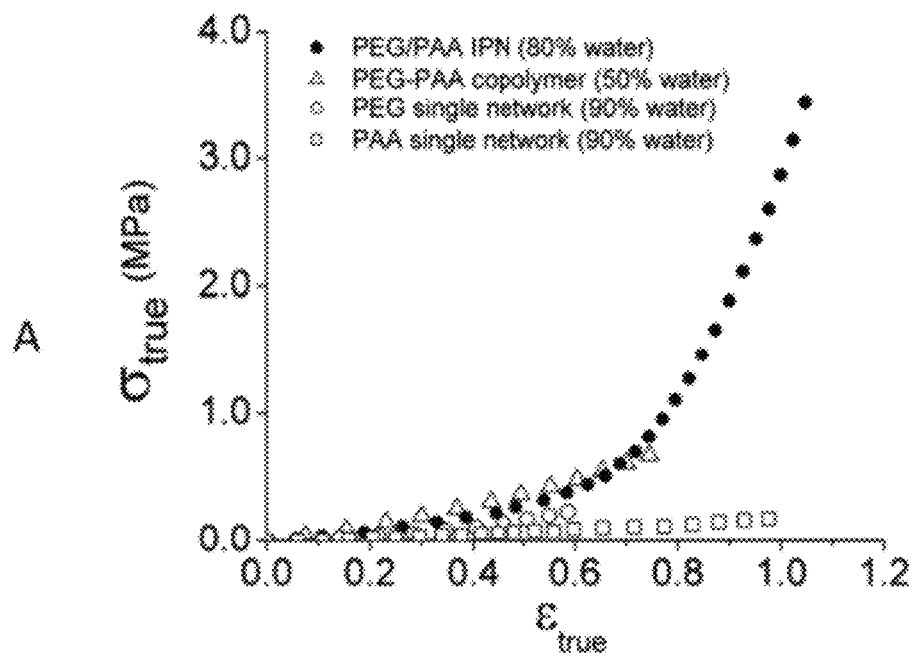
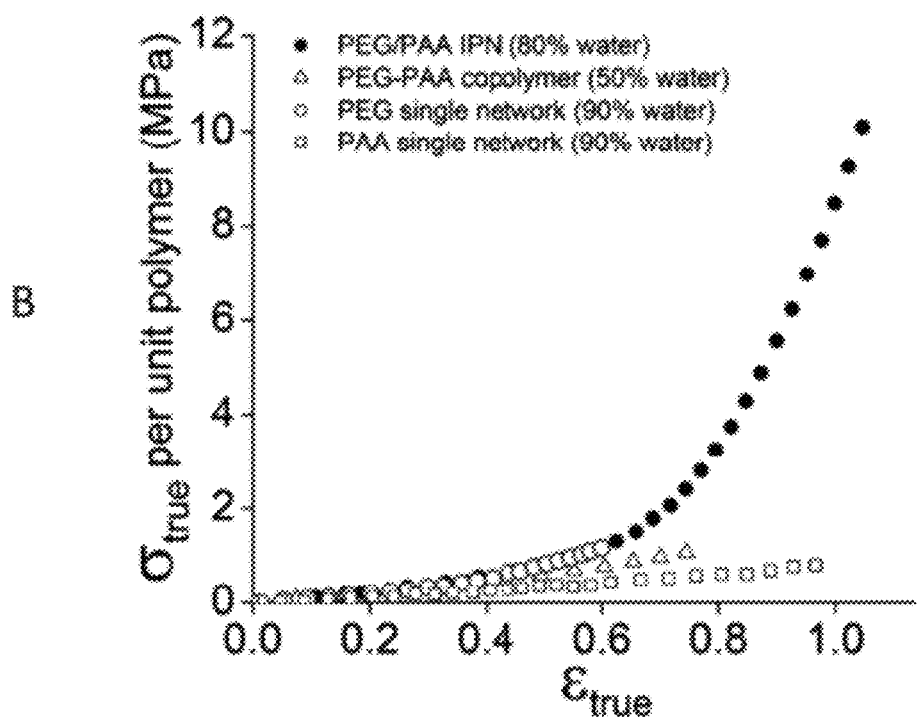

FIG. 19
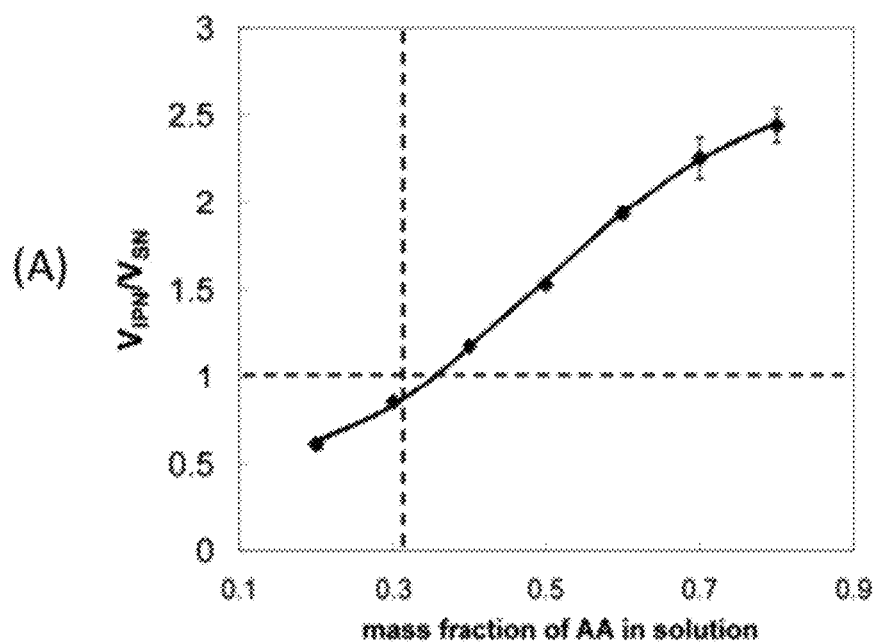
(A)
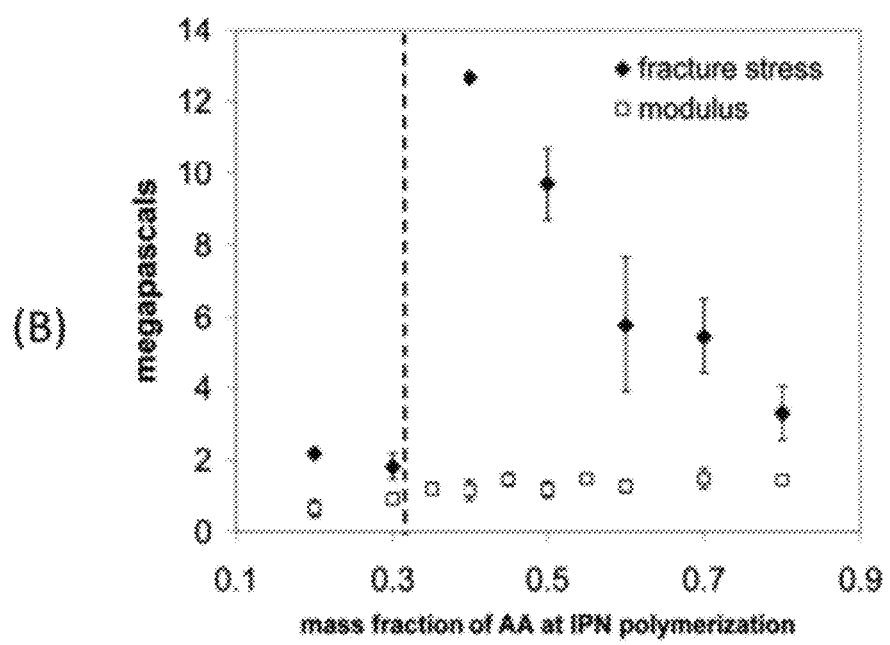
(B)

FIG. 28
Reaction A
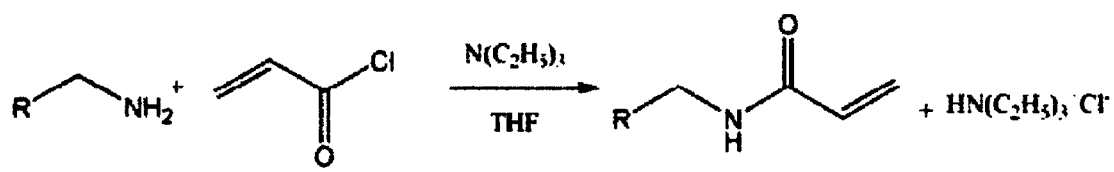
Reaction B
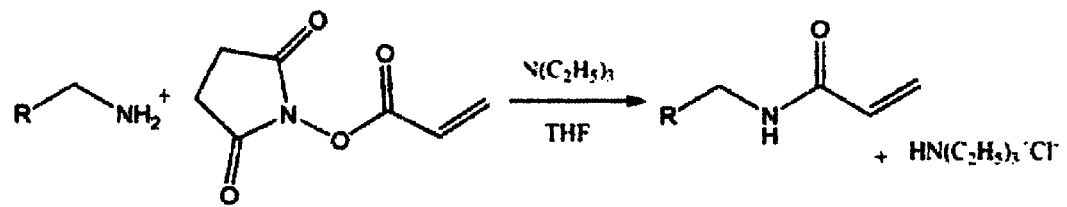

HYDROGEL ARTHROPLASTY DEVICE

CROSS REFERENCE TO RELATED APPLICATIONS

This application is a continuation of U.S. patent application Ser. No. 12/148,534, filed Apr. 17, 2008 now abandoned, which claims the benefit of U.S. Provisional Patent Application 60/923,988, filed Apr. 17, 2007, and is a continuation-in part of pending U.S. patent application Ser. No. 12/070,336, filed Feb. 15, 2008, the disclosures of all of which are incorporated herein by reference; U.S. patent application Ser. No. 12/070,336 claims priority from U.S. Provisional Application No. 60/901,805, filed on Feb. 16, 2007, and is a continuation-in part of U.S. patent application Ser. No. 11/243,952, filed Oct. 4, 2005, now U.S. Pat. No. 7,857,849, which claims the benefit of U.S. Provisional Applications 60/616,262 filed on Oct. 5, 2004 and 60/673,172 filed on Apr. 20, 2005; U.S. patent application Ser. No. 12/070,336 is also a continuation-in-part of U.S. application Ser. No. 11/636,114, filed Dec. 7, 2006, now U.S. Pat. No. 7,857,447, which claims the benefit of U.S. Provisional Application Nos. 60/843,942, filed on Sep. 11, 2006, and 60/783,307, filed Mar. 17, 2006; U.S. patent application Ser. No. 12/070,336 is also a continuation-in-part of U.S. application Ser. No. 11/409,218, filed Apr. 20, 2006, now abandoned, which claims the benefit of U.S. Provisional Application No. 60/673,600, filed Apr. 21, 2005; U.S. patent application Ser. No. 12/070,336 is also a continuation-in-part of U.S. application Ser. No. 11/639,049, filed Dec. 13, 2006, now U.S. Pat. No. 7,909,867, which claims the benefit of U.S. Provisional Application No. 60/843,942, filed on Sep. 11, 2006.

FIELD OF THE INVENTION

The present invention relates generally to interpenetrating polymer network hydrogels. More particularly, the present invention relates to devices and materials useful for orthopaedic prostheses.

BACKGROUND OF THE INVENTION

With disease or damage, the normally smooth, lubricious cartilage covering joint surfaces progressively deteriorates, exposing bone and leading to arthritic pain that is exacerbated by activity and relieved by rest. Today, patients with osteoarthritis are faced with only one of two choices: either manage their pain medically, or undergo an effective but highly bone-sacrificing surgery. Medical management includes weight loss, physical therapy, and the use of analgesics and nonsteroidal anti-inflammatories. These can be effective at reducing pain but are not curative. Other options include drugs like glucosamine or hyaluronan to replace the "lost" components of cartilage, but despite their extensive use in the U.S., their efficacy is still questioned. When medical intervention fails and a patient's joint pain becomes unbearable, surgery is advised. Total joint arthroplasty is a surgical procedure in which the diseased parts of a joint are removed and replaced with new, artificial parts (collectively called the prosthesis). In this highly effective but invasive procedure, the affected articular cartilage and underlying subchondral bone are removed from the damaged joint. A variety of replacement systems have been developed, typically comprised of ultra-high molecular weight polyethylene (UHMWPE) and/or metals (e.g. titanium or cobalt chrome), or more recently, ceramics. Some are screwed into place; others are either cemented or treated in such a way that promotes bone ingrowth. These materials have been used successfully in total joint replacements, providing marked pain relief and functional improvement in patients with severe hip or knee osteoarthritis.

A large number of patients undergo total hip arthroplasty (THA) in the US each year, which involves implanting an artificial cup in the acetabulum and a ball and stem on the femoral side. The goals of THA are to increase mobility, improve hip joint function, and relieve pain. Typically, a hip prosthesis lasts for at least 10-15 years before needing to be replaced. Yet despite its success as a surgical procedure, THA is still considered a treatment of last resort because it highly "bone-sacrificing," requiring excision of the entire femoral head. It is this major alteration of the femur that often makes revision replacement difficult. While this procedure has a survival rate of 90% or more in the elderly (who usually do not outlive the implant), implant lifetimes are significantly shorter in younger, more active patients. As a result, younger patients face the prospect of multiple, difficult revisions in their lifetime. Revisions are required when implants exhibit excessive wear and periprosthetic bone resorption due to wear particles, as well as aseptic loosening of the prosthesis resulting from stress shielding-induced bone resorption around the implant.

The aforementioned limitations of THA have prompted the industry to seek less bone-sacrificing options for younger patients, with the hope that a THA can be postponed by at least five years or more. One approach towards improving treatment has been to develop less invasive surgical procedures such as arthroscopic joint irrigation, debridement, abrasion, and synovectomy. However, the relative advantage of these surgical techniques in treating osteoarthritis is still controversial. An alternative to THA is hip "resurfacing," has now re-emerged because of new bearing surfaces (metal-on-metal, rather than metal-on-polyethylene). While many patients can expect to outlive the procedure's effectiveness, hip resurfacing preserves enough bone stock on the femoral side to allow for later total hip replacement. Unfortunately, there are enough potential drawbacks that doctors offering hip resurfacing say that the procedure should still be deferred as long as possible. In metal-on-metal resurfacing, the femoral head is shaped appropriately and then covered with a metal cap that is anchored by a long peg through the femoral neck. It requires a more precise fit between the cap and cup, and the procedure generally sacrifices more bone from the acetabulum compared to conventional replacements due to the larger diameter of the femoral component. Furthermore, a resurfacing operation has a steep learning curve and takes longer than a THA. Femoral neck fractures caused by bone resorption around the peg have been reported, and the long-term impact of metal ion release from the bearing surfaces is also not yet known in humans. As a result of these complications, today's resurfacing devices are still only indicated in patients for whom hip pain is unbearable, as is the case for THA.

The present invention addresses the needs in the art and provides an interpenetrating polymer network hydrogel that is strain-hardened by means of swelling that forms the basis of an arthroplasty device and a method for making this device.

SUMMARY OF THE INVENTION

The present invention provides a bone-sparing arthroplasty device based on an interpenetrating polymer network hydrogel that is strain-hardened by means of swelling that mimics the molecular structure, and in turn, the elastic modulus, fracture strength, and lubricious surface of natural cartilage. Emulating at least some of these structural and functional aspects of natural cartilage, the hydrogel forms the basis of a novel, bone-sparing, "biomimetic resurfacing" arthroplasty procedure. Designed to replace only cartilage, this material is fabricated as a set of flexible, implantable devices featuring lubricious articular surfaces and osteointegrable bone-interfaces. In principle, the device can be made for any joint surface in the body. For example, a device to cover the tibial plateau will require an analogous bone-preparation and polymer-sizing process. For a device to cover the femoral head in the hip joint, the analogy to a male condom is appropriate in which a cap shaped hydrogel device fits snugly over the contours of the femoral head. For a device to line the acetabulum, the analogy to a female condom is appropriate. A polymer dome stretches over the lip and can be snapped into place to provide a mating surface with the femoral head. In this way, both sides of a patient's hip joint can be repaired, creating a cap-on-cap articulation. However, if only one of the surfaces is damaged, then only one side can be capped, creating a cap-on-cartilage articulation. To create a cap-shaped hydrogel device for the shoulder joint (also a ball-and-socket joint), a process similar to that of the hip joint is used. For instance, a "female condom" can be created to line the inner aspect of the glenoid. Furthermore, devices for other joints in the hand, fingers, elbow, ankles, feet, and intervertebral facets can also be created using this "capping" concept. In one embodiment in the distal femur, the distal femur hydrogel device volume follows the contours of the bone while sparing the anterior and posterior cruciate ligaments.

More specifically, the present invention provides an arthroplasty device having an interpenetrating polymer network hydrogel that is strain-hardened by swelling and is adapted to be held in place in a mammalian joint by conforming to a naturally or artificially prepared geometry of a bone in the mammalian joint. The strain-hardened interpenetrating polymer network hydrogel is based on two different networks. The first network is a non-silicone network of preformed hydrophilic non-ionic telechelic macromonomers chemically cross-linked by polymerization of its end-groups. The second network is a non-silicone network of ionizable monomers. The second network has been polymerized and chemically cross-linked in the presence of the first network and has formed physical cross-links with the first network. Within the interpenetrating polymer network, the degree of chemical cross-linking in the second network is less than the degree of chemical cross-linking in the first network. An aqueous salt solution having a neutral pH is used to ionize and swell the second network in the interpenetrating polymer network. The swelling of the second network is constrained by the first network, and this constraining effect results in an increase in effective physical cross-links within the interpenetrating polymer network. The strain-induced increase in physical cross-links is manifested as a strain-hardened interpenetrating polymer network with an increased initial Young's modulus, which is larger than the initial Young's modulus of either (i) the first network of hydrophilic non-ionic telechelic macromonomers swollen in pure water or in an aqueous salt solution, (ii) the second network of ionized monomers swollen in pure water or in an aqueous salt solution, or (iii) the interpenetrating polymer network hydrogel formed by the combination of the first and second network swollen in pure water. The observed increase in stiffness modulus as a result of strain (induced herein by swelling) is caused by an increase in the number of physical cross-links within the interpenetrating polymer network. For the purposes of the present invention, strain-hardening is defined as an increase in the number of physical cross-links and stiffness modulus with applied strain.

The device arthroplasty has a bone-interfacing region and a bearing region opposite to the bone-interfacing region. The bone-interfacing region is characterized by conforming and capable of fixating to the naturally or artificially prepared geometry of the bone in the mammalian joint.

The device and strain-hardened interpenetrating polymer network hydrogel of the present invention could be varied according to the following embodiments either by themselves or in any combinations thereof. For example, the device can be implanted on one side of the mammalian joint forming a hydrogel-on-cartilage articulation in the mammalian joint. The device could further have a second mating component (i.e. another arthroplasty device as taught in this invention) implanted on the opposing joint surface from the implanted device forming a hydrogel-on-hydrogel articulation. The bone-interfacing region is capable of binding to calcium-containing and phosphate-containing bone-matrix constituents of the bone. In another example, the bone-interfacing region is characterized by having a porosity or surface roughness on the order of 10 to 1000 microns to accommodate bone formation. The bone-interfacing region could also be pre-coated with calcium-containing and phosphate-containing constituents. In still another example, biomolecules could be chemically or physically bonded to the bone-interfacing region.

Instead of having the bone-interfacing region be made of the strain-hardened interpenetrating polymer network hydrogel, the bone-interfacing region could, in one example, be made of a polymeric material chemically bonded to the bearing region. In this example, the bearing region is made of the strain-hardened interpenetrating polymer network hydrogel. In another example, the bearing region and the bone-interfacing region could have different compositions at either side of the device and are physically or chemically and physically integrated with each other within the device.

An adhesive material (biodegradable or non-biodegradable) could be bonded to the bone-interfacing region and would then be capable of bonding the device via the bone-interfacing region to the bone. In another example the device could include a calcium-containing inorganic coating that is chemically or physically bonded to the bone-interfacing region.

In still another example, it is a desire to approximately match the thickness profile of the device to the natural thickness profile of an original cartilage layer. The device can be adapted to fit over a primarily convex or concave three-dimensional bone-receiving surface. In one example, the device is undersized to fit over a primarily convex bone-receiving surface to create an elastic contraction fit over the convex three-dimensional bone-receiving surface. The device is capable of swelling to a swollen equilibrium volume in a fluid and temperature other than body fluids and body temperature prior to implantation and capable of de-swelling to a smaller equilibrium volume, compared to the swollen equilibrium volume, upon implantation and exposure to body fluids or/and body temperature, whereby at the smaller equilibrium volume, the device contracts against or physically grips said primarily convex three-dimensional bone receiving surface.

In another example, the device is oversized to fit against a primarily concave three-dimensional bone-receiving surface to accommodate an elastic expansion fit against the primarily concave bone-receiving surface. The device is capable of at least partially drying or de-swelling to a dried or de-swollen equilibrium volume in a fluid and temperature other than body fluids and body temperature prior to implantation and capable of swelling to a larger equilibrium volume, compared to the dried or de-swollen equilibrium volume, upon implantation and exposure to body fluids and/or body temperature, whereby the larger equilibrium volume expands the device against a primarily concave three-dimensional bone receiving surface.

The hydrophilic non-ionic macromonomer in the first network has a molecular weight between about 275 Da to about 20,000 Da, about 1000 Da to about 10,000 Da, or about 3000 Da to about 8000 Da. In another example, the molar ratio between the ionizable monomers and the hydrophilic non-ionic telechelic macromonomers is greater than or equal to 1:1 or greater than 100:1. In one example, the hydrophilic non-ionic telechelic macromonomer in the first network is a derivative of poly(ethylene glycol), and the ionizable monomers are acrylic acid monomers.

In still another example, the aqueous salt solution has a pH in the range of about 6 to 8. In still other examples, the first network has at least about 50%, at least 75% or at least 95% by dry weight telechelic macromonomers. In still another example, the first network has hydrophilic monomers grafted onto the first network. In still another example, the second network further has hydrophilic macromonomers grafted onto the second polymer network. In still another example, the strain-hardened interpenetrating polymer network hydrogel has a tensile strength of at least about 1 MPa. In still another example, the strain-hardened interpenetrating polymer network hydrogel has an initial equilibrium tensile modulus of at least about 1 MPa. In still another example, the strain-hardened interpenetrating polymer network hydrogel has an equilibrium water content of at least 25%, 35% or 50%. In still another example, the strain-hardened interpenetrating polymer network hydrogel is permeable to the aqueous salt solution and the hydrogel has a permeability coefficient ranging from 1e-17 to 1e-13 m4/Nsec.

In still another example, the coefficient of friction of the bearing region of the strain-hardened interpenetrating polymer network hydrogel in an aqueous solution is less than 0.2. In still another example, one side of the device is modified with another polymeric material, other functional groups, or biomolecules using bifunctional crosslinkers. In one example, the biomolecules could be used to stimulate bone cell growth and/or adhesion. In yet another example, the device is comprised of stimulus-responsive polymeric materials that allow it to shrink or swell to conform to the convexity or concavity of an adjacent joint surface.

BRIEF DESCRIPTION OF THE FIGURES

The present invention together with its objectives and advantages will be understood by reading the following description in conjunction with the drawings, in which:

FIG. 5A shows a dislocated joint exposing the acetabulum 4a and the femoral head 3a. A male hydrogel device component 1a is placed on the femoral head 3a and held in place by means of a stretch-to-fit. Similarly, the acetabulum device component 2a is placed in the acetabulum bone 4a and held in place by means of an expansive press-fit. FIG. 5B shows that after the components are implanted in place, the joint is reduced.

FIG. 6 shows according to an embodiment of the invention a three dimensional version of the hip arthroplasty. FIG. 6A shows a lateral view of the femoral head hydrogel device component 1a; a recess 103 that accommodates bone vessels is also shown. FIG. 6B depicts the femoral head bone 3a and a cross section of the femoral head device component 1a. FIG. 6C depicts the acetabulum device component 2a.

FIG. 7 shows according to an embodiment of the invention a two-sided (total) or one-sided hemi-arthroplasty. In this embodiment, the femoral device component 1a is stretched over the femoral head bone 3a while the acetabulum component 2a is press-fit in the acetabulum recess 4a. The bone interface regions 6 are porous and coated with hydroxyapatite to ensure bone ingrowth and the bearing regions 5 have lubricious properties to facilitate relative sliding. Furthermore, a depression 100 in the acetabulum component 4a is present that forms a chamber 101 that is filled with pressurized synovial fluid 102; the chamber is sealed by the two device components 1a, 2a.

FIG. 9A shows a lateral cross sectional view of the tibial plateau 4b and the facet 112. FIG. 9B shows the depression 113 surgically made by means of punching the bone; it further depicts the hydrogel device component 2b before implantation. FIG.

9C shows the tibial hydrogel device component 2b inserted in the depression of the facet 113.

Figure 10:
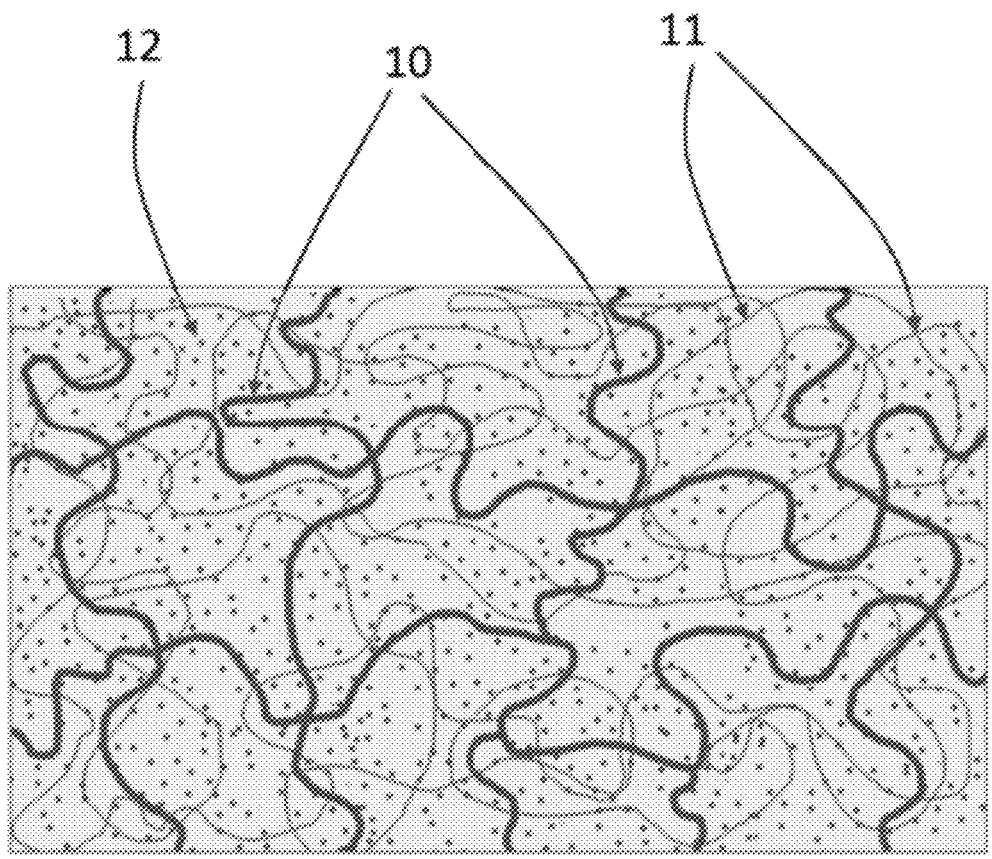

FIG. 10 shows according to an embodiment of the invention a structure of an interpenetrated polymer network based on an end-linked macromonomer network 10 and an ionized, monomer-based network 11 which is swollen and osmotically pre-stressed with a buffered, aqueous salt solution 12.

Figure 11:
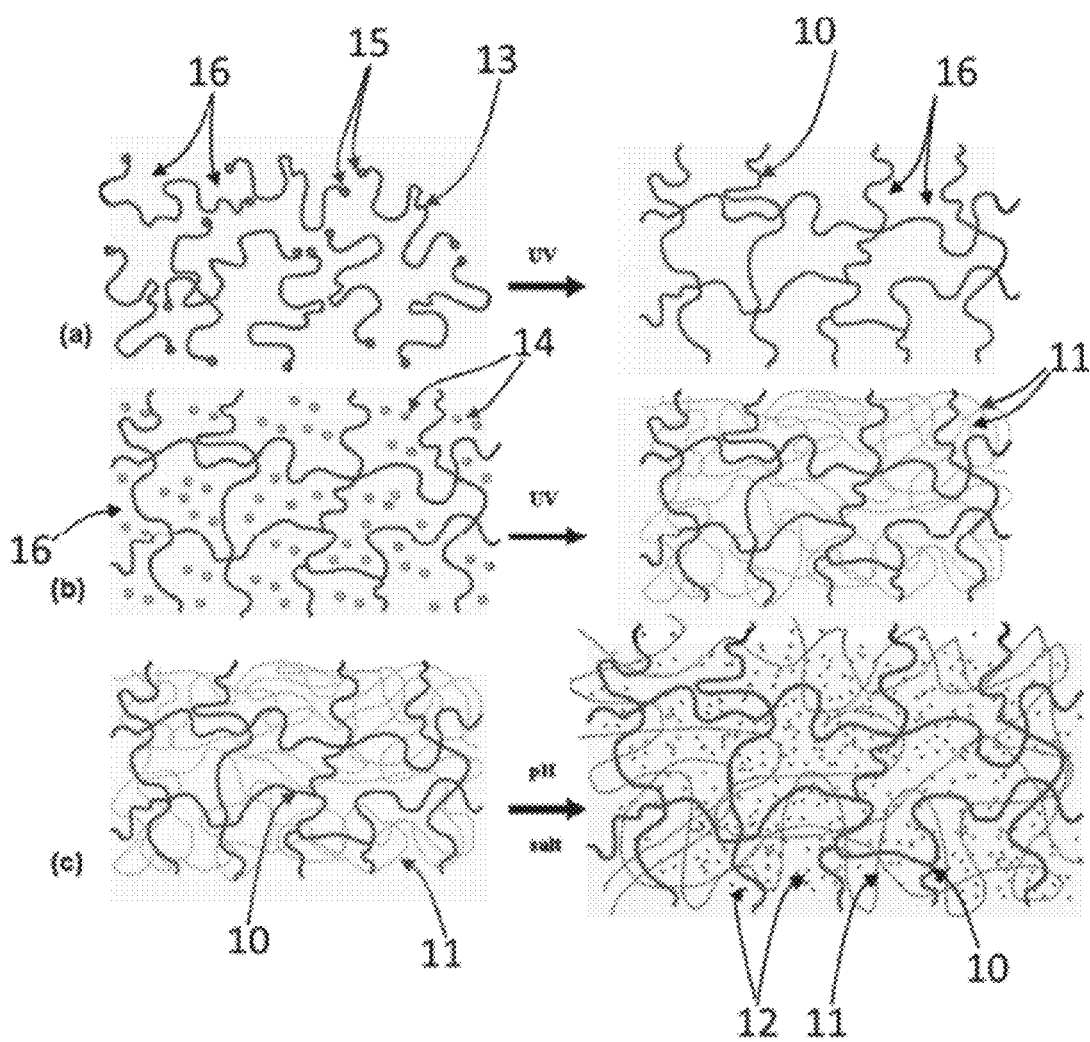

FIG. 11 shows according to an embodiment of the invention the steps for synthesis of the IPN hydrogel.

1. The starting material for the hydrogel is a solution of telechelic macromonomers 13 with reactive functional end groups 15 dissolved in water 16. The telechelic macromonomers are polymerized to form a first end-linked polymer network 10 swollen in water 16.

2. Hydrophilic, ionizable monomers 14 mixed with water are added to the first polymer network 10 along with a photoinitiator and a crosslinking agent (not shown). The hydrophilic, ionizable monomers are then photopolymerized and cross-linked in the presence of first polymer network 10 to form the second polymer network 11 in the presence of the first. This results in formation of an IPN hydrogel having an end-linked polymer network 10 interpenetrated with a ionizable second network 11 swollen in water 16.

3. The water-imbibed IPN is then immersed in an aqueous salt-containing solution 12 at a typical pH of 7.4 and is swollen to equilibrium, yielding a simultaneous increase in both the water content and the stiffness modulus of the IPN. This IPN swollen in the aqueous salt solution 12 has a higher tensile elastic modulus compared to the IPN swollen in pure water 16 due to strain hardening induced by swelling of the second network 11 within the constraint posed by the highly crosslinked first network 10.

Figure 12:
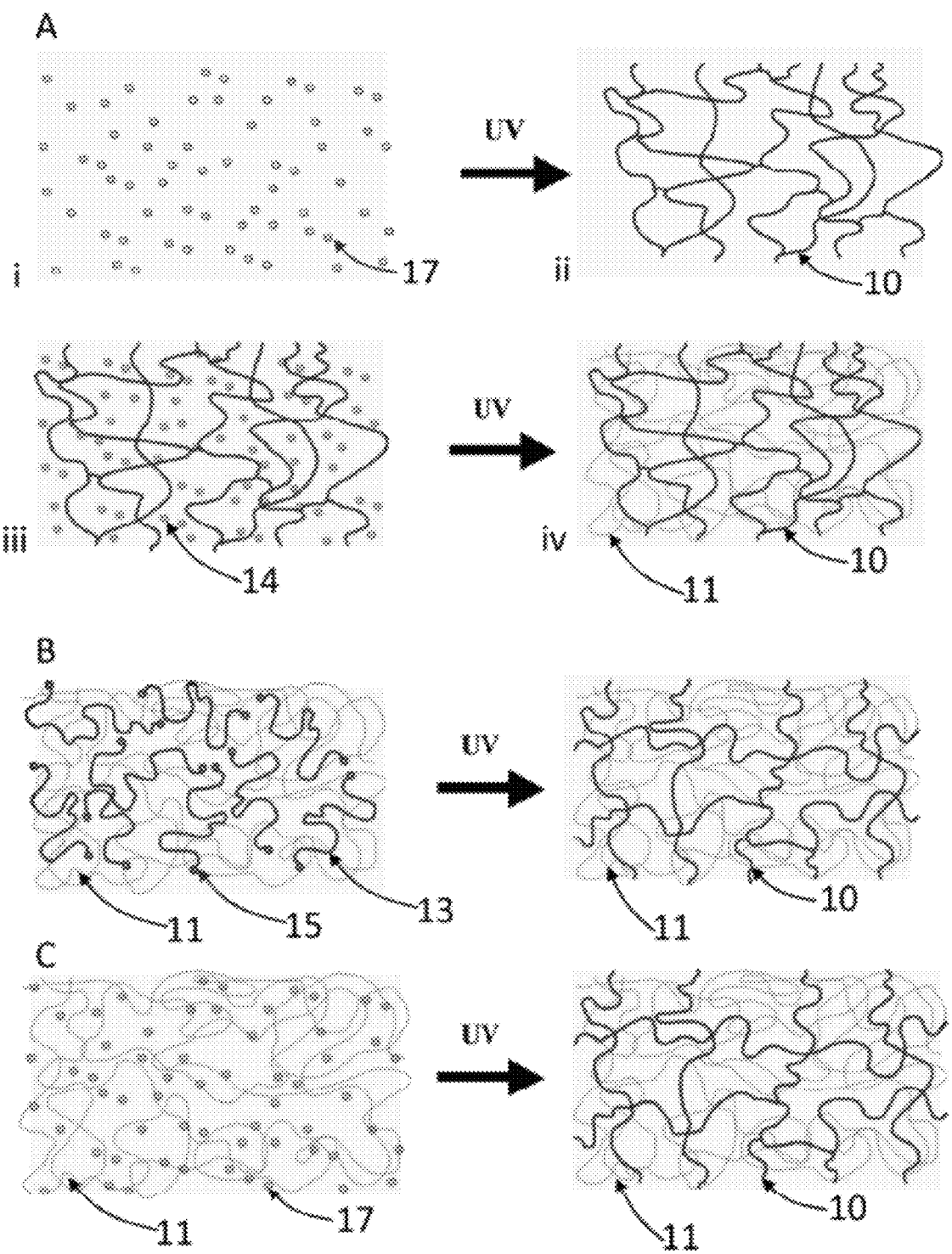

FIG. 12 A. shows according to an embodiment of the present invention method steps of how an IPN is prepared after monomers 17 are used to make the first network 10. Exposure to UV light in the presence of a photoinitiator and crosslinker (not shown) leads to polymerization and crosslinking to form a network 10, depicted by the transition from (i) to (ii). In (iii) to (iv), the first network is swollen with the second network precursor monomers 14, a crosslinking agent (not shown) and a photoinitiator (not shown). Exposure to UV light initiates polymerization and crosslinking of the second network 11 in the presence of the first (10) to form the IPN.

FIG. 12 B. shows according to an embodiment of the present invention method steps of how an IPN is prepared after macromonomers 13 with reactive endgroups 15 are used to form a first network 10 in the presence of an existing second network 11 or linear macromolecules and/or biomacromolecules. A mixture of the first and second polymeric components is made, and then the telechelic macromonomers 13, 15 are reacted under UV light to form the first network 10 in the presence of the second 11. If the second network 11 is crosslinked chemically, then it is a fully interpenetrating network. If it is not (and only physically crosslinked), then it is a semi-interpenetrating network.

FIG. 12 C. shows according to an embodiment of the present invention method steps of how an IPN is formed from a first network 10 based on monomers 17 and a second network 11 or linear macromolecules and/or biomacromolecules. A mixture of the monomers 17 and macromolecules is made, and then the monomers are reacted under UV light to form the first network in the presence of the second 11. If the second network 11 is crosslinked chemically, then it is a fully interpenetrating network. If it is not (and only physically crosslinked), then it is a semi-interpenetrating network.

Figure 13:
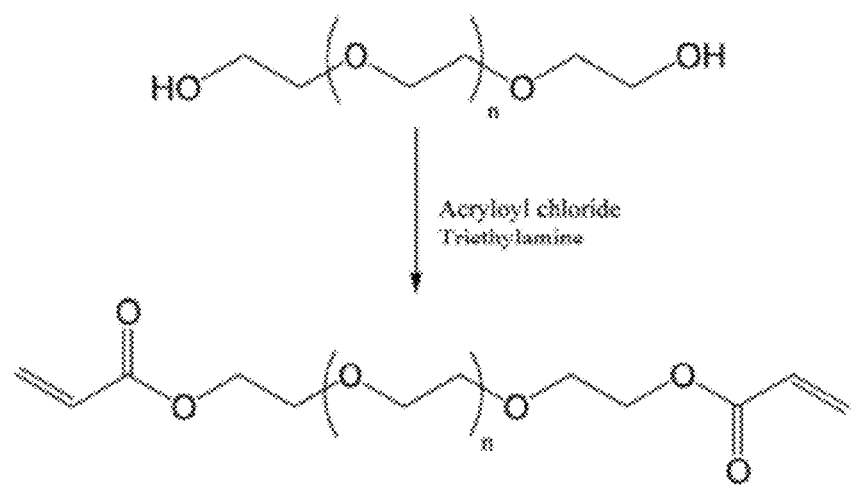

FIG. 13 shows according to an embodiment of the present invention a schematic of the synthesis of telechelic PEG-diacrylate from a PEG-diol macromonomer. To generate PEG-dimethacrylate, methacryloyl chloride would be reacted with the PEG-diol instead of acryloyl chloride.

Figure 14:
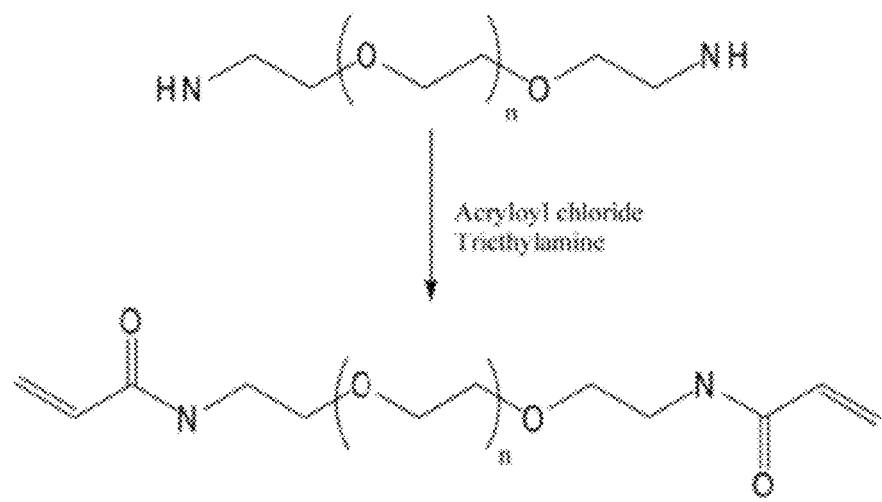

FIG. 14 shows according to an embodiment of the present invention a schematic of the synthesis of telechelic PEG-diacrylamide from a PEG-diol macromonomer. To generate PEG-dimethacrylamide, methacryloyl chloride would be reacted with the PEG-diol instead of acryloyl chloride.

Figure 15:
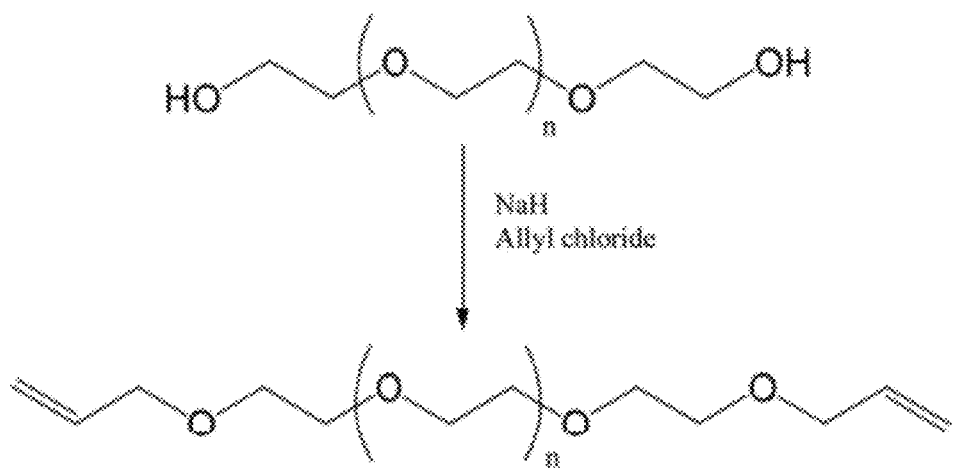

FIG. 15 shows according to an embodiment of the present invention a schematic of the synthesis of telechelic PEG-allyl ether from a PEG-diol macromonomer.

Figure 16:
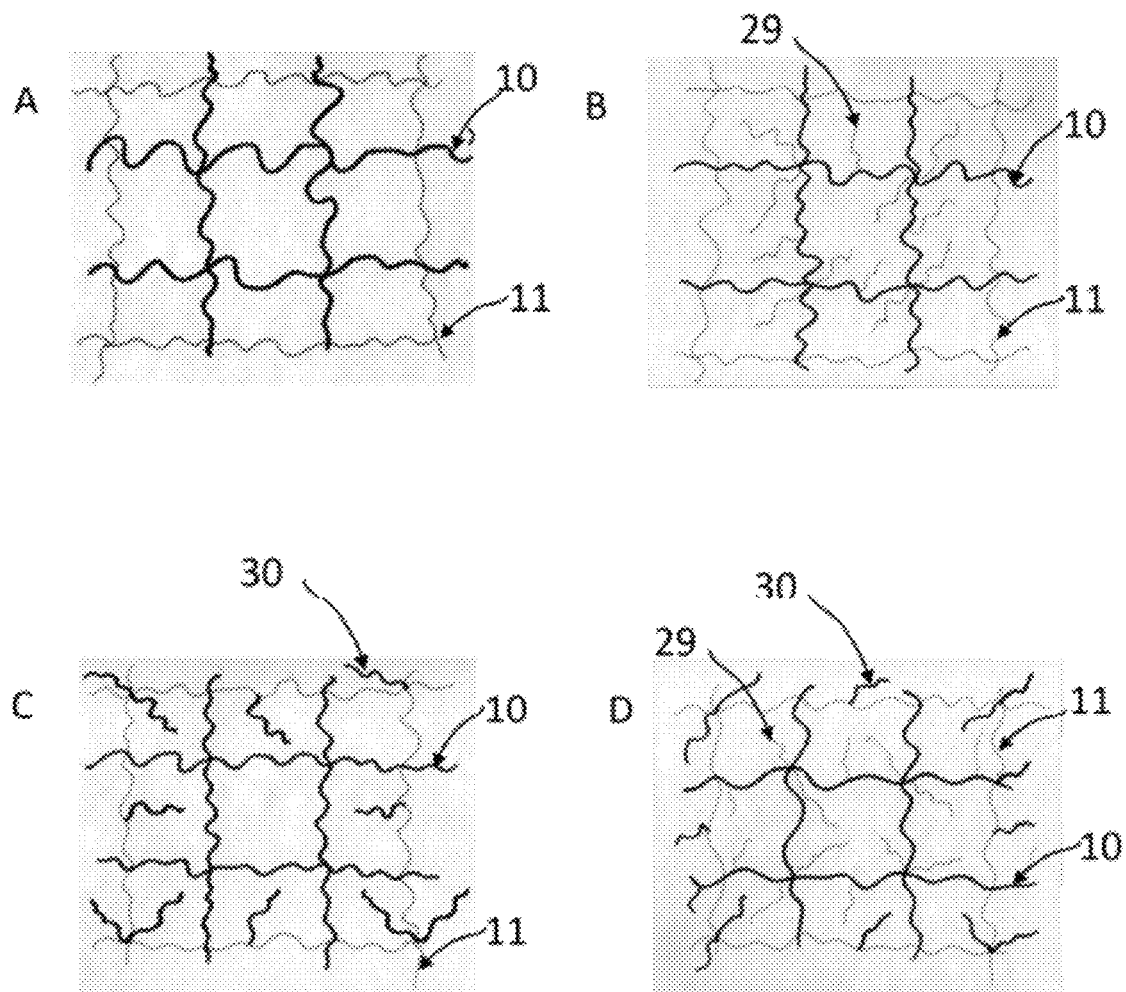

FIG. 16 shows according to embodiments of the present invention: (A) an IPN with a first network (10 and second network 11 based on two different polymers, (B) an IPN with a graft-copolymer 29 attached to the first network 10 and a homopolymer in the second network 11, (C) an IPN with a homopolymer in the first network 10 and a graft-copolymer 30 in the second network 11, and (D) an IPN with graft-copolymers (29, 30 in both the first and the second networks 10, 11.

Figure 17:
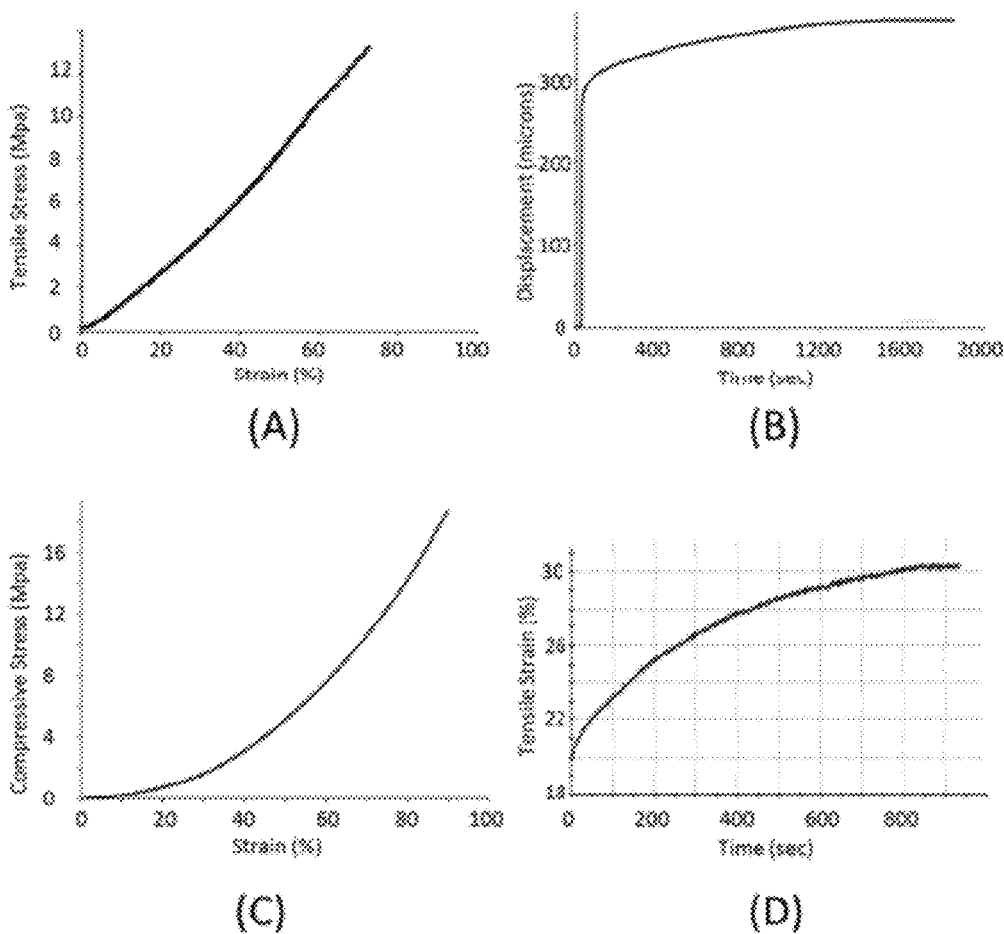

FIG. 17 shows according to the present invention the mechanical behavior of a PEG(3.4 k)/PAA IPN prepared with 70% volume fraction of acrylic acid in the second network: (A) stress-strain profile under tension, (B) stress-strain under confined compression, (C) stress-strain profile unconfined compression, and (D) strain versus time in a tensile creep experiment.

FIG. 18 A. shows according to an embodiment of the present invention true stress-true strain curves for PEG(8.0 k)/PAA IPN, PEG(8.0 k)-PAA copolymer, PEG(8.0 k), and PAA networks. B. shows according to an embodiment of the present invention normalized true stress-true strain curves for PEG(8.0 k)/PAA IPN, PEG(8.0 k)-PAA copolymer, PEG(8.0 k), and PAA networks.

FIG. 19 A. shows according to an embodiment of the present invention the effect of the mass fraction of acrylic acid (AA) monomer in the second network precursor solution on the volume change in the resultant IPN. The vertical dotted line indicates the point of equimolar amounts of AA and ethylene glycol (EG) monomer units in the IPN, while the horizontal dotted line indicates where the PEG network and the PEG/PAA IPN have the same volume.

FIG. 19 B. shows according to an embodiment of the present invention the dependence of the fracture stress and Young's modulus of the PEG/PAA IPN on the mass fraction of AA in the IPN. The vertical dotted line indicates the point of equimolar amounts of AA and ethylene glycol (EG) monomer units in the IPN.

Figure 20:
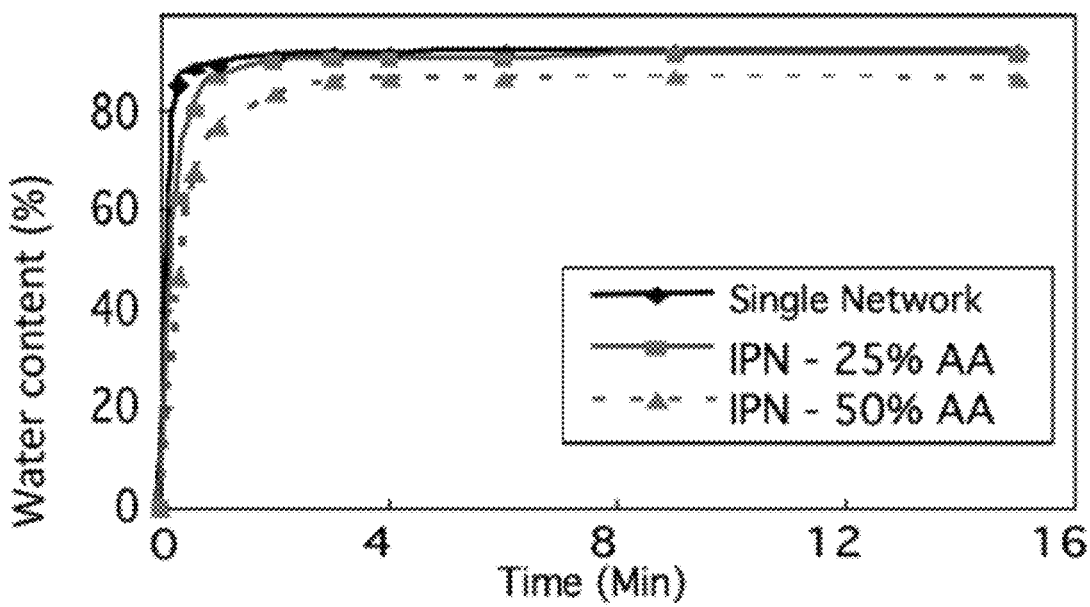

FIG. 20 shows according to an embodiment of the present invention time-dependence of the water content of single network PEG(8.0 k) hydrogels and PEG(8.0 k)/PAA IPNs with different amounts of acrylic acid (AA) at the time of polymerization. The hydrogels were placed in deionized water in the dry state at time=0 and then weighed at regular intervals.

Figure 21:
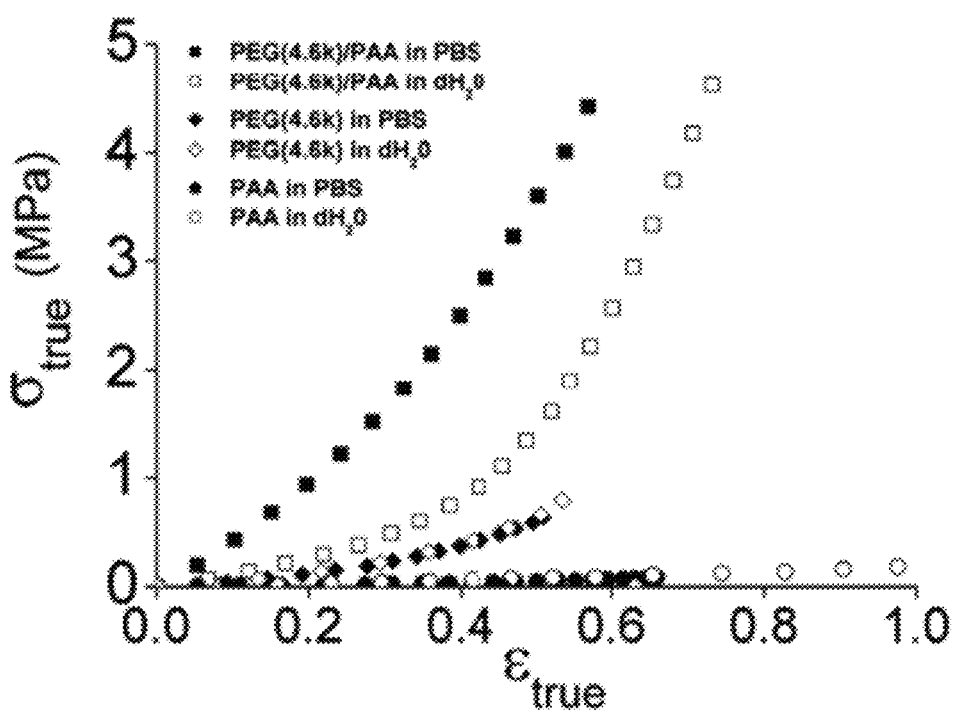

FIG. 21 shows according to an embodiment of the present invention true stress versus true strain curves of the PEG(4.6 k)/PAA IPN in PBS and deionized water, as well as the PEG and PAA single networks in PBS and deionized water. The PEG(4.6 k) network is unaffected by the change from water to PBS. The arrow indicates the shift in the stress-strain profile of the IPN after it has been strain-hardened by swelling to equilibrium in PBS.

Figure 22:
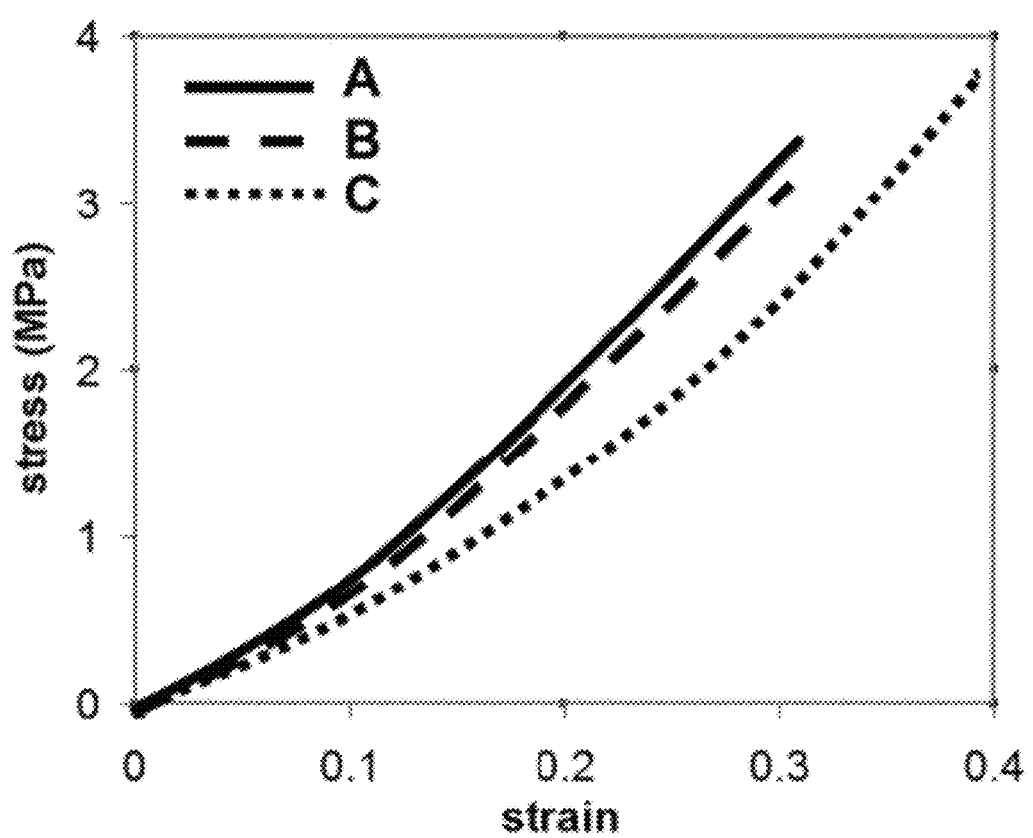

FIG. 22 shows according to an embodiment of the present invention the stress-strain profiles of PEG(4.6 k)/PAA IPNs prepared with three different combinations of crosslinker chemical end-groups but the same formulations of PEG (MW 4.6 k, 50% by weight in water) and AA (50% v/v in water) as well as the same polymerization conditions (photoinitiator and crosslinker concentration by mole and UV intensity) and swelling conditions (PBS at pH 7.4). Specimen (A) was prepared from PEG-diacrylamide first network and a PAA second network crosslinked with N,N'-(1,2-dihydroxyethylene) bisacrylamide. Specimen (B) was prepared from PEG-diacrylamide first network and a PAA second network crosslinked with triethylene glycol dimethacrylate. Specimen (C) was prepared from PEG-diacrylate first network and a PAA second network crosslinked with triethylene glycol dimethacrylate.

Figure 23:
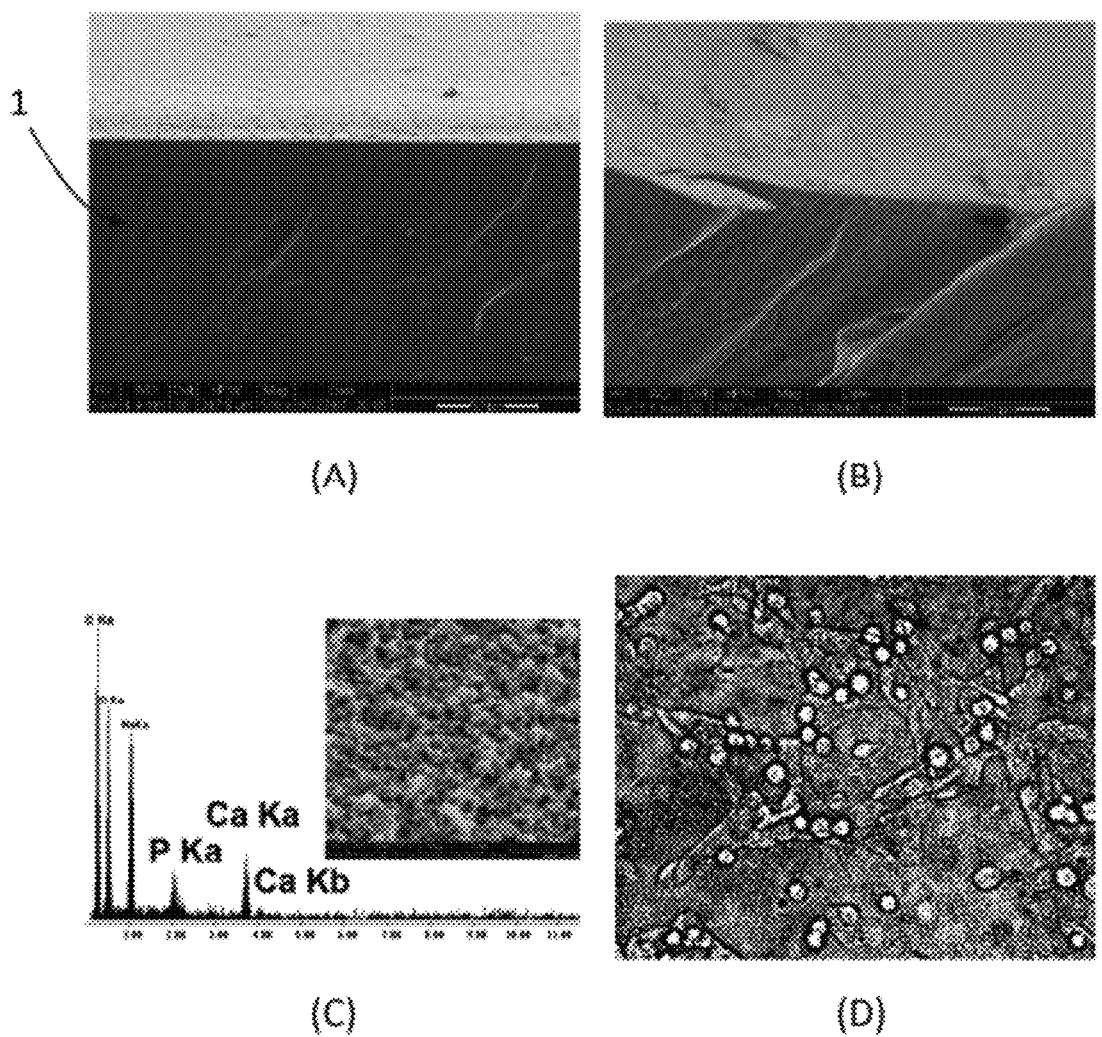
Figure 24:
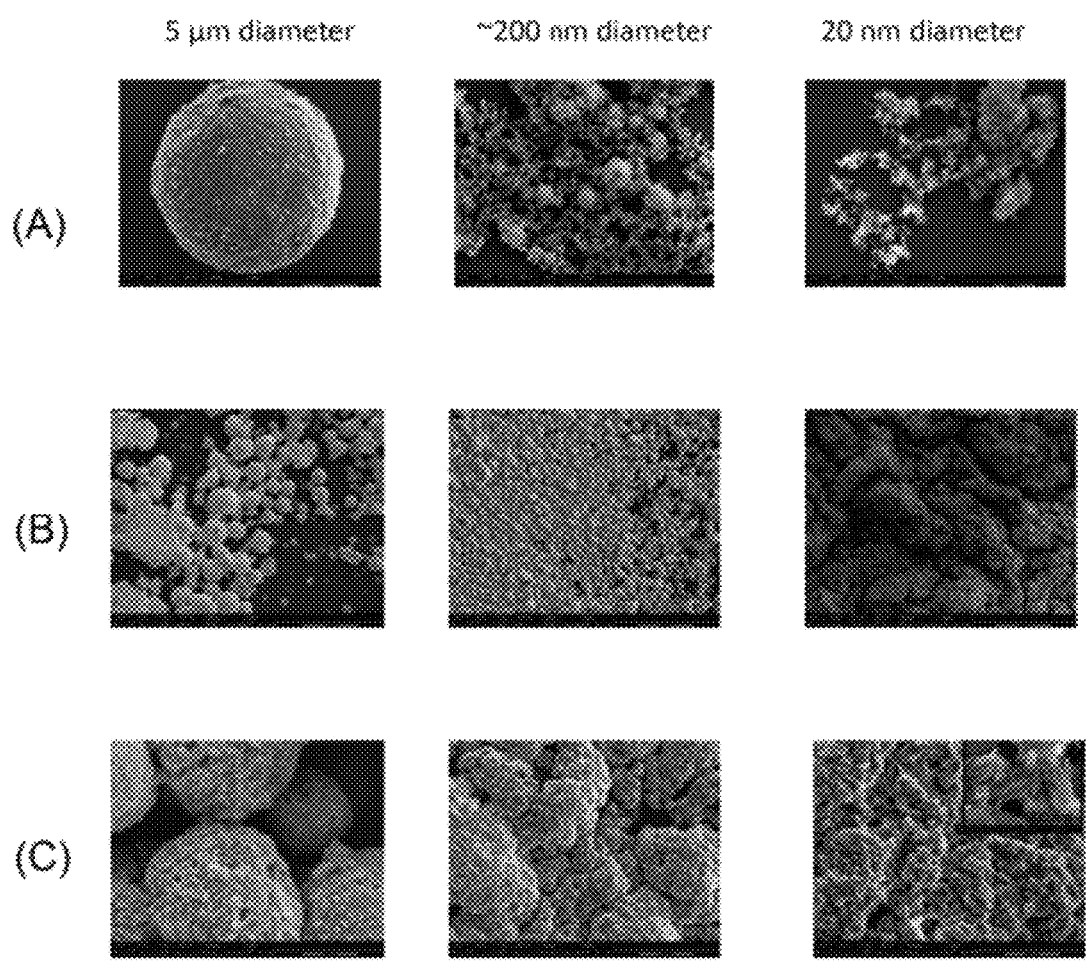

FIG. 23 (A) shows according to the invention SEM of a plain PEG/PAA sample (without hydroxyapatite) showing fractured edge (dark) and top surface (light), (B) shows according to the invention SEM of a hydroxyapatite-coated PEG/PAA sample showing fractured edge (dark) and top surface (light). (C) shows according to the invention energy-dispersive X-ray spectroscopy (EDX) analysis of the hydroxyapatite-coated PEG/PAA IPN (inset), showing a Ca/P ratio of roughly 1.5-1.6, similar to that of HAP, with an inset showing a high-magnification SEM image of HAP-coated PEG/PAA. (D) shows according to the invention osteoblast-like cells growing on PEG/PAA hydrogel coated with 200-nm diameter HAP FIG. 24 shows according to the invention SEMs of hydroxyapatite coatings of differing diameter (5 μm, ~200 nm, and 20 nm) on bare silica (Row A) and on PEG/PAA IPNs (at low magnification in Row B and at high magnification in Row C).

Figure 25:
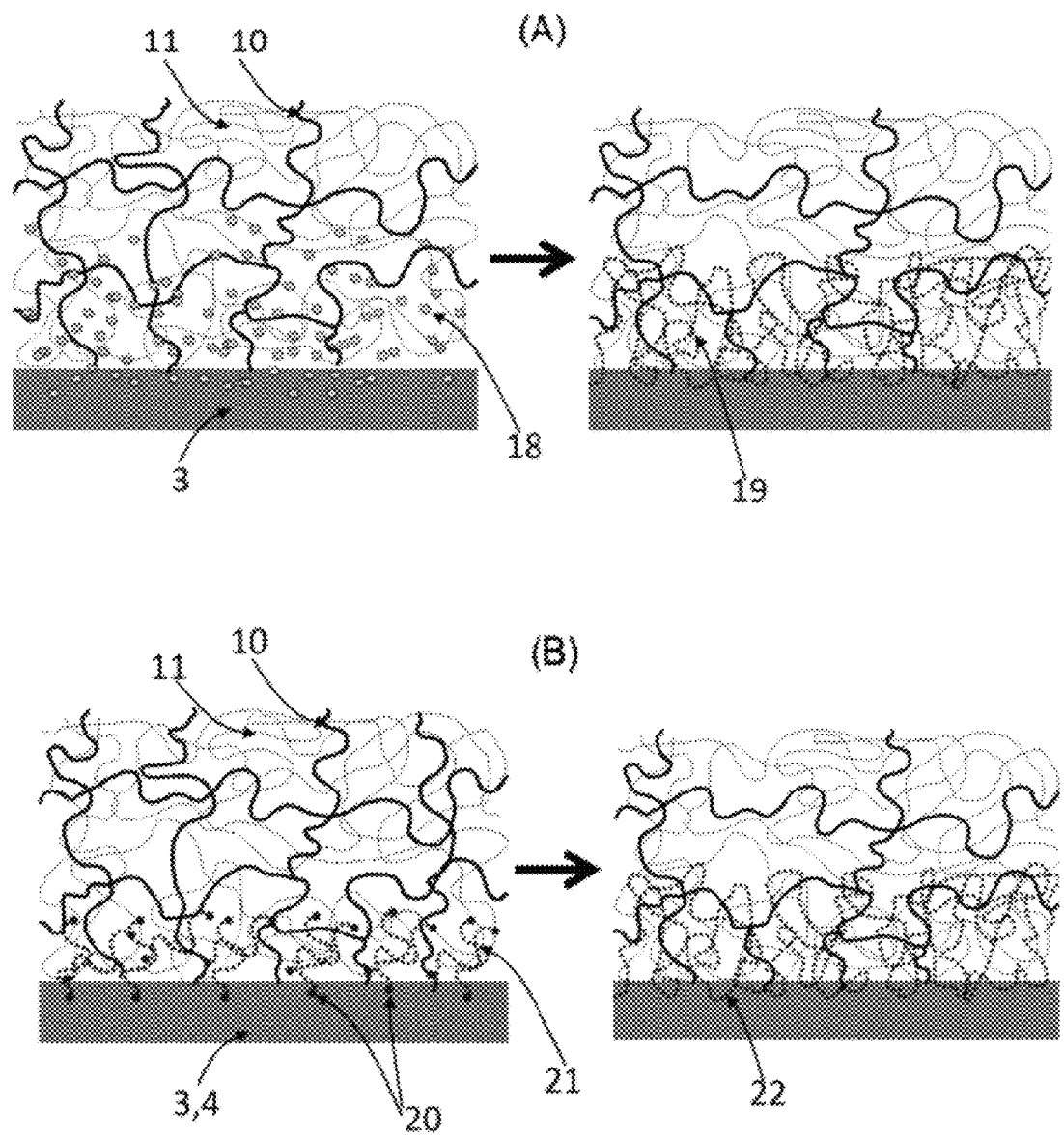

FIG. 25 A. shows according to the invention a bonding process for an IPN hydrogel 10, 11 bonding to bone (convex 3 or concave 4) through an intervening polymeric adhesive based on monomers 18. The monomers react when exposed to UV, photoinitiator, and crosslinker to form a third network 19 that is physically or physically and chemically crosslinked to the IPN hydrogel and to bone.

FIG. 25B. shows according to the invention a bonding process of an IPN hydrogel 10, 11 bonding to bone 3, 4 through an intervening polymer adhesive based on macromonomers 21 with reactive end-groups 20. The macromonomers react to form a third macromonomeric network 22 that is physically or physically and chemically crosslinked to the IPN hydrogel and to bone.

Figure 26:
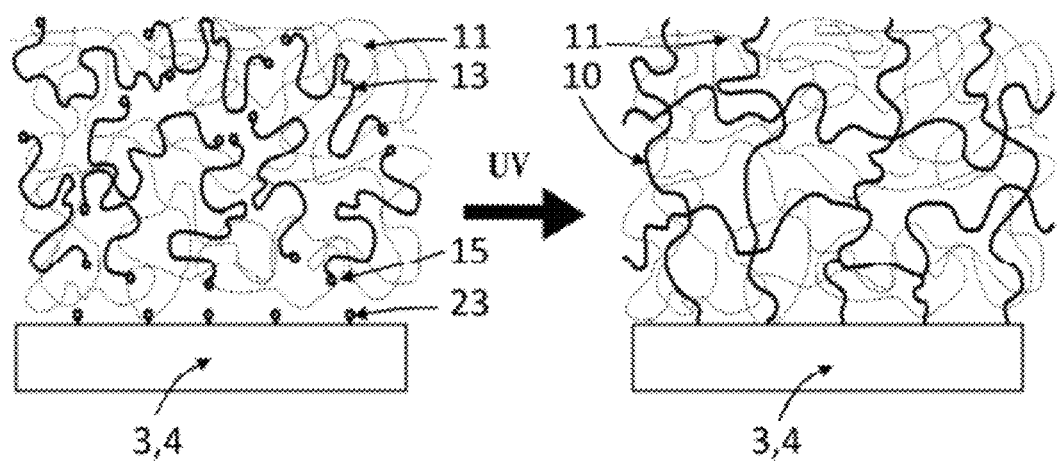

FIG. 26 shows according to the present invention a semi-interpenetrating network in which one of the networks acts as the anchoring intervening polymer. Telechelic macromonomers 13 with reactive end-groups 15 and physical network 11 or solution of linear chains are mixed together and cast over a bone surface 3, 4 that is pre-coated and/or functionalized with UV-sensitive crosslinkable groups 23. Exposure to an initiating source (e.g. UV light) in the presence of a photoinitiator leads to free-radical polymerization and crosslinking of these crosslinkable groups on both the telechelic macromonomers and the coated/functionalized bone surface. The result of free-radical polymerization and crosslinking is shown on the right. The ends of the telechelic macromonomers have formed a network 10 and have copolymerized and bonded with the surface of the bone. The linear second network polymers are physically trapped within this first network, forming a second, physically crosslinked network 11 interpenetrating the first chemically crosslinked network.

Figure 27:
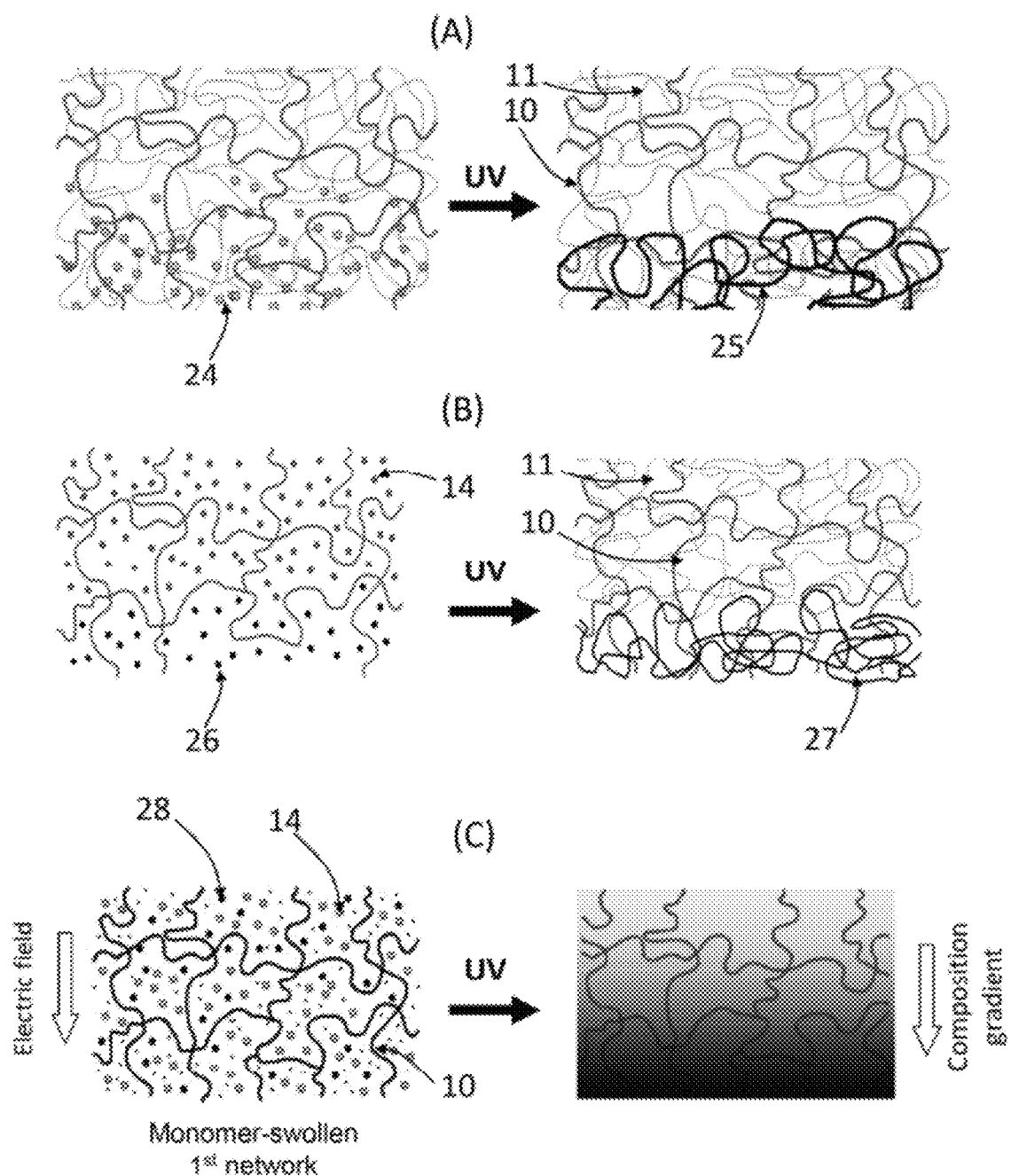

FIG. 27 A. shows according to an embodiment of the invention a fully interpenetrating network in which a third network is partially interpenetrated within the pre-existing IPN by interdiffusion of the third network monomer 24 for a predetermined time and then polymerizing the monomer in the presence of the IPN 10, 11. This yields what is effectively a third network 25 on one side of the IPN hydrogel, which may have different properties than the other side, and are properties that may be useful as a bone-interface region.

FIG. 27 B. shows according to an embodiment of the invention a fully interpenetrating network in which the second network monomer 14 is interfacially copolymerized with another monomer 26 that when polymerized acts as the bone-interfacing material. A pre-existing first network is swollen with the precursor monomers of a second network. At the bone-interface side of the material is a precursor solution of another reactive monomer 26. These monomers partially penetrate the matrix of the first network. Upon exposure to UV, the monomers co-polymerize, yielding a material with a one type of IPN 10, 11 on the bearing side and another type of IPN (10, 27 on the bone-interfacing side.

FIG. 27 C. shows according to an embodiment of the invention in which an external stimulus is used to create a composition gradient in the second network within the first network of the IPN. A mixture of acrylic acid and non-ionic monomers (e.g. acrylamide, N-isopropylacrylamide, or hydroxylethylacrylate monomers) is used. The first network 10 is soaked in a solution of ionizable monomer 14, non-ionic monomer 28, crosslinker and photoinitiator (not shown) and then an electric field is applied to the gel. Only the ionizable monomers will move along the electric field due to their charge. After formation of a ionizable monomer concentration gradient, the gel is exposed to UV and the gradient is fixed via second network gel formation. The result is an IPN hydrogel with a second network localized to the bearing region and a non-ionic second network localized to the bone-interface region.

FIG. 28 shows according to an embodiment of the invention two examples of other device surface modification strategy. This strategy involves the acrylation/methacrylation of an amine-containing or hydroxyl-containing molecule or biomolecule by reaction with a halogenated (active) acid (e.g. acryloyl chloride) (Reaction A) or with an active ester (e.g. acryloxy-N-hydroxysuccinimide) (Reaction B) to make it capable of copolymerizing with the precursor of one of the networks in the device. The R-group in the these reaction schemes can be any amine-containing or hydroxyl-containing synthetic chemical or polymer, proteins, polypeptides, growth factors, amino acids, carbohydrates, lipids, phosphate-containing moieties, hormones, neurotransmitters, or nucleic acids.

Figure 29:
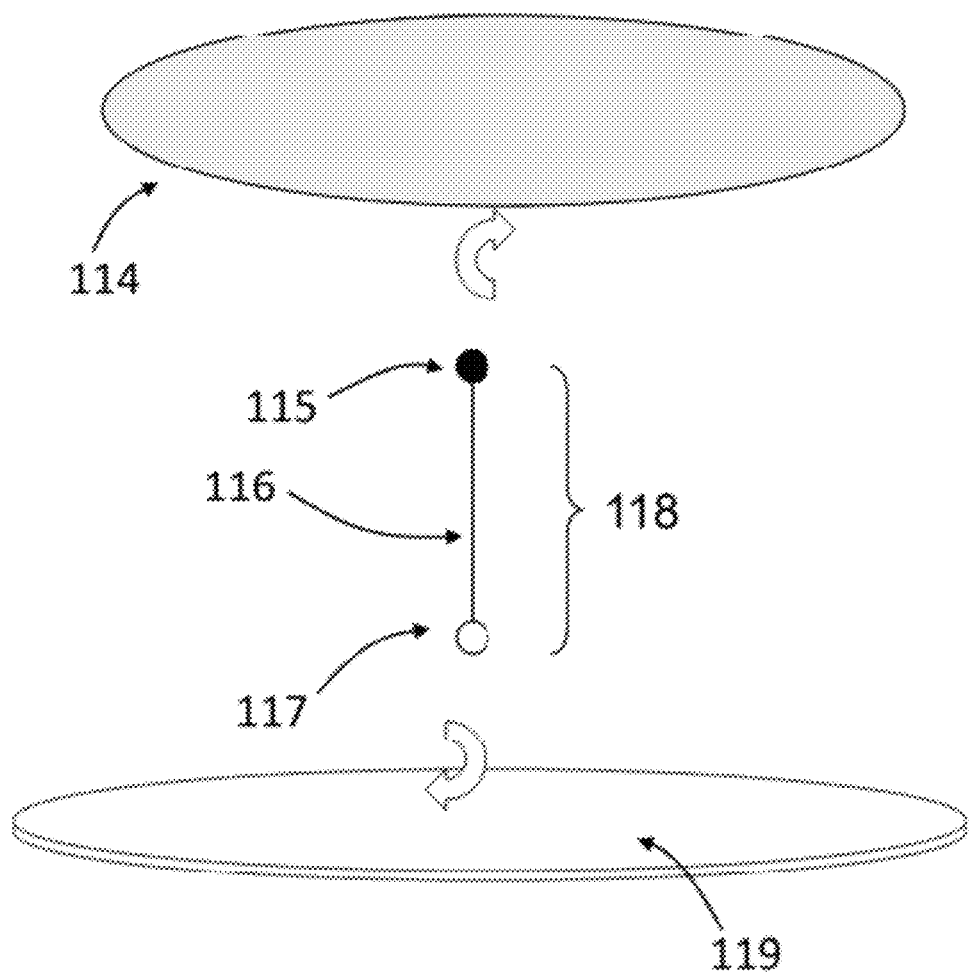

FIG. 29 shows according to an embodiment of the invention a heterobifunctional crosslinker 118 containing two end-groups 115, 117 joined by a spacer 116 that are used to covalently attach molecules, macromolecules, and biomolecules 114 to IPN hydrogel surfaces 119.

Figure 30:
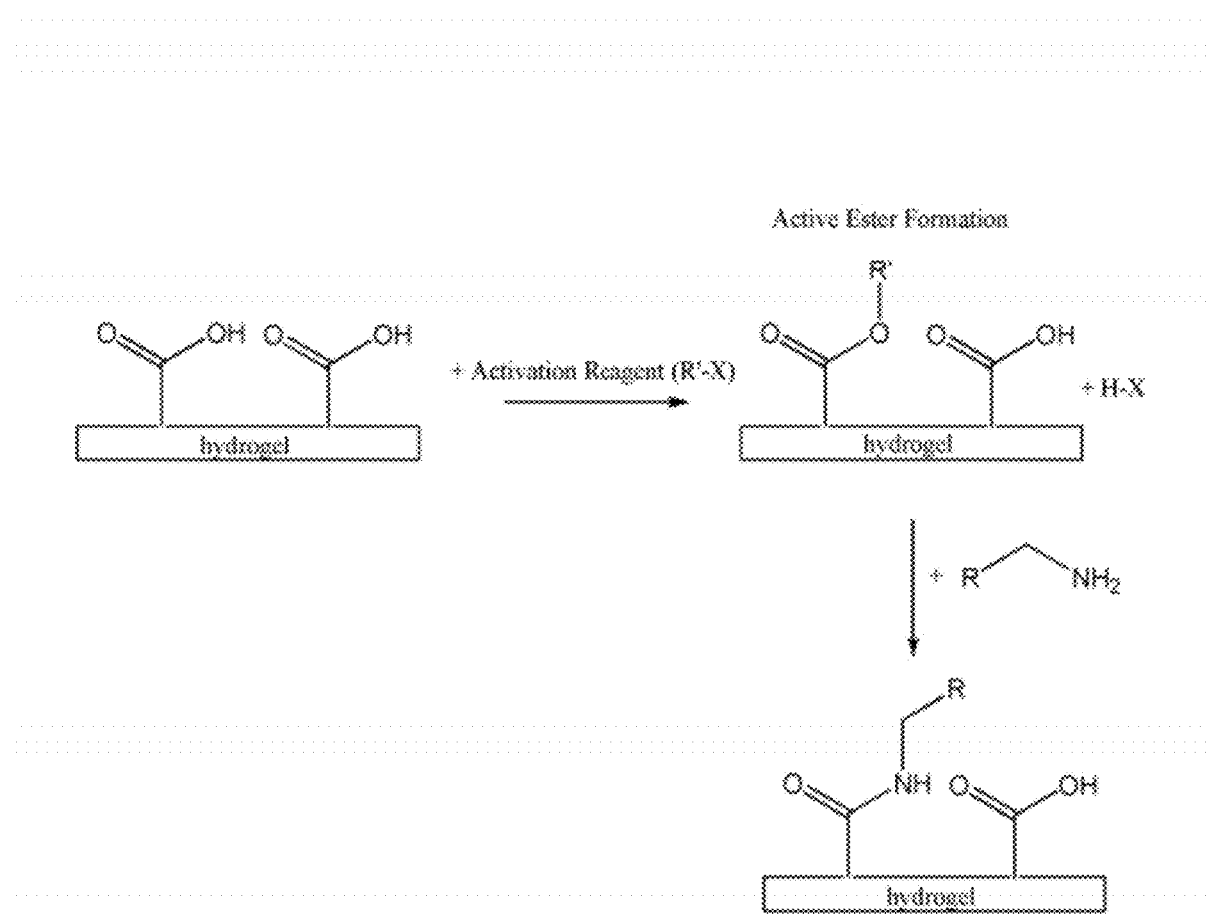

FIG. 30 shows according to an embodiment of the invention methods steps to attain a different surface chemistry at the bone-interface than that present in the bearing region. This approach involves activating the functional groups on the surface of the hydrogel followed by reaction of these activated function groups with amine-containing or hydroxyl-containing molecules, macromolecules, or biomolecules. In a preferred embodiment, the carboxylic acid groups on poly (acrylic acid) within an IPN are activated to form an active ester, which subsequently forms an acrylamide linkages when reacted with an amine-containing or hydroxyl-containing molecule, macromolecule, or biomolecules.

Figure 31:
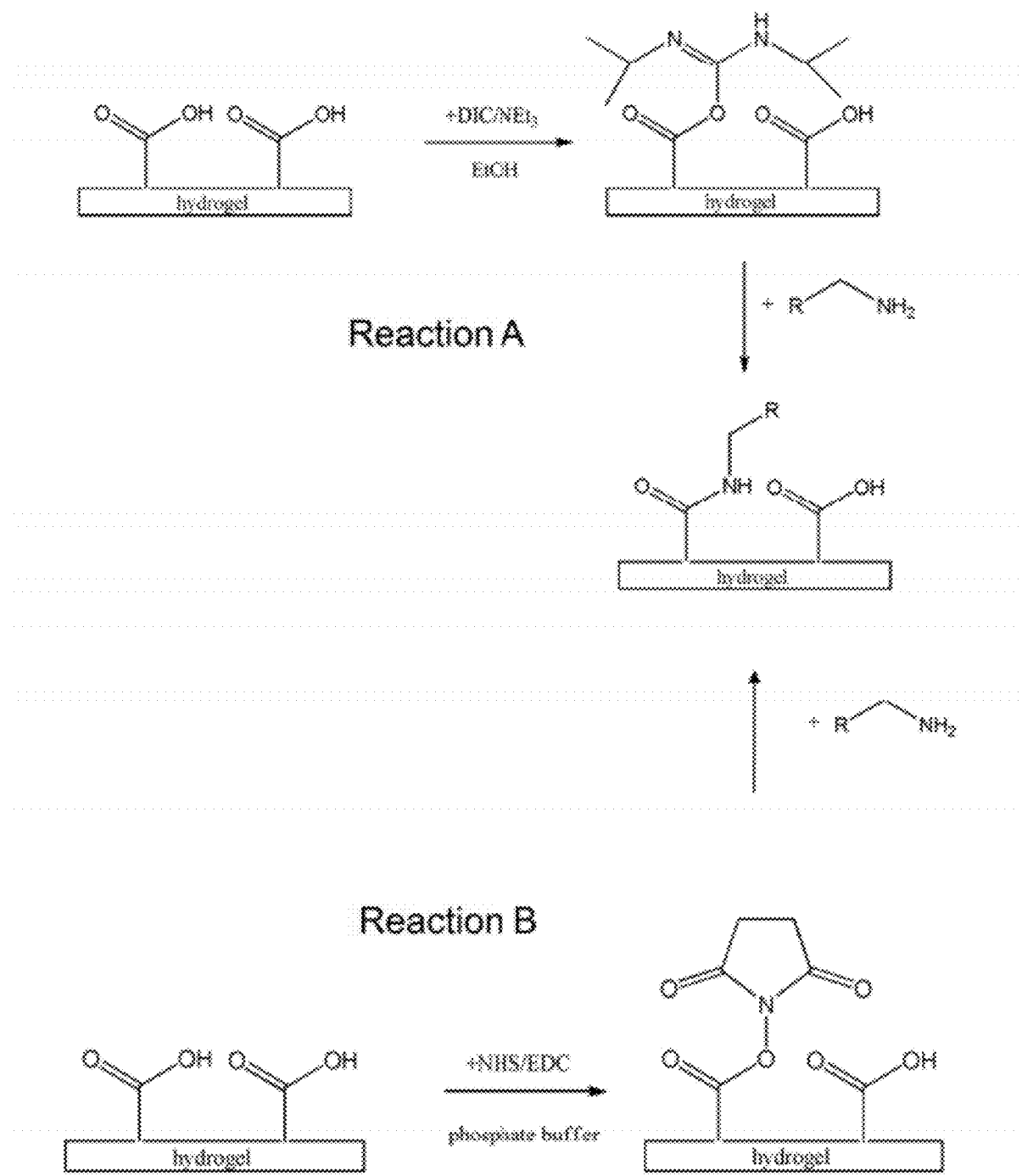

FIG. 31 shows specific examples of the method shown in FIG. 30 in which carboxylic acid functional groups on the hydrogel are activated and subsequently reacted with dopamine hydrochloride to yield a dopamine-conjugated surface. In Reaction A, a PEG/PAA hydrogel is soaked in a solution of dicyclohexylcarbodiimide and triethylamine in ethanol to activate the carboxylic acid groups present on the PAA. Subsequent reaction with dopamine hydrochloride and Triethylamine yields a dopamine-conjugated surface. In Reaction B, the PEG/PAA hydrogel is soaked in solution of N-hydroxysuccinimide and N-Ethyl-N'-(3-dimethylaminopropyl)carbodiimide in phosphate buffer to activate the carboxylic acids in PAA. Subsequent reaction with dopamine hydrochloride in DMF and triethylamine yields a dopamine-conjugated hydrogel surface.

Figure 32:
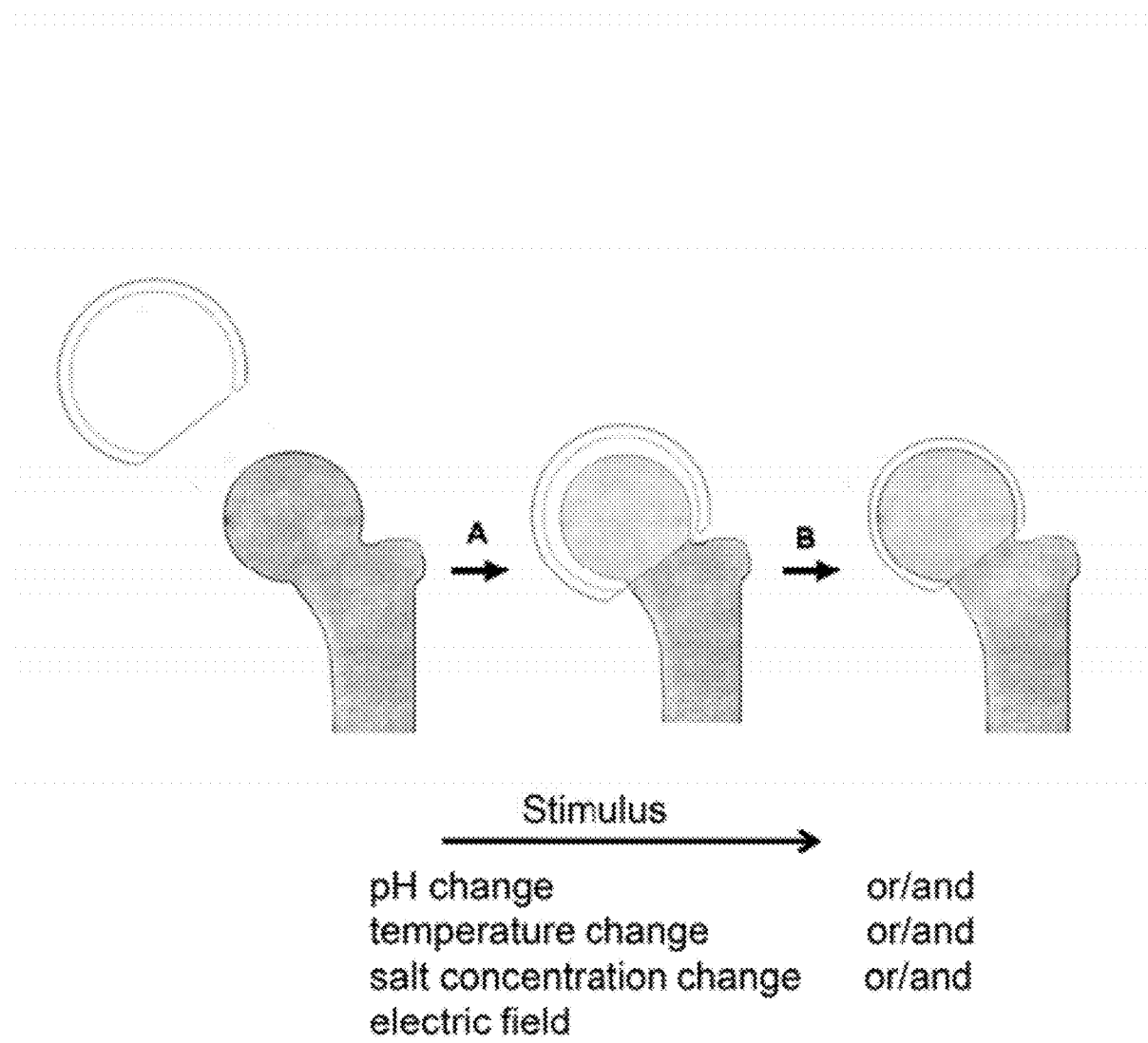

FIG. 32 shows an embodiment of the present invention in which an external stimulus such as a change in pH, salt concentration, electric field, or temperature causes the device, after (A) placement on the bone, to (B) shrink to conform to the contours of the convex-shaped bone it surrounds. Conversely, stimulated swelling can be achieved as a result of a change in pH, salt concentration, electric field, or temperature create an expansile effect on a concave joint surface. Stimulus-responsive polymers are incorporated into the bearing and/or bone-interfacing region of the device by the methods described in the present invention.

DETAILED DESCRIPTION

The present invention is a "biomimetic" bone-sparing hydrogel arthroplasty device (FIG. 1) that is designed to overcome the limitations of current joint replacement technologies. The device is comprised of flexible implants made from a novel cartilage-like hydrogel material that conform to the convex and concave surfaces of mammalian joints in either a total arthroplasty (both sides) or a hemi-arthroplasty (one side). The device has the high compressive strength and lubricity necessary to serve as a replacement for articular cartilage, intervertebral discs (lumbar or cervical), bursae, menisci, and labral structures in the body.

Figure 1:
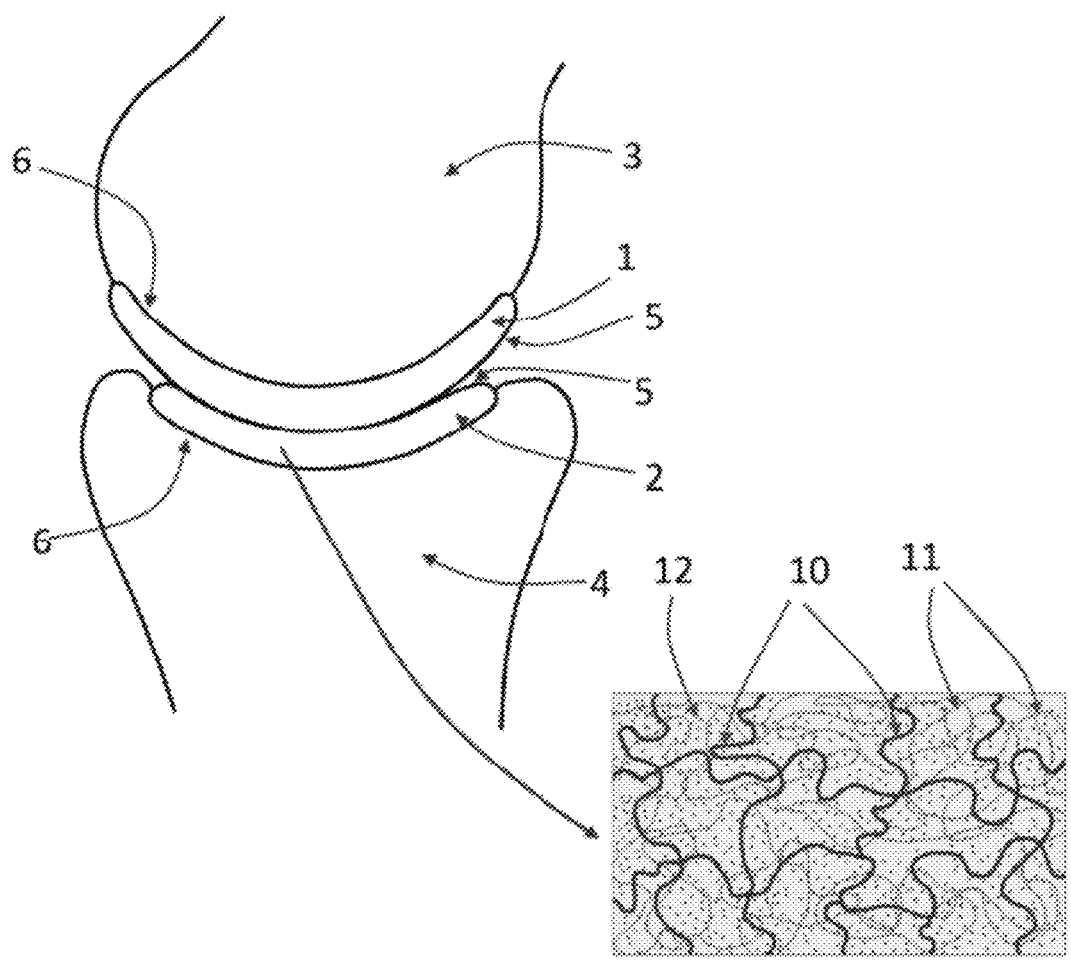
FIG. 1 shows a schematic of the device and anatomical structures according to an embodiment of the invention. The device has two components, one version 1 that is placed on the primarily convex bone side 3 of the joint and another version 2 that is placed on the primarily concave bone side 4. The bone interface regions 6 secure bone integration and adhesion. The bearing regions 5 possess a low coefficient of friction and allow for smooth relative sliding and rolling motion between the two components and are made of a strain-hardened interpenetrating polymer network hydrogel of a end-linked first network 10, an ionized second network 11, and an aqueous salt solution 12.

Illustrated in FIG. 1 are the key device and anatomical structures of the present invention in a typical diarthroidal joint. Most joints in the mammalian skeleton have a "male," primarily convex 3 cartilage surface and a "female," primarily concave cartilage surface 4. In this embodiment, the arthroplasty device is comprised of two components, one component (1) that fits over the primarily convex bone surface 3 and another component 2 that fits inside the primarily concave surface 4. Each component of the device holds a bearing surface 5 that comes to contact with the opposing bearing surface 5 of another other component. Each component of the device also holds a bone interfacing region 6 that enables the fixation of the device on the bone. Depending on the joint that the device is applied to, its shape can have a rather flat or a rather curved form, for example a device to replace the cartilage of the femoral head resembles a hemispherical cap while a device to replace the cartilage of the tibial plateau may resemble a shallow circular dish. In some cases, only one component of the device can be implanted as a hemi-arthroplasty so that it articulates with the natural cartilage that is left intact at the other side of the joint.

This device concept can be applied to nearly any joint in the body. For instance, the types of orthopaedic devices for which this invention is potentially useful includes total or partial replacement or resurfacing of the hip (femoral head and/or acetabulum), the knee (the tibial, femoral, and/or patellar aspect), shoulder, hands, fingers (e.g. carpometacarpal joint), feet, ankle, and toes. It is also useful in replacement or repair of intervertebral discs or facets. In the knee, the hydrogel can also serve as a meniscus replacement or a replacement material for the cartilage or bursae in any joint such the elbow or shoulder, or the labrum in joints such as the hip and shoulder.

This device strategy is guided by the limitations of current arthroplasty approaches, which are either highly bone-sacrificing or limited to only the repair of focal defects. The hydrogel device is put in place of damaged cartilage after the damaged cartilage has been removed by the surgeon—cartilage remains may need to be removed because subsequent overlying by the implant might cause unwanted conditions that lead to the differentiation of the remaining cartilage fibrous tissue.

Figure 2:
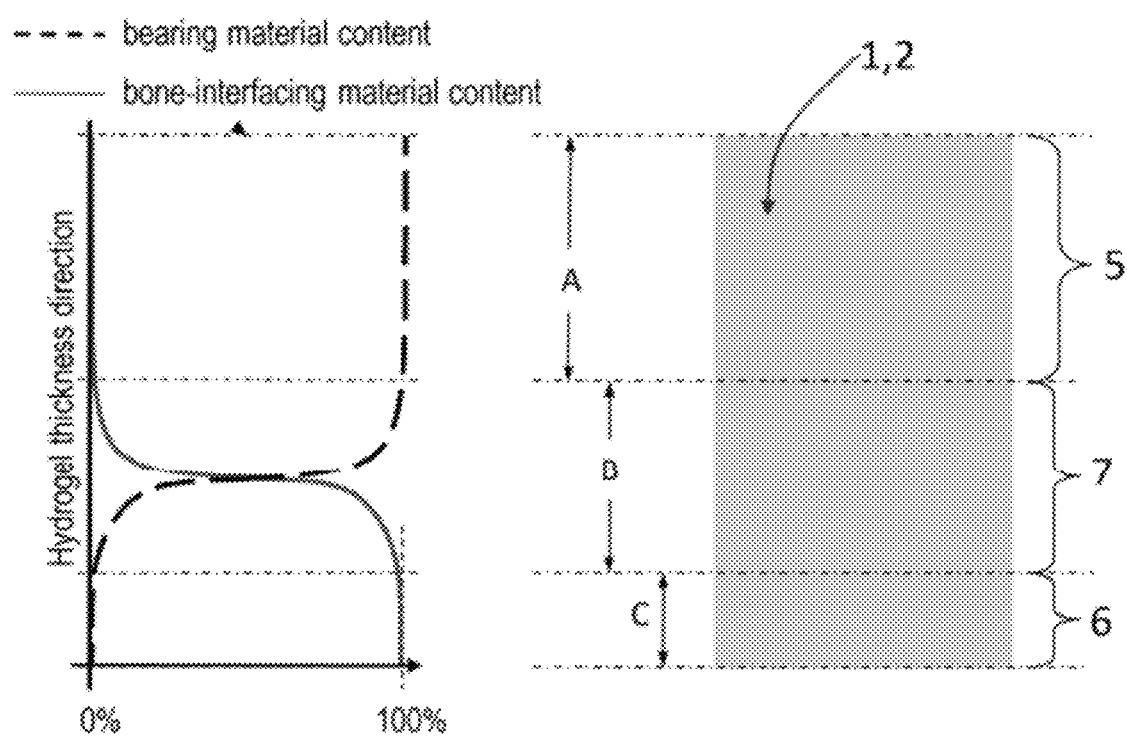
FIG. 2 shows a schematic of a cross-section of the device according to an embodiment of the invention, showing the bearing region 5 of thickness A and the bone-interfacing region 6 of thickness C that are integrated by a transition zone 7 of thickness B. The bearing 5 and bone-interfacing 6 regions could have the same or different materials, while dimensions A, B, and C vary based on the materials and device specifications.

The device itself is comprised of a "bearing" region 5 on one side, and a "bone-interfacing" region 6, in which the former articulates with another bearing surface (either another arthroplasty device such as the present invention or natural cartilage on an apposing joint surface) and the latter interacts with underlying bone. FIG. 2 depicts the cross-sectional area of the device's composition of matter, where one side contains the bearing region and the adjacent side contains the bone-interfacing region. The two regions can be comprised of the same material or different material. In one embodiment, the two regions are comprised of one and the same IPN hydrogel, while in another embodiment, the bearing region is comprised of an IPN hydrogel and the bone-interface region is comprised of another polymer that is integrated with the IPN hydrogel in such a way that there is a smooth transition zone 7 between the two materials. In one embodiment, the bearing region is made from an IPN hydrogel and the bone-interface region 6 of the hydrogel device 1,2 is made from a polymer or such as polyurethane, silicone rubber, derivatives, or combinations thereof (such as copolymers or interpenetrating networks with other polymers such as hydrogels with good mechanical properties that allow the device to stretch or compress in response to loads and be physically held in place by tensile or compressive stress on or by the adjacent bone. The relative thicknesses of the two regions can be varied such that the bearing region can make up either a large or small proportion of the volume of the device.

The device can be described as "biomimetic" (i.e. imitative of a natural cartilage) in that it is comprised of a material that mimics the structure and function of natural articular cartilage. While natural cartilage is composed of a highly negatively charged network of proteoglycans interpenetrating a neutral, rigid network of collagen with a water content of about 75%. In a preferred embodiment, the hydrogel is composed of a highly negatively charged network of poly(acrylic acid) interpenetrating a neutral, rigid hydrophilic, end-linked network of, for example, poly(ethylene glycol) macromonomers, with a water content of at least 35% and up to 90%, but preferably about 70%. Mimicking these structural details is believed to be critical to the formation of a stiff, yet highly lubricious bearing material that behaves like natural cartilage. Other combinations of hydrophilic, end-linked macromonomers and negatively charged second networks are possible. PEG and PAA are arguably the two most biocompatible, hydrophilic polymers available. For instance, PEG is known widely to be resistant to protein adsorption and PAA has recently been shown to have a protective role against macrophage activity in vivo. Although PEG and PAA are conventionally weak individually, we have developed a way to create "strain hardened" IPNs of these materials that mimic the high mechanical strength and elastic modulus, high water content, and low surface friction of natural cartilage. Like natural cartilage, the high mechanical strength and modulus of the hydrogel enable it to take up and distribute loads. At the same time, its high water content and low surface friction enable it to function as a slippery bearing surface, just like the nascent tissue.

Figure 3:
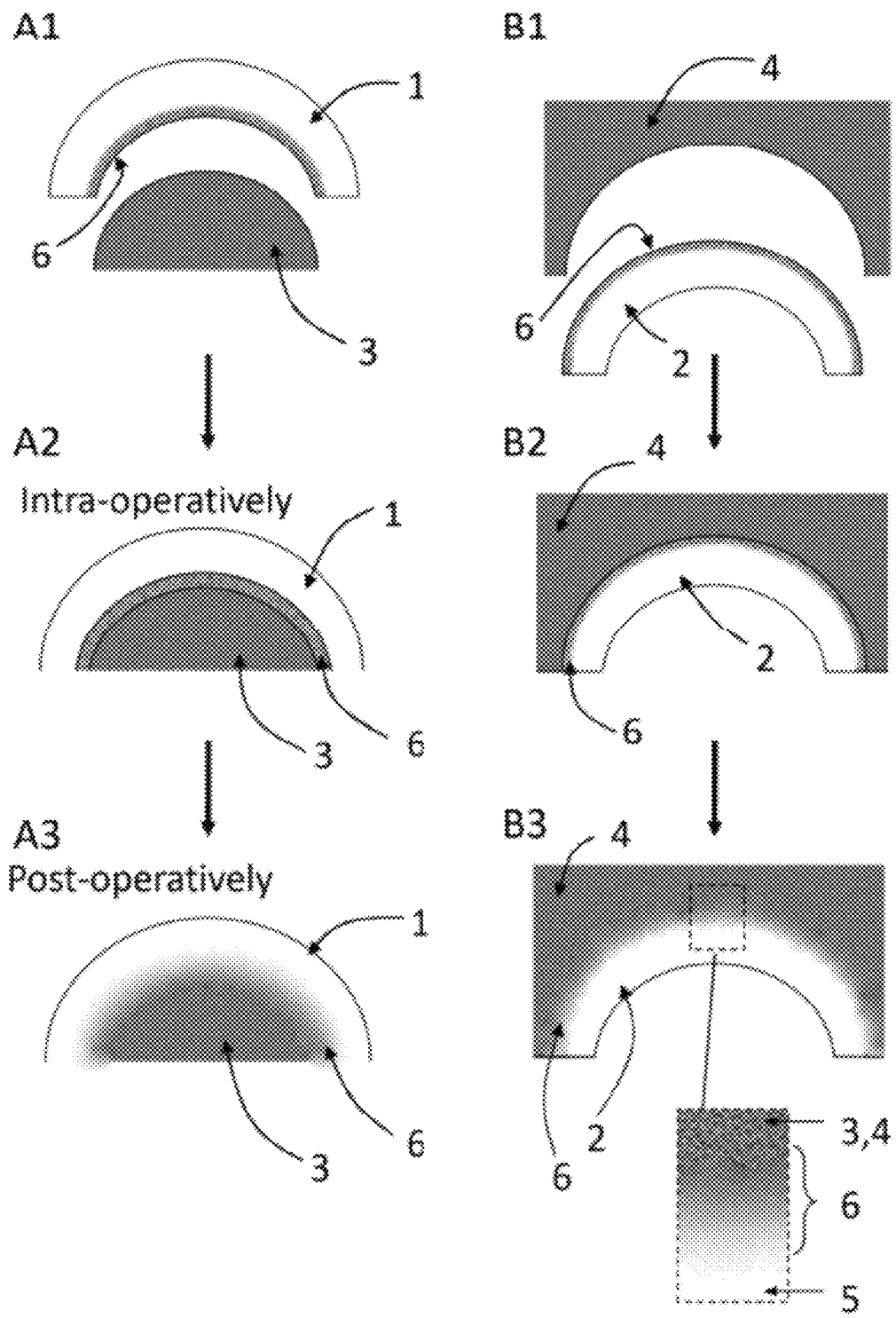
FIG. 3 shows a schematic of an anchoring strategy according to an embodiment of the invention for a convex (left column, A1-A3) and a concave (right column, B1-B3) joint surface. An adhesive layer could initially anchor the hydrogel to bone, but as it calcifies and allows new bone to grow in, hydroxyapatite binds to the bone interface region via the intervening scaffold to yield a calcified bone interface that mimics that found in natural cartilage.

Another innovative aspect of the present invention is the anchoring strategy (FIG. 3). A combination of physical, chemical, and biological means can be used to anchor the device to bone. To achieve physical anchoring, the bone interfacing region 6 of the hydrogel device 1, 2 is made to be rough and porous to match the micro-topography of either natural or artificially prepared (e.g., reamed) subchondral bone, which increases surface area and friction at this interface to enhance the mechanical interlocking of the bone by the device. In addition, the device is fabricated to conform to natural convexities and concavities of a given joint surface. As illustrated in FIG. 3.B1-B3 for the case of a concave joint structure 4 such as the acetabulum 4a, the device is fabricated as a cap 2a to mate perfectly with or is slightly oversized to create an expansive fit against the concavity. Also possible is the presence of a "lip" around the outer edge of the acetabulum component (4a) which creates a labrum-like structure around the outer groove of the socket, which would further aid in the positioning and anchoring of the device. As illustrated in FIG. 3.A1-A3 for the case of a convex joint structure 3 such as the femoral head, the hydrogel device 1a is fabricated as a cap to mate perfectly with or is slightly undersized to create a snug fit over the convexity. To supplement the aforementioned physical means to secure the hydrogel device 1 or 2, a number of strategies can be used. First, the bone interfacing region 6 encourages adhesion to the underlying bone, by methods that may include but are not limited to (a) a roughened surface, (b) a porous surface, (c) tethering the surface with cell adhesion-promoting biomolecules (such as cadherins or integrins) or biomolecules (e.g. collagen, Bone Morphogenetic Proteins (BMPs), bisphosphonates, and Osteogenic Proteins OP-1, or osteopontin), (d) by surface coating with osteoconductive substances (such as natural hydroxyapatite, calcium sulfates or purified collagen), or (e) addition of a bonding agent such as a cement or glue. Combinations of these are also possible. The anchoring process is depicted in the other plots in FIG. 3.

Figure 4:
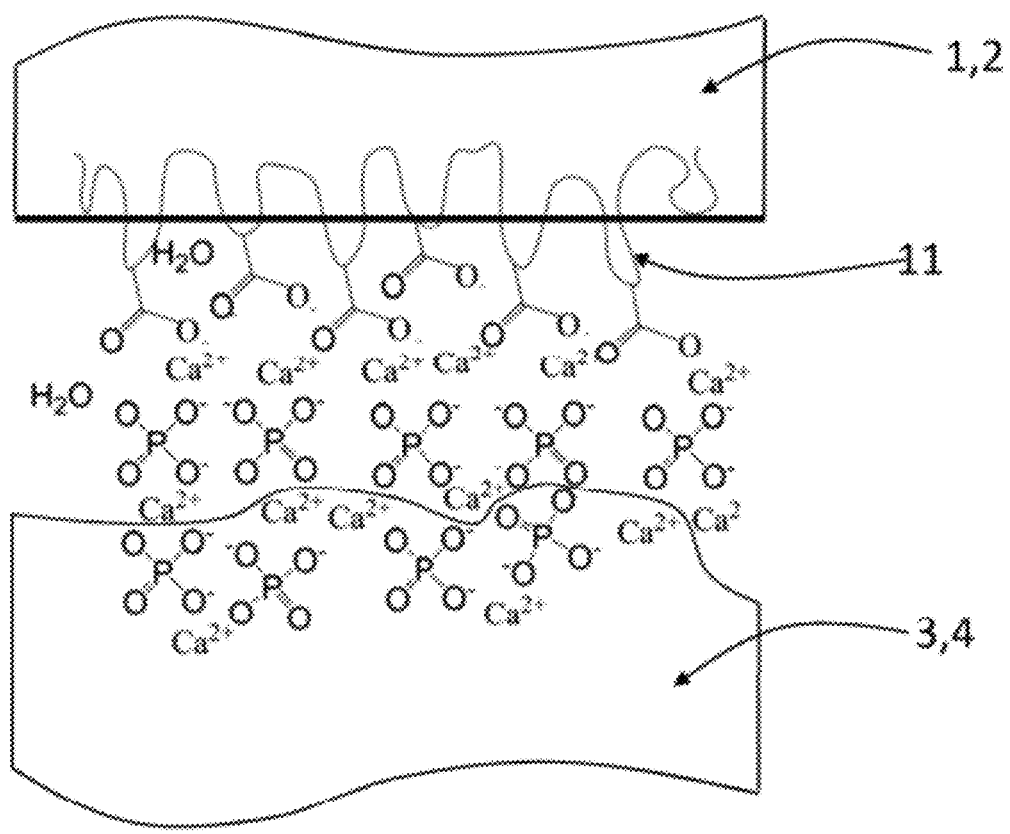
FIG. 4 shows according to an embodiment of the invention how the inorganic constituents of bone 3,4 (calcium and phosphate) can interact with the bone-interface region of an IPN hydrogel 1,2. In one embodiment, the carboxylic acid groups on the second network 11 (e.g. poly(acrylic acid)) interact and form complexes with the divalent calcium ions and negatively charged phosphate ions.

In one embodiment, the bone-interface region 6 of the device is prepared such that it interacts with the adjacent bone to allow for anchoring via osteointegration over time. In a version of this embodiment, illustrated in FIG. 4, the carboxylic acids in poly(acrylic acid) 11 in a PEG/PAA IPN bone-interface region 6 forms complexes with calcium and phosphates in the bone 3 as it is being remodeled. In another embodiment, the bone-interface region 6 comes precoated with calcium-containing inorganic constituents (e.g. tricalcium phosphate or/and hydroxyapatite) prior to implantation. In still another embodiment, another polymer material serving as the bone-interface region anchors the device through bone ingrowth and deposition and/or calcification. Thus, the biological means of anchoring is accomplished through a calcified layer. This sets the stage for continual bone growth and deposition within the pores of bone interface region and, in turn, anchorage of the device through a calcified, bio-artificial composite interface. Osteointegration of the device with underlying bone may enable it to move as one with the bone and function like cartilage within the joint and provide better adhesion through continuous bone remodeling.

The localized use of a curable adhesive that bonds the hydrogel to the bone provides a chemical means to attain robust, intraoperative anchoring. In one embodiment the adhesive can be a dental or orthopedic adhesive such as cement (e.g. zinc carbocylate cement), resin, glue or the like. This adhesive may be of one that provides firm bonding between the bearing region of the device and bone. The adhesive in cured form may be porous or non-porous and may be biodegradable or non-biodegradable. In the case of a degradable adhesive, the adhesive material is gradually broken down as new bone is formed that binds to the bone interface region. This degradation takes place over a period of about one to about twelve weeks after being implanted to coincide with the time it takes for new bone to form. In the case of a non-degradable adhesive, the adhesive itself binds and interdigitates with bone even as it is being remodeled.

In another embodiment, the bone interfacing region is made in part from a non-hydrogel polymer such as polyurethane, silicone rubber, or derivatives or combinations thereof (such as copolymers or interpenetrating networks with other polymers such as hydrogels) with good mechanical properties that allow the material to stretch or compress in response to loads and be physically held in place by tensile or compressive stress on or by the adjacent bone. Such a composite material would have a lubricious hydrogel (such as PEG/PAA) as the bearing region and the non-hydrogel polymer (such as polyurethane or silicone-based materials) as the bone-interface region.

Figure 5:
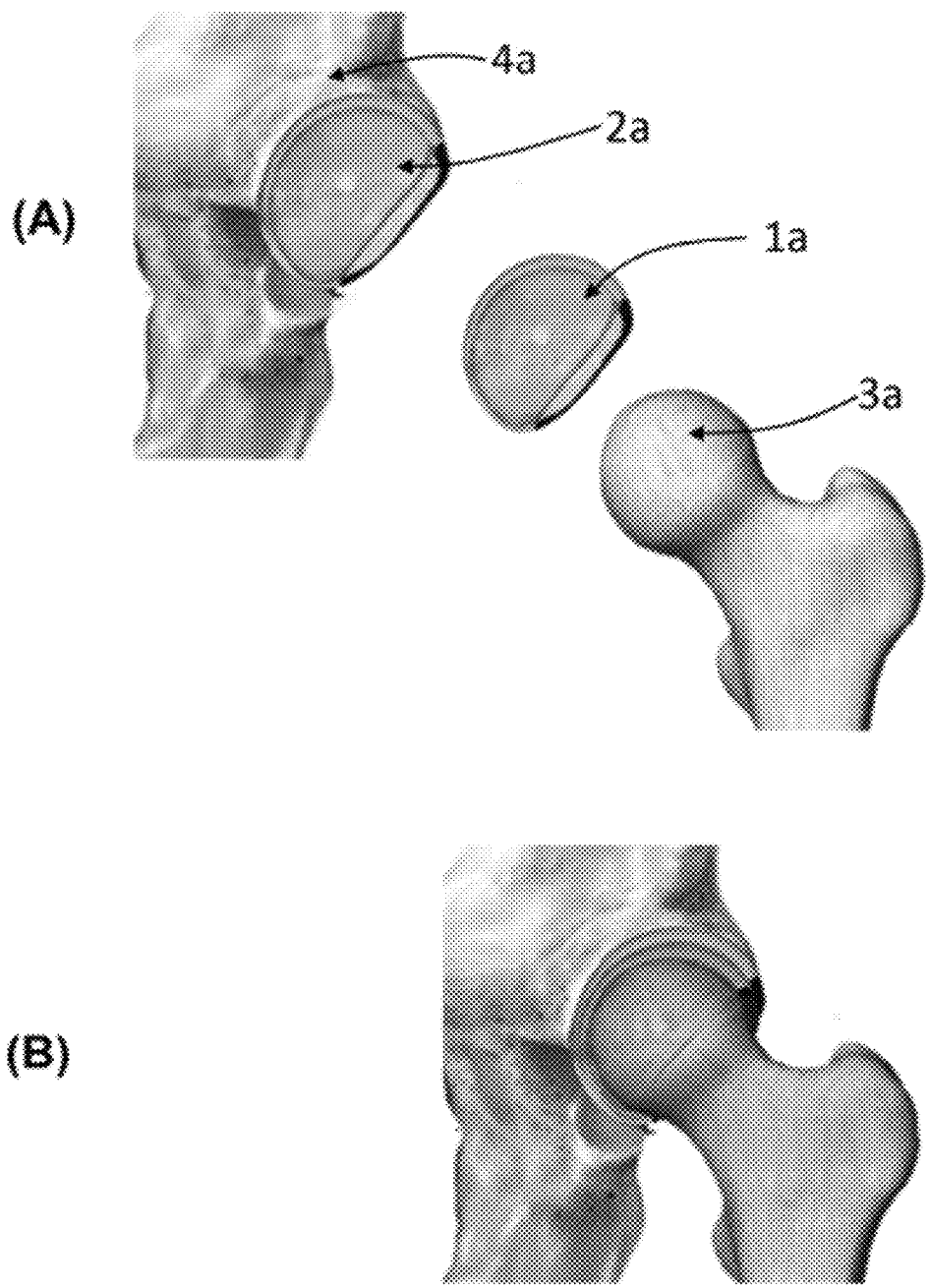
FIG. 5 shows according to an embodiment of the invention a hip arthroplasty procedure.
Figure 7:
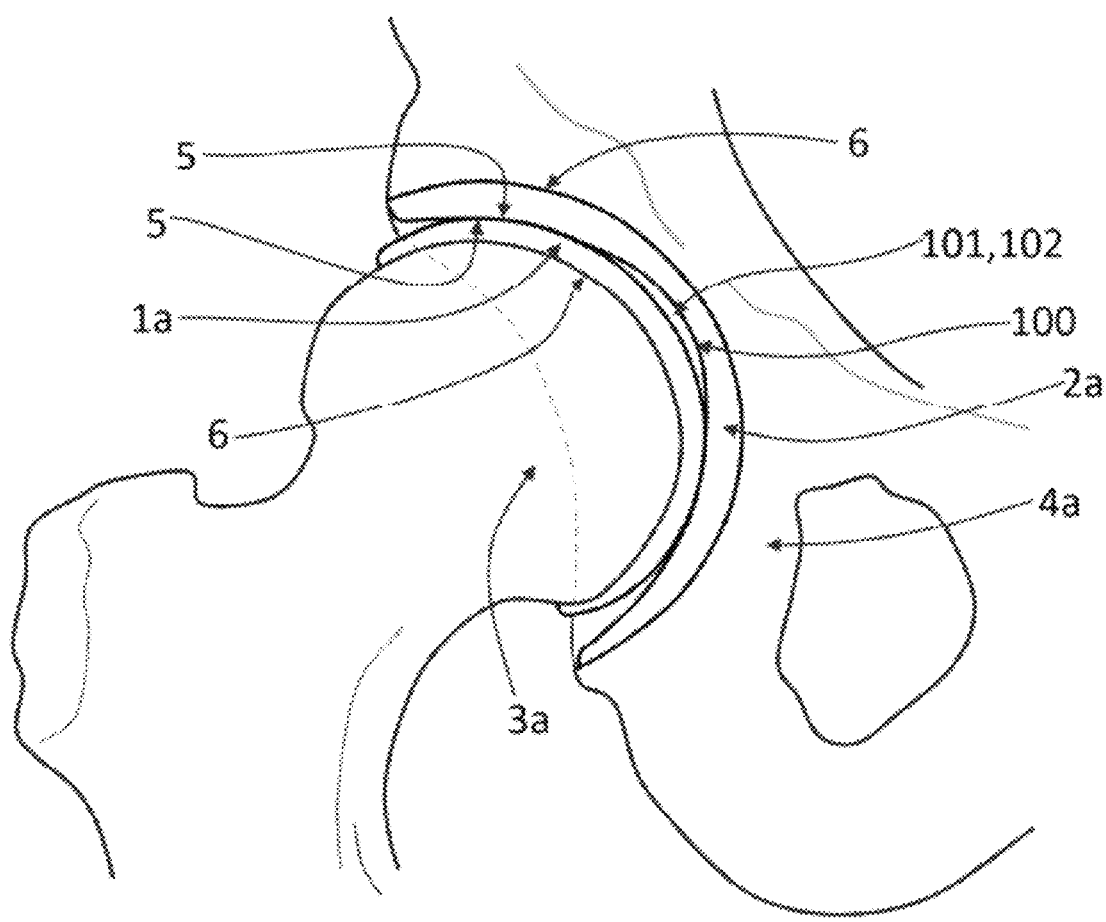

One embodiment of the present invention is application as a hip arthroplasty device. According to this embodiment, the arthroplasty hydrogel device is comprised of a femoral head component (1a) and an acetabulum component (2a) as shown in FIGS. 5, 6 and 7. Both components are comprised of a PEG/PAA interpenetrating network hydrogel with properties described in Table 1 and made by processes described hereafter.

TABLE 1

| PEG(3.4k)/PAA physical properties (averages) in PBS, pH 7.4 | |
| --- | --- |
| Water Content | 65% |
| Tensile Modulus | 12 MPa |
| Tensile Fracture Strength | 12 MPa |
| Aggregate Equilibrium Compressive Modulus | 1.6 MPa |
| Unconfined Compressive Strength | 18 MPa |
| Hydraulic Permeability (K) | $2.4 \times 10^{-14}$ m$^4$/N/sec |
| Dynamic Coefficient of Friction (gel-on-gel) | 0.05 |
| Linear Wear Rate (gel-on-gel) | ~0.75 microns/3.0M cycles |

The overall device geometry resembles the anatomy of natural cartilage. The femoral head component 1a holds a cap shape and is placed on the femoral head 3a bone after the later has been surgically reamed to remove damaged cartilage and the superficial bone layer. The femoral head component 1a bone interface region 6 has a radius of curvature that is slightly undersized compared to the radius of curvature of the femoral head bone 3a; the femoral component 1a can therefore be held in place by means of a tight fit around the femoral head. More specifically, and by analogy to latex condoms, the hydrogel device femoral head component 1a, being slightly undersized than the bone it is mounted onto, is pulled over the femoral head 3a and is held in place by tension generated by stretching of the hydrogel device 1a material. Because the femoral head component 1a material is stretchable, it can be stretched to fit over the femoral head. In one version of this embodiment, this cap shaped device 1a covers the bone 360 degrees on the lateral plane and as much as 200 degrees on the coronal plane. With the bone now occupying its inside space, the hydrogel device femoral head component 1a cannot completely return to its original dimensions, which causes the device 1a to "hug" the bone 3a it surrounds. The entire process can be facilitated by means of a retractor tool that could open up the device 1a opening.

The acetabulum component 2a is placed on the acetabulum bone 4a after the later has been surgically reamed to remove damaged cartilage and the superficial bone layer. The acetabulum hydrogel device component 2a holds a hemispherical shell shape and its bone interface region 6 has a radius of curvature that is slightly oversized compared to the radius of curvature of the acetabulum bone 4a socket; the acetabulum component 2a can be held in place by means of a tight press-fit inside the acetabulum 4a. The hydrogel device acetabulum component may also have a thickness profile that matches that of natural acetabular cartilage and is in the range of 1 mm-5 mm. The dimensions of the hydrogel devices are in accordance with the dimensions of the reamers employed by the surgeon. In addition, the edges of the devices may be rounded to prevent edge stress concentration.

A library of different size devices 1,2 may cover the wide range of joint sizes so that every patient would have a nearly perfect fit. At the time of surgery, the physician would choose and implant the device of the appropriate dimensions. The thickness can be adjusted, if necessary, to accommodate variations in joint surface area and/or the patient's weight, as well as joint conformity factors (i.e. the less conforming the joint, the higher the thickness needs be).

The bone interface region 6 of the device is porous with a pore size in the range of 10-1000 microns. The bone interface region is coated with a layer of soluble or insoluble hydroxyapatite that is chemically deposited by taking advantage of the bonds created due to the negative charges of the hydrogel and the calcium ions contained in the hydroxyapatite crystals as demonstrated in FIG. 4. Two to twelve weeks after implantation, the pores are filled with new bone tissue achieving an interdigitation of the bone and the hydrogel device.

The surface of the bearing region 5 of the femoral head component 1a has the same radius of curvature as the surface of the bearing region 5 of the acetabulum component 4a to achieve a dimensionally matched ball-in-socket mechanism and thus yield an even distribution of the contact stresses. Furthermore, the bearing region 6a of the acetabulum component may hold in its central region a depression 100 so that a chamber 101 is formed between the bearing sides of the acetabulum component 2a and the femoral component 1a. The chamber 101 is filled with fluid 102 at times of non bearing joint load, said fluid 102 gets pressurized once joint loads are applied since the chamber 101 is effectively sealed by the bearing region 5 surfaces; the pressurized fluid 102 can take up significant portions of the joint load.

The femoral component 1a may have a variable shell thickness profile as shown in FIG. 6B and in FIG. 7; the device thickness may vary from 1 mm to 5 mm. As such, the thickest shell region is at the superior side of the component 4, where the contact stresses are higher, while it gradually tapers out towards the edges 5 to increase range of motion of the joint and protect the device from impingement. The femoral component 1a may also hold a recess 103 on the superior side to accommodate any vessels that supply the femoral head bone. The acetabulum component 2a may hold a protrusion on its convex side that can fit inside the acetabular fossa, after the later is surgically reamed to remove any soft tissue; the said protrusion secures the initial placement of the hydrogel device acetabulum component 4a so that in combination with the continuous compression the joint is subjected to, implant migration is prevented.

Figure 8:
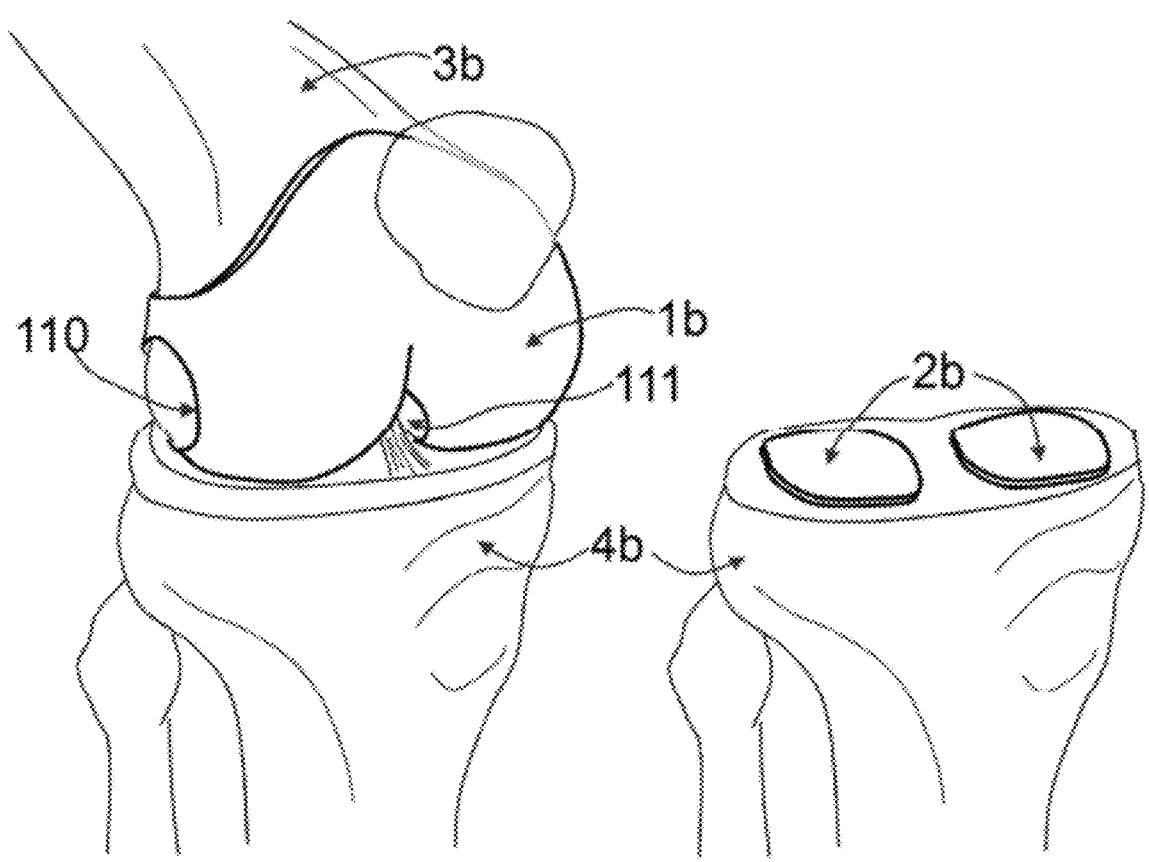
FIG. 8 shows according to an embodiment of the invention the hydrogel device applied to the knee. The distal femur device component 1b is placed on the distal femur bone 3b like a tight sock. The device holds openings or recesses for the ligaments; as such, a lateral opening 110 accommodates the lateral ligament while a central opening 111 accommodates the cruciate ligaments. The distal femur device component 1b is initially held in place by means of tight fit, further enhanced by a hydrogel stimulation process that is disclosed hereafter. The tibial plateau hydrogel device component 2b in this embodiment has two distinct parts, one for the lateral facet and one for the medial facet. The hydrogel device components hold a porous bone interfacing region 6 that allows for bone ingrowth to secure fixation.

In another embodiment, the hydrogel device can be applied to the knee joint. The device is comprised of a distal femur component 1b and a tibial plateau component 2b as shown in FIG. 8. The distal femur component 1b resembles in overall shape that of natural distal femur cartilage. It can be premade to have a generic adaptable shape or a patient specific geometry through reverse engineering methods. The component is placed on the bone like a sock. After the knee joint is exposed and damaged cartilage layer is surgically removed, the distal femur component 1b can be placed. Special openings in the device allow ligament insertion; as such a lateral opening 110 and a central opening 111 accommodate the lateral ligament and the cruciate ligaments respectively. The device can be tightly held in place by means of hydrogel stimulation and subsequent shrinking, either because of a change in the pH, a change in salt concentration or a change in the temperature, as also discussed in FIG. 32. For example, the component 1b can be equilibrated in a pH 9 environment pre-surgically which leads to increased swelling as discussed later in this application. Upon equilibrium with the body fluids and subsequent lowering of the pH, the component 1b will shrink, and thus conform to the particular geometry of the distal femur 3b. Alternatively the hydrogel can be pre-surgically equilibrated with a low (compared to body fluids) salt concentration solution, for example 0.01 M-0.05 M pre-surgically; upon implantation and salt equilibrium with the body's salt concentration, for example 0.15 M, the component conforms to the particular geometry of the distal femur 3b taking advantage of the material's sensitivity to salt concentration. In this way, an initial fixation of the component 1b is secured on the distal femur 3b.

Figure 9:
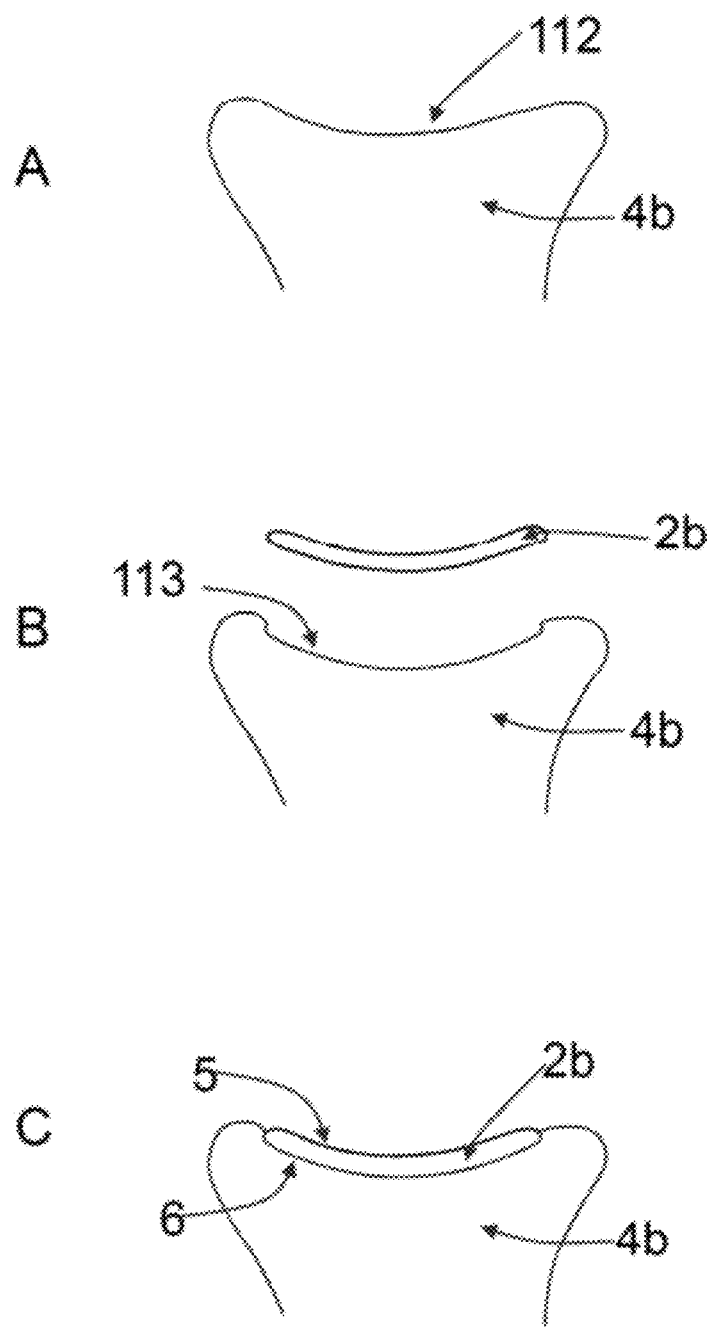
FIG. 9 shows according to an embodiment of the invention the hydrogel device application to the tibial plateau 4b.

The tibial plateau component 2b can have a curved disk shape and can be either unilateral or bilateral, that is it can cover both tibial plateau 4b facets, or simply either the lateral or the medial facet depending on the extent of the cartilage damage. One way the tibial plateau component 2b can be fixated in the bone is by surgically creating a depression 113 on the facet surface as shown in FIG. 9. The depression 113 can be made by either reaming or by locally crushing the subchondral bone 112, for example with a punch. The depression 113 has such dimensions so that the implant can be press fit in it; for example, a circular depression 113 can have a diameter that is one or two millimeters smaller than that of a circular component 2b.

The bone interfacing region 6 of both components is porous, with bone morphogenic proteins tethered on the surface to promote bone adhesion and/or ingrowth as discussed in FIG. 29. Microfractured or reamed bone exhibits regenerative properties; the interdigitation between bone and the hydrogel device takes up to twelve weeks post surgically.

Material Specifications

Current materials used in arthroplasty function well as mechanical "bearings" but suffer from key material property differences compared to natural cartilage. Because plastics, metals, and ceramics are not hydrated, they solely rely on serum/synovial fluid lubrication; the bearing function relies on the tolerances as well as on the surface roughness. Interfacial wear ultimately produces wear debris by means of abrasion. The products of wear are typically in particulate form (e.g. polyethylene particles) or in the form of ions (e.g., metal ions). Both of these have been shown to be promoters of inflammation in synovial joints and have been found to migrate into internal organs. Moreover, because metals are significantly stiffer than bone, they alter the stress transfer to the bone leading to bone resorption or fibrous tissue formation and ultimately loosening around the implants. One way that researchers have been exploring to avoid problems associated with conventional orthopaedic "hardware" is to use "software" (soft materials). One such approach available in the U.S. is "Carticel" autologous cartilage grafting. This has been shown to be effective in "filling in" focal defects in knee cartilage with regenerated cartilage from a patient's own chondrocytes. There are a number of other approaches under development that are related to tissue engineered cartilage, cell transplantation, and autologous grafting. To date, the simultaneous combination of cartilage-like stiffness and a hydrated, lubricious surface has been an elusive pair of properties to attain in materials engineering.

The present invention provides a hydrogel device 1 having an interpenetrating polymer network (IPN) hydrogel network based on a neutral cross-linked network of end-linked macromonomers 13 as the first network 10 and an ionized crosslinked polymer in the second network 11 depicted in FIG. 10. In one of the embodiments, the first network 10 is composed of end-linked poly(ethylene glycol) macromonomers with defined molecular weight. The second network 11 is, in contrast, a loosely crosslinked, ionizable network of poly(acrylic acid) (PAA). Furthermore, the hydrogel is comprised of an aqueous salt solution 12. This PEG/PAA IPN has high tensile strength, high compressive strength, and a low coefficient of friction when swollen in phosphate buffered saline at a pH of 7.4, as detailed in Table 1.

Homopolymer networks of PEG and PAA are both relatively fragile materials (the former is relatively brittle, the latter is highly compliant). However, the two polymers can form complexes through hydrogen bonds between the ether groups on PEG and the carboxyl groups on PAA. This interpolymer hydrogen bonding enhances their mutual miscibility in aqueous solution, which, in turn, yields optically clear, homogeneous polymer blends. By loosely cross-linking (instead of densely cross-linking) the ionizable network (PAA, pKa=4.7), large changes in its network configuration can be induced by changing the pH of the solvent without affecting the neutral PEG network. In salt-containing buffers of pH greater than 4.7, the PAA network becomes charged and swells; at a pH lower than 4.7, the PAA network is protonated and contracts.

FIG. 11 shows the steps required for synthesis of an IPN hydrogel according to the present invention. The starting material for the hydrogel is a solution of telechelic macromonomers 13 with functional end groups 15 dissolved in water 16. The telechelic macromonomers are polymerized (FIG. 11a) to form a first, water-swollen polymer network 10. Next, (FIG. 11b) hydrophilic, ionizable monomers 14 mixed with water 16 are added to the first polymer network 10 along with a photoinitiator and a crosslinking agent. The hydrophilic, ionizable monomers 14 are then photopolymerized and cross-linked in the presence of first polymer network 10 to form second polymer network 11 in the presence of the first 10. This results in formation of a water-swollen IPN hydrogel (FIG. 11b, right). The water-imbibed IPN is then immersed in a salt-containing solution 12 at pH 7.4 (FIG. 11c), and is swollen to equilibrium, yielding a simultaneous increase in both the water content and stiffness modulus of the IPN. The IPN on the right in FIG. 11c has a higher stiffness modulus compared to the IPN on the left. This increase in modulus as a result of strain (induced in this case by swelling) is believed to be caused by an increase in the number of physical crosslinks within the IPN. For the purpose of the present invention, "strain hardening" is defined as an increase in physical crosslinks (entanglements) and an increase in the stiffness modulus with applied swelling induced strain. The end material is an internally osmotically pre-stressed IPN that exhibits increased stiffness and strength.

FIG. 12Ai-iv shows according to an embodiment of the present invention method steps of how an IPN is prepared after monomers 17 are used to make the first network 10. Exposure to UV light in the presence of a photoinitiator and crosslinker (not shown) leads to polymerization and crosslinking to form a network 10, depicted by the transition from (i) to (ii). In (iii) to (iv), the first network is swollen with the second network precursor monomers 14, a crosslinking agent (not shown) and a photoinitiator (not shown). Exposure to UV light initiates polymerization and crosslinking of the second network 11 in the presence of the first 10 to form the IPN. FIG. 12B shows according to an embodiment of the present invention method steps of how an IPN is prepared after macromonomers 13 with reactive endgroups 15 are used to form a first network 10 in the presence of an existing second network 11 or linear macromolecules and/or biomacromolecules. A mixture of the first and second polymeric components is made, and then the telechelic macromonomers 13, 15 are reacted under UV light to form the first network 10 in the presence of the second 11. If the second network 11 is crosslinked chemically, then it is a fully interpenetrating network. If it is not (and only physically crosslinked), then it is a semi-interpenetrating network. FIG. 12C shows according to an embodiment of the present invention method steps of how an IPN is formed from a first network 10 based on monomers 17 and a second network 11 or linear macromolecules and/or biomacromolecules. A mixture of the monomers 17 and macromolecules is made, and then the monomers are reacted under UV light to form the first network in the presence of the second 11. If the second network 11 is crosslinked chemically, then it is a fully interpenetrating network. If it is not (and only physically crosslinked), then it is a semi-interpenetrating network.

In one embodiment of the present invention, grafted polymers are used to form the IPN. FIG. 16A shows a standard IPN according to the present invention, with first polymer network 10 and second polymer network 11. FIG. 16B shows an IPN in which first polymer network 10 is grafted with a hydrophilic polymer 29. Any of the aforementioned macromonomers, monomers, or combinations of macromonomers and monomers may be used to get a grafted structure. FIG. 16C shows an IPN in which the second polymer network 11 is grafted with another hydrophilic macromonomer 30. FIG. 16D shows an IPN in which first polymer network 10 is grafted with a hydrophilic monomer 29 and the second polymer network 11 is grafted with another hydrophilic macromonomer 30. The grafted networks are made by polymerizing aqueous mixtures of the two components in ratios that yield a network that is predominantly made from one polymer but has grafted chains of the second polymer.

Any hydrophilic telechelic macromonomer 13 may be used to form the first polymer network 10. In a preferred embodiment, preformed polyethylene glycol (PEG) macromonomers are used as the basis of the first network (10). PEG is biocompatible, soluble in aqueous solution, and can be synthesized to give a wide range of molecular weights and chemical structures. The hydroxyl end-groups of the bifunctional glycol can be modified into crosslinkable end-groups 15. End-group or side-group functionalities to these macromolecules and biomacromolecules may include, but are not limited to, acrylate (e.g. PEG-diacrylate), methacrylate, vinyl, allyl, N-vinyl sulfones, methacrylamide (e.g. PEG-dimethacrylamide), and acrylamide (e.g. PEG-diacrylamide). For instance, PEG macromonomers can be chemically modified with endgroups such as diacrylates, dimethacrylates, diallyl ethers, divinyls, diacrylamides, and dimethacrylamides. Examples of the end-group functionalization reactions to yield telechelic, crosslinkable PEG macromonomers are shown in FIGS. 13, 14, 15. These same endgroups can be added to other macromonomers, such as polycarbonate, poly (N-vinyl pyrrolidone), polyurethane, poly(vinyl alcohol), polysaccharides (e.g. dextran), biomacromolecules (e.g. collagen) and derivatives or combinations thereof. The first network 10 can also be copolymerized with any number of other polymers including but not limited to those based on acrylamide, hydroxyethyl acrylamide, N-isopropylacrylamide, polyurethane, 2-hydroxyethyl methacrylate, polycarbonate, 2-hydroxyethyl acrylate or derivatives thereof.

Preferably, the hydrophilic monomer 14 in the second network 11 is ionizable and anionic (capable of being negatively charged). In a preferred embodiment, poly(acrylic acid) (PAA) hydrogel is used as the second polymer network, formed from an aqueous solution of acrylic acid monomers. Other ionizable monomers include ones that contain negatively charged carboxylic acid or sulfonic acid groups, such as methacrylic acid, 2-acrylamido-2-methylpropanesulfonic acid, hyaluronic acid, heparin sulfate, chondroitin sulfate, and derivatives, or combinations thereof. The second network monomer 14 may also be positively charged or cationic. The hydrophilic monomer may also be non-ionic, such as acrylamide, methacrylamide, N-hydroxyethyl acrylamide, N-isopropylacrylamide, methylmethacrylate, N-vinyl pyrrolidone, 2-hydroxyethyl methacrylate, 2-hydroxyethyl acrylate or derivatives thereof. These can be copolymerized with less hydrophilic species such as methylmethacrylate or other more hydrophobic monomers or macromonomers. Crosslinked linear polymer chains (i.e. macromolecules) based on these monomers may also be used in the second network 11, as well as biomacromolecules such as proteins and polypeptides (e.g. collagen, hyaluronic acid, or chitosan).

Adding a photoinitiator to an aqueous solution of the end-linkable macromonomers 13 in water and exposing the solution to UV light results in the crosslinking of the PEG macromonomers, giving rise to a PEG hydrogel that serves as the first network 10. Polymerizing and crosslinking a second network 11 inside the first network will give rise to the IPN structure. Preparing IPN hydrogels through free-radical polymerization has the additional advantage that it enables the use of molds to form hydrogels of desired shape such as the ones depicted in FIGS. 7, 8. Preferably, the first polymer network contains at least 50%, more preferably at least 75%, most preferably at least 95% of the telechelic macromonomer 13, 15 by dry weight. Other solutions including buffers and organic solvents (or mixtures thereof) may also be used to dissolve the first network macromonomers 13 or second network monomers 14.

Any type compatible cross-linkers may be used to crosslink the second network 11 in the presence of any of the aforementioned first networks 10 such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene)bisacrylamide, derivatives, or combinations thereof. Any number of photoinitiators can also be used. These include, but are not limited to, 2-hydroxy-2-methyl-propiophenone and 2-hydroxy-1-[4-(2-hydroxyethoxy)phenyl]-2-methyl-1-propanone.

Examples of First Network Telechelic Macromonomers

Telechelic PEG macromonomers 13 with acrylate or methacrylate endgroups can be synthesized in the following manner. PEG was dried from Toluene, redissolved in THF (550 mL per 100 g) and kept under Nitrogen. Distilled triethylamine (2.5 eq per OH group) was added slowly to this solution. Acryloyl chloride (or methacryloyl chloride) was then added via a dropping funnel (diluted with THF) over 30 min at room temperature. The reaction (FIG. 13) was allowed to proceed overnight. Filtration was carried out to remove the formed salt. The volume of the solvent was reduced using a Rotavap, and precipitation was carried out in diethylether. As an alternative to extraction, filtration via a cellulose membrane has also been performed. The raw product was dried after precipitation from diethylether in a vacuum, then dissolved in MeOH and dried in a Rotavap. It is then dissolved in water and filtrated through a membrane, and was finally freeze-dried.

Networks have also been formed from PEG-diacrylamide. PEG-diol was converted to PEG-diacrylamide (FIG. 14) using the following procedure. PEG mol wt 3400 (100 g, 58.8 mmol —OH) was azeotropically distilled in 700 mL toluene under nitrogen and removing about 300 mL of toluene. The toluene was then evaporated completely and then the PEG re-dissolved in anhydrous tetrahydrofuran. Triethylamine was distilled prior to use. The solution was cooled in a room temperature bath under Nitrogen and then cooled in an ice bath. Anhydrous dichloromethane was added until the solution became clear (about 100 mL). Triethylamine (24.6 mL, 176.5 mmol) was then added dropwise with stirring, followed by the dropwise addition of 13.65 mmol mesyl chloride (176.5 mmol, an excess of 3 eq per OH endgroup). The reaction proceeded overnight under argon. The solution was filtered through paper under vacuum until clear, followed by precipitation in diethyl ether. The product was then collected by filtration and dried under vacuum. The PEG-dimesylate product was added to 400 mL 25% aqueous ammonia solution in a 1 L bottle. The lid was tightly closed and sealed with Parafilm, and the reaction was vigorously stirred for 4 days at room temperature. The lid was then removed and the ammonia allowed to evaporate for 3 days. The pH of the solution was raised to 13 with 1 N NaOH, and the solution was extracted with 100 mL dichloromethane. For the extraction with dichloromethane, NaCl was added to the water-phase (~5 g) and the water-phase was extracted several times with 150 mL of dichloromethane. The dichloromethane washes were combined and concentrated in vacuo. The product was precipitated in diethyl ether, and dried under vacuum. PEG-diamine mol wt 3400 (20 g, 11.76 mmol amine) was then azeotropically distilled in 400 mL of toluene under Nitrogen, removing about 100 mL of toluene. The toluene was then evaporated completely and then the PEG re-dissolved in anhydrous tetrahydrofuran. The solution was cooled in a room temperature bath under Nitrogen and then cooled in an ice bath. Triethylamine (2.46 mL, 17.64 mmol) was added dropwise with stirring, followed by the dropwise addition of 1.43 mL of acryloyl chloride (17.64 mmol). The reaction (FIG. 14) proceeded overnight in the dark under Nitrogen. The solution was then filtered through paper under vacuum until clear, followed by precipitation in diethyl ether. The product was collected by filtration and dried under vacuum. The product was then dissolved in 200 mL of deionized water, with 10 g of sodium chloride. The pH was adjusted to pH 6 with NaOH and extracted 3 times with 100 mL of dichloromethane (with some product remaining in the water phase as an emulsion). The dichloromethane washes were combined and the product was precipitated in diethyl ether, and dried under vacuum. Alternatively, PEG-diacrylamide has been precipitated from Diethylether once, redissolved in MeOH, dried from MeOH and then purified by centrifugal filtration in water through a cellulose membrane (MWCO: 3000). Freeze drying was used to attain the desired product.

PEG macromonomers containing diols have also been converted into allyl ethers. Difunctional allyl ether macromonomers were synthesized from PEG using the following procedure (FIG. 15). Fresh anhydrous tetrahydrofuran (THF) (100 mL) was added to every 10 g of PEG. This mixture was gently heated until the PEG dissolved and then cooled in an ice bath before sodium hydride was slowly added in multiple portions (1.05 molar equiv. NaH for the PEG ReOH groups). After the release of H2 gas ceased, the system was purged with argon and allyl chloride or allyl bromide (1.1 molar equiv. per PEG OH-group, diluted 1:10 in THF) was added dropwise using an addition funnel, after which the reaction mixture (FIG. 15) was transferred to an 85 degrees Celsius oil bath and refluxed overnight. Vacuum filtration was used to remove the sodium bromide side products and rotary evaporation was used to reduce the concentration of THF before the PEG-allyl ether products were precipitated from solution using iced diethyl ether (10:1 v:v diethyl ether:THF solution).

EXAMPLES

The following description refers to an exemplary embodiment of a strain-hardened interpenetrating polymer network hydrogel with PEG as a first network 10 polymer and PAA as a second network 11 polymer. The IPN hydrogel is synthesized by a (two-step) sequential network formation technique based on UV initiated free radical polymerization. A precursor solution for the first network is made of purified, telechelic PEG dissolved at a typical concentration of 50% w/v in phosphate buffered saline (PBS) solution, water, or an organic solvent with either 2-hydroxy-2-methyl-propiophenone or 2-hydroxy-1-[4-(2-hydroxyethoxy)phenyl]-2-methyl-1-propanone as the UV sensitive free radical initiator. The types of telechelic PEG macromonomers used were PEG-diacrylate, PEG-dimethacrylate, PEG-diacrylamide, and PEG-diallyl ether. In other embodiments, either network can be synthesized by free radical polymerization initiated by other means, such as thermal-initiation and other chemistries not involving the use of ultraviolet light. In the case of UV polymerization, the precursor solution is cast in a transparent mold and reacts under a UV light source at room temperature. Upon exposure, the precursor solution undergoes a free-radical induced gelation and becomes insoluble in water. The mold is fabricated in such a way that yields hydrogels at equilibrium swelling desired dimensions.

To incorporate the second network 11, the PEG-based hydrogel is immersed in the second monomer 14 solution, such as an aqueous solution of (10-100% v/v) acrylic acid containing a photo-initiator and a cross-linker, from 0.1% to 10% by volume triethylene glycol dimethacrylate (TEGDMA), triethylene glycol divinyl ether, N,N-methylene bisacrylamide, or N,N'-(1,2-dihydroxyethylene)bisacrylamide, for 24 hours at room temperature. The swollen gel is then exposed to the UV source and the second network 11 is polymerized and crosslinked inside the first network 10 to form an IPN structure in which the degree of crosslinking in the second network is less than that of the first network. Preferably, the molar ratio of the first network telechelic macromonomer to the second network monomer ranges from about 1:1 to about 1:5000. Also preferably, the weight ratio of the first network to the second network is in the range of about 10:1 to about 1:10. In another embodiment of the present invention, the IPNs have a molar ratio of the second monomer ingredient to the first macromonomer ingredient higher than 100:1.

Key characteristics of hydrogels such as optical clarity, water content, flexibility, and mechanical strength can be controlled by changing various factors such as the second monomer type, monomer concentration, molecular weight and UV exposure time. The experimental focus of the ensuing section is on the swelling induced strain hardening observed in this system by testing how it manifests through uniaxial tensile tests under various conditions of first 10 and second 11 network crosslinking and swelling. Swelling data were used to calculate the equilibrium water and polymer content of the networks, which were correlated with stiffness modulus, true stress-at-break, and true strain-at-break. The results indicate that strain hardening is derived from physical entanglements between the PEG and PAA networks that are intensified by bulk deformation. Under conditions that promote hydrogen bonding (when the pH is at or below 4.7, the pKa of PAA), these entanglements are reinforced by interpolymer complexes between PEG and PAA, leading to an increase in the fracture strength of the IPN. Under conditions that promote ionization of PAA (when the pH is above 4.7 and salt is added), increased steric interactions (i.e. physical crosslinks) between the swelling PAA network and static, telechelic PEG macromonomer network lead to an increase in the stiffness modulus.

In particular embodiment, an array of IPNs with varying molecular weights of PEG in the first network 10 and varying PAA polymer content in the second network 11 were fabricated based on diacrylate crosslinking in the first network 10 and triethylene glycol dimethacrylate crosslinking in the second network 11. All hydrogels were formed by photopolymerization with UV light using the photoinitiator, 2-hydroxy-2-methyl-propiophenone at a concentration of 1% v/v with respect to the monomer 14 or macromonomer 15. Before the IPNs were prepared, single network hydrogels based on PEG and PAA were synthesized separately to confirm the formation of gels of each composition and to investigate the physical properties of the single networks. For the PEG single network, a range of hydrogels that varied between 275 and 14000 for the MW of the PEG macromonomer was synthesized. It was found that low MW PEG macromonomers gave rise to gels that were brittle, whereas the hydrogels made from higher molecular weight PEG-DA (3400) were transparent and flexible when swollen in deionized water. Based on these results, a range of different MWs of PEG (3400, 4600, 8000, and 14000) were chosen as macromonomers for the first hydrogel network. A series of IPNs was synthesized by polymerizing and crosslinking a PAA network within each type of PEG network. The resultant IPNs had significantly better mechanical properties compared with single network hydrogels.

To explore the effect of the molecular weight of the telechelic PEG-DA macromonomer on IPN mechanical strength, PEG chains with MWs 3400 Da, 4600 Da, 8000 Da, and 14000 Da were used in the first network while keeping the acrylic acid polymerization conditions constant (50% v/v in deionized water with 1% v/v crosslinker and 1% v/v photoinitiator with respect to the monomer). The resulting IPNs were characterized in terms of their water content, tensile properties, and mesh size in deionized water. Changing the MW of the PEG-DA macromonomer led to a change in the moduli of the PEG-DA single networks, as shown in Table 2. This effect was magnified in the PEG/PAA IPNs, where the IPNs initial and final moduli get increasingly higher as the networks are prepared from lower molecular weight PEG-DA macromonomers. Of note, there was little increase in strength when the PEG MW is increased above 8000, indicating that a contrast between the molecular weight between crosslinks of the PEG and PAA networks is important for strength enhancement. Moreover, the molecular weight of the PEG macromonomer was strongly correlated to the critical strain ($\epsilon_{crit}$) at which the stress-strain curve makes the transition from the initial modulus to the strain-hardened final modulus. The $\epsilon_{crit}$ was smaller for the IPNs prepared from lower MW PEG macromonomers, meaning that these networks strain-harden more rapidly in response to deformation.

ionization state of the PAA network. Since the equilibrium swelling of PAA is sensitive to variations in pH, a change in

TABLE 2

Physical properties of PEG/PAA IPNs under different PEG crosslinking and swelling conditions

| specimen | swelling solution | WC** (%) | q*** | $\sigma_{max}$ (MPa) | $\epsilon_{break}$ | $E_o$ (MPa) | $E_f$ (MPa) |
|---|---|---|---|---|---|---|---|
| PEG(3.4k) | dH$_2$0 | 79.3 ± 2.1 | 4.6 | 0.33 ± 0.09 | 0.23 ± 0.089 | 1.49 ± 0.05 | — |
| PEG(3.4k)/PAA | dH$_2$0 | 56.3 ± 3.3 | 2.3 | 8.94 ± 0.97 | 0.62 ± 0.03 | 2.32 ± 0.09 | 36.2 ± 2.9 |
| PEG(3.4k)/PAA | pH 7.4, I = 0.15 | 68.7 ± 1.6 | 3.2 | 8.94 ± 1.08 | 0.50 ± 0.11 | 3.58 ± 0.001 | |
| PEG(4.6k) | dH$_2$0 | 84.5 ± 0.4 | 6.5 | 0.65 ± 0.14 | 0.67 ± 0.13 | 0.85 ± .002 | — |
| PEG(4.6k)/PAA | dH$_2$0 | 57.0 ± 0.6 | 2.3 | 5.98 ± 2.31 | 0.77 ± 0.11 | 1.15 ± 0.20 | 20.5 ± 5.0 |
| PEG(4.6k)/PAA | pH 7.4, I = 0.15 | 77.0 ± 1.2 | 3.0 | 6.28 ± 1.98 | 0.62 ± 0.07 | 3.50 ± 0.28 | 15.1 ± 2.0 |
| PEG(8.0k) | dH$_2$0 | 90.5 ± 1.2 | 10.5 | 0.27 ± 0.04 | 0.63 ± 0.04 | 0.20 ± 0.05 | — |
| PEG(8.0k)/PAA | dH$_2$0 | 80.2 ± 1.5 | 5.1 | 4.83 ± 1.09 | 1.18 ± 0.09 | 0.38 ± 0.04 | 11.4 ± 0.79 |
| PEG(8.0k)/PAA | pH 7.4, I = 0.15 | 90.9 ± 0.1 | 11.0 | 1.98 ± 0.24 | 0.75 ± 0.05 | 0.53 ± 0.12 | 6.1 ± 0.01 |
| PEG(8.0k)/PAA | pH 7.4, I = 0.30 | 89.5 ± 0.4 | 9.5 | 1.74 ± 0.20 | 0.73 ± 0.05 | 0.49 ± 0.07 | 5.25 ± 0.01 |
| PEG(8.0k)/PAA | pH 7.4, I = 0.75 | 83.1 ± 0.6 | 5.9 | 2.15 ± 0.40 | 0.80 ± 0.07 | 0.47 ± 0.03 | 6.6 ± 0.01 |
| PEG(8.0k)/PAA | pH 7.4 I = 1.5 | 77.7 ± 0.2 | 4.5 | 3.16 ± 0.97 | 0.84 ± 0.09 | 0.53 ± 0.11 | 8.98 ± 0.01 |
| PEG(8.0k)/PAA | pH 3, I = 0.05 | 76.5 ± 2.1 | 4.3 | 8.18 ± 1.76 | 1.20 ± 0.01 | 0.52 ± 0.03 | 24.0 ± 3.6 |
| PEG(8.0k)/PAA | pH 4, I = 0.05 | 86.4 ± 1.5 | 7.4 | 5.48 ± 1.44 | 1.01 ± 0.12 | 0.56 ± 0.04 | 15.1 ± 1.8 |
| PEG(8.0k)/PAA | pH 5, I = 0.05 | 94.5 ± 1.1 | 18.2 | 1.26 ± 0.05 | 0.63 ± 0.02 | 0.62 ± 0.08 | 3.99 ± 0.29 |
| PEG(8.0k)/PAA | pH 6, I = 0.05 | 95.6 ± 1.0 | 22.7 | 0.86 ± 0.15 | 0.53 ± 0.02 | 0.68 ± 0.005 | 3.10 ± 0.30 |
| PEG(14.0k) | dH$_2$0 | 95.1 ± 1.2 | 20.4 | 0.07 ± 0.007 | 0.70 ± 0.02 | 0.062 ± 0.005 | — |
| PEG(14.0k)/PAA | dH$_2$0 | 84.3 ± 1.7 | 6.4 | 0.25 ± 0.05 | 0.82 ± 0.07 | 0.18 ± 0.01 | 0.57 ± 0.17 |
| PAA | dH$_2$0 | 90 ± 1.7 | 10.0 | 0.14 ± 0.03 | 0.89 ± 0.09 | 0.14 ± 0.03 | — |
| PAA | pH 7.4, I* = 0.15 | 95.5 ± 1.7 | 22.2 | 0.07 ± 0.01 | 0.65 ± 0.10 | 0.050 ± 0.001 | — |
| PAA | pH 3, I = 0.05 | 80.4 ± 1.0 | 5.1 | 0.38 ± 0.08 | 1.23 ± 0.05 | 0.09 ± 0.01 | — |
| PAA | pH 4, I = 0.05 | 90.0 ± 0.7 | 10.0 | 0.35 ± 0.11 | 1.19 ± 0.15 | 0.090 ± 0.001 | — |
| PAA | pH 5, I = 0.05 | 96.2 ± 0.2 | 26.3 | 0.04 ± 0.007 | 0.50 ± 0.11 | 0.05 ± 0.008 | — |
| PAA | pH 6, I = 0.05 | 96.6 ± 0.1 | 30.3 | 0.05 ± 0.01 | 0.66 ± 0.08 | 0.050 ± 0.002 | — |

*I = ionic strength
**water content = (swollen weight − dry weight)/(swollen weight)
***average swelling ratio = (swollen weight)/(dry weight)

The significance of forming an interpenetrating structure rather than a copolymeric structure was explored by synthesizing a PEG-co-PAA copolymer hydrogel and testing its tensile properties. Its stress-strain profile was then juxtaposed with those of the IPN and the PEG and PAA single networks. In FIG. 18A, a representative true stress ($\sigma_{true}$) versus true strain ($\epsilon_{true}$) profile of the PEG(8.0 k)/PAA IPN is compared to those of the PEG(8.0 k)-PAA copolymer and their component PEG(8.0 k) and PAA networks. The IPN exhibits strain-hardening behavior with a stress-at-break that is greater than four times that of the copolymer and single network. However, since each of the materials tested has different water content, the stress data were normalized on the basis of polymer content to determine the true stress per unit polymer in each hydrogel. In FIG. 18B, the true stress per unit polymer ($\sigma_{true}$ per unit polymer) is plotted against true strain for PEG (8.0 k)-DA, PAA, PEG(8.0 k)/PAA, and the PEG(8.0 k)-PAA copolymer. The initial moduli of the PEG single network, the copolymer, and IPN are identical ($E_o$ per unit polymer=0.91 MPa), while that of the PAA single network is lower ($E_o$ per unit polymer=0.55 MPa). Near the break point of the PEG network, $\epsilon_{true}$~0.6, the copolymer continues to be elongated with a modulus that is intermediate between the PEG and PAA single networks, of which it is equally composed by weight. Ultimately, it fails at a strain that is also intermediate between the $\epsilon_{break}$ values of the two single networks. In stark contrast, just beyond the failure point of the PEG network, the PEG/PAA IPN manifests a dramatic strain hardening effect in which its modulus increases by 30 fold, and breaks at $\epsilon_{true}$~1.0 under a mean maximum stress per unit solid of 10.6 MPa. Without normalization for polymer content, $\sigma_{break}$ for the IPN (20% solid) and copolymer (51% solid) are 3.5 MPa and 0.75 MPa, respectively.

To explore the role of interpolymer hydrogen bonding, the pH of the hydrogel swelling liquid was varied to change the the pH was expected to have an impact on the mechanical properties of PEG/PAA IPNs. After synthesis, the water-swollen PAA single networks and PEG(8.0 k)/PAA IPNs were placed in buffers of pH 3-6 and constant ionic strength (I) of 0.05. In both the PAA network and the IPN, the equilibrium water content increased as the pH was increased from 3 to 6 (Table 2). In the case of the PAA networks, those at pH 3 and 4 were moderately swollen, while those at pH 5 or 6 were highly swollen due to ionization of PAA above its pKa (4.7). The IPNs also achieved different levels of swelling depending on the pH; those at pH 3 and 4 were moderately swollen, while those at pH 5 or 6 were highly swollen due to ionization of PAA above its pKa (4.7). Of note, at both pH 3 and 4, the IPN achieved a lower equilibrium water content than PAA alone. This can be explained, in part, by the fact that PEG and PAA complex with each other via hydrogen bonds in an acidic environment, leading to a more compact, less hydrated interpenetrating network structure. At pH above 4.7, the PEG and PAA chains dissociate as the PAA becomes ionized and counterions (along with water) enter the hydrogel to maintain charge neutrality, leading to a high degree of swelling. Nevertheless, the IPNs swell to a slightly lower extent (1.0-1.5%) than the PAA single networks due to the constraint that the PEG network places on PAA swelling. Table 2 also shows that the maximum stress ($\sigma_{max}$), or tensile strength, of the PEG/PAA IPN is nearly an order of magnitude greater in its less-swollen state at pH 3 ($\sigma_{max}$=8.2 MPa) than in its more swollen state at pH 6 ($\sigma_{max}$=0.86 MPa). A similar phenomenon is observed in the PAA network, but the absolute values for $\sigma_{max}$ are 0.38 MPa at pH 3 and 0.05 MPa at pH 6. At every pH, then, the IPN has greater tensile strength than the PAA network, and this difference is intensified at lower pH. In contrast to the differences in the stress-at-break, the trends in the strain-at-break values of the IPN and PAA networks are roughly equivalent, changing from $\epsilon_{break}$ values of ~1.2 at pH 3 to ~0.55 at pH 6. This result confirms the observation made in FIGS. 18A-B, in which the extensibility of the IPN seems to be due to the presence of the PAA network, which has a higher $\epsilon_{break}$ (0.9) than PEG (0.6). The mere presence of the PAA network in the IPN appears to enhance the uniaxial extensibility of the network, a property that enables the IPN hydrogel to be used to support joint loads. In the context of the maximum stress data (Table 2), however, the load-bearing capacity at higher extensions is greater in the presence of hydrogen bonding at low pH than it is in the absence of hydrogen bonding at high pH. In contrast, pH dependence of the initial stiffness moduli ($E_o$) of the IPN and PAA networks is less straightforward. The modulus of the PAA network exhibits a small drop from 0.09 MPa to 0.05 MPa as the pH is increased from 3 to 6. On the other hand, the modulus of the IPN does not decrease at all, but rather increase when the pH is changed from 3 to 6. Of note, the pH-dependence of the IPN does not follow the trend exhibited by the PAA single network, in which the modulus drops by approximately one-half when transitioning from pH 4 to pH 5. This decrease in modulus is correlated with an increase in water content of the PAA single network. In addition, the dependency of water content and subsequently of the hydrogel volume or surface on the pH, enables a (pH) stimulus sensitive hydrogel arthroplasty device that takes advantage of the shrinking or swelling to adapt and secure fixation inside or around a bone as described in a previous section.

To investigate the consequence of relative network moduli even further, the swelling of PAA within the IPNs was maximized. The experimental data shown in Table 2 indicated that the modulus of the IPN was not negatively affected by the increased swelling. The PEG network acts as a constraint on the swelling of PAA in a way that leads to additional interpolymer interactions and a corresponding increase in the IPN modulus. In particular, the increase in the constraining effect of the neutral PEG network on PAA swelling would increase the intensity and number of physical entanglements in the IPN and, in turn, lead to the strain hardening behavior observed in the IPN. To test this hypothesis, the IPNs with first network MW PEG 3400, 4600, and 8000 and constant PAA network conditions were placed in phosphate buffered saline (PBS, pH 7.4, I=0.15) in order to induce maximal swelling under physiologic conditions. Table 2 also shows the equilibrium water content and corresponding swelling ratios for networks prepared from PEG macromonomers with each of these molecular weights, juxtaposed with the water content of the water-swollen and PBS-swollen IPNs. Increasing the size of the first PEG network from 3400 Da to 4600 Da and 8000 Da increases the degree to which the IPN is able to swell. Specifically, while the PEG(3.4 k)/PAA IPN swells to only 70% water when ionized, the PEG(4.6 k)/PAA IPN swells to 77% water and the PEG(8.0 k)/PAA IPN swells to 90% water (nearly the same water content as the PEG(8.0 k) single network) when ionized. Of note, the equilibrium water content values of the PEG(3.4 k) and PEG(4.6 k)-based IPNs do not approach those of their component PEG-DA networks (79.3% and 84.5%, respectively).

The time-dependent water content of the hydrogels was evaluated in terms of the swollen-weight-to-dry-weight ratio. The dry hydrogel was weighed and then immersed in water as well as phosphate buffered saline. At regular intervals, the swollen gels were lifted, patted dry, and weighed until equilibrium was attained. The percentage of equilibrium water content (WC) was calculated from the swollen and dry weights of the hydrogel:

$$WC = \frac{W_s - W_d}{W_s} \times 100$$

where $W_s$ and $W_d$ are the weights of swollen and dry hydrogel, respectively.

FIG. 20 shows the time-dependent swelling behavior of an IPN hydrogel composed of PEG and two different amounts of acrylic acid in the second network (25% and 50%). The single network IPN gels were dried in a desiccator, placed in deionized water, and then weighed at regular time intervals. In both hydrogels, the majority of swelling took place within 5-10 minutes and equilibrium swelling was achieved within 30-40 minutes. The parameters varied to obtain hydrogels with differing water content were the molecular weight of the PEG macronomonomer, the weight fraction of PAA in the second network, as well as the amount of crosslinking agent (e.g. triethylene glycol dimethacrylate, or low molecular weight PEG-DA) added to the first or second networks.

Table 3 shows the effect of varying the concentration of acrylic acid monomer used to prepare the second network on the equilibrium water content of PEG/PAA IPNs in PBS. In general, higher concentrations of acrylic acid monomer leads to hydrogels with lower equilibrium water content and higher stiffness (tensile modulus) and tensile strength for a given set of crosslinking conditions. IPN hydrogels according to the present invention made from these constituents, preferably have an equilibrium water content of between about 15%-95% and more preferably between about 50%-90%.

TABLE 3

Physical properties of PEG(3.4k)/PAA IPNs with varying AA content in PBS

|  | WC (%) | Tensile Modulus | Tensile Strength |
|---|---|---|---|
| PEG(3.4k)/PAA[0.5] | 69% | 3.6 MPa | 4.0 MPa |
| PEG(3.4k)/PAA[0.7] | 65% | 12.0 MPa | 12.0 MPa |
| PEG(3.4k)/PAA[0.8] | 62% | 19.6 MPa | 13 MPa |

Because different MWs of PEG and different starting concentrations of acrylic acid result in different amounts of equilibrium water content, the final amount of PEG and PAA in the hydrogel varies depending on the MW of the starting PEG used and the concentration of acrylic acid used. Examples of compositions of varying weight ratios of PEG and PAA that have been made according to the present invention are shown in Table 4. The compositions in this table were all made using a starting concentration of 50% PEG macromonomers of molecular weight 8000 Da swollen in pure water.

TABLE 4

Compositions of PEG(8.0k)/PAA IPNs with varying preparation concentration of AA monomer

| Concentration of AA in the preparation state | Dry Wt. % PEG in IPN | Dry Wt. % PAA in IPN | (Dry Wt. PEG)/ (Dry Wt. PAA) |
|---|---|---|---|
| 30% | 23.5% | 76.5% | 0.30 |
| 40% | 17.5% | 82.5% | 0.20 |
| 50% | 13.0% | 87.0% | 0.15 |

Swelling of the PAA network within the confines of a more densely crosslinked PEG network (by lowering the MW of the PEG macromonomer) has dramatic consequences on the resulting IPN modulus. Specifically, FIG. 21 shows that the accelerated strain hardening due to elevated pH, as demonstrated in FIG. 18B, is accentuated even further when a PEG network with lower MW (4600 rather than 8000) is used to constrain PAA. These more tightly crosslinked IPNs were placed in phosphate buffered saline to examine them under physiologic conditions (pH 7.4, ionic strength=0.15) where the PAA network is greater than 99% ionized. The PEG(4.6 k)/PAA IPN was first swollen to equilibrium in pure deionized water (pH 5.5, salt-free); it was then switched to the ionizing conditions of phosphate buffered saline (pH 7.4, I=0.15) and again swollen to equilibrium. The increase in the pH to 7.4 and the addition of salt caused the PAA network (but not the PEG network) to swell. The result of this differential swelling within the IPN was a dramatic upward shift in the stress-strain profile that included the initial portion of the curve. In other words, there was an increase in not only the rate of strain hardening, but also in the initial modulus. The strain-hardened PEG/PAA hydrogel therefore demonstrates a compatible set of material properties (stiffness, strength) in physiologic pH, rendering it an appropriate selection for the arthroplasty device.

FIG. 22 shows according to an embodiment of the present invention the stress-strain profiles of PEG(4.6 k)/PAA IPNs prepared with three different combinations of crosslinker chemical end-groups but the same formulations of PEG (MW 4.6 k, 50% by weight in water) and AA (50% v/v in water) as well as the same polymerization conditions (photoinitiator and crosslinker concentration by mole and UV intensity) and swelling conditions (PBS at pH 7.4). Specimen (A) was prepared from PEG-diacrylamide first network and a PAA second network crosslinked with N,N'-(1,2-dihydroxyethylene) bisacrylamide. Specimen (B) was prepared from PEG-diacrylamide first network and a PAA second network crosslinked with triethylene glycol dimethacrylate. Specimen (C) was prepared from PEG-diacrylate first network and a PAA second network crosslinked with triethylene glycol dimethacrylate. These results demonstrated that alternate crosslinking strategies can be employed to create the strain-hardened IPNs based on telechelic macromonomer-based first networks and ionized second networks without deviating from the essence of the present invention.

PEG/PAA IPNs were swollen to equilibrium in a series of PBS solutions of varying ionic strength (0.15 M, 0.30 M, 0.75 M, and 1.5 M) and their equilibrium water content and stress-strain properties were measured. Table 2 shows that the water content of the IPN is reduced with higher salt concentration in the swelling medium, from over 90% at I=0.15 to less then 78% at I=1.5. This is caused by the fact that increased salt in the buffer screens the negative charges on the PAA chains, reducing electrostatic repulsion and, in turn, swelling of the networks.

Ionic strength had a modest effect on the stress-strain properties. Table 2 shows that the stress-strain properties of IPNs in I=0.15 to I=0.75 were roughly equivalent. The IPN swollen in buffer with I=1.5 showed a slight enhancement in fracture stress at higher strains. This result is consistent with the water content data, since the hydrogels with higher solids content (the IPN at higher ionic strength conditions) should have greater mechanical strength. Of note, the final modulus of the IPN in the solution with the highest ionic strength (I=1.5) appeared to be higher than those at lower ionic strength. However, the difference was small and was not found to be statistically significant.

To increase the quantity of topological interactions between the PAA and PEG networks, the polymer content of PAA was varied inside of a PEG(3.4 k) first network. The volume fraction of acrylic acid in solution at the time of the second network polymerization was varied between 0.5 and 0.8 prior to polymerization. After polymerization, the IPNs were swollen to equilibrium in PBS. The resultant hydrogels had different water content, from 62% in the PEG(3.4 k)/PAA [0.8] IPN to 65% in the PEG(3.4 k)/PAA[0.7] IPN and 77% in the PEG(3.4 k)/PAA[0.5] IPN. Of note, the IPNs with increased acrylic acid concentration had lower water content, which in light of the super-absorbency of PAA is a counter-intuitive result. The water content and tensile properties of these IPNs are shown in Table 3. The IPN with the highest PAA content had the highest stress-at-break and modulus, while the one with the lowest PAA content had the lowest stress-at-break and strain-at-break. Notably, the initial modulus values for these samples varied significantly, from 3.6 MPa in the PEG(3.4 k)/PAA[0.5] to 12 MPa in the PEG(3.4 k)/PAA[0.7] IPN and 19.6 MPa in PEG(3.4 k)/PAA[0.8] IPN.

Effect of PAA Content on IPN Swelling in Pure Water

PEG(4600) single networks were prepared and imbibed with varying concentrations of AA in the second network in the presence of the photoinitiator and crosslinker. IPNs based on these AA-swollen PEG networks were then formed by UV-initiated polymerization. The IPNs were then removed from their molds, immersed in deionized water, and allowed to reach equilibrium. The volume of the IPNs relative to the PEG single networks were then measured and compared. The results are plotted in FIG. 19. FIG. 19 shows that the volume of the IPN is increased with increased amount of AA monomer in the second network. This is consistent with the understanding that PAA absorbs water, and therefore increased PAA content in the IPN should lead to increased water absorption. Of note, however, is the fact that the IPN deswells relative to the PEG single network when the AA:EG monomer ratio is less than unity, and swells relative to the PEG network when AA is in excess to EG monomers.

The same PEG/PAA IPNs of varying AA monomer content were tested by uniaxial tensile measurements. The results are shown in FIG. 19. In this figure, both the fracture stress and Young's modulus are plotted as functions of AA mass fraction at the time of polymerization. Young's modulus exhibited a modest monotonic increase as the AA concentration increased. In contrast, the fracture stress exhibited a dramatic increase in magnitude when the AA:EG ratio was increased beyond unity. As the AA monomer concentration increased, however, the fracture stress exhibited a monotonic decline. Finally, the photoinitiator (2-hydroxy-2-methyl propiophenone) and crosslinker (triethylene glycol dimethacrylate) concentrations of the PAA second network were varied during polymerization within PEG(4.6 k) networks and the resulting PEG(4.6 k)/PAA IPNs were studied in terms of their mechanical properties in both pure water and in PBS. The results are shown in Table 5.

TABLE 5

*Effect of crosslinker and photoinitiator concentrations on the mechanical properties of PEG(4.6k)/PAA IPNs

| Sample | Swelling Medium | Crosslinker (vol. %) | Photoinitiator (vol. %) | $E_0$ (MPa) | $\sigma_{max}$ (MPa) | $\epsilon_{max}$ |
|---|---|---|---|---|---|---|
| 1 | dH$_2$O | 0.1 | 1.0 | 1.0 ± 0.1 | 3.9 ± 1.2 | 0.63 ± 0.07 |
| 2 | dH$_2$O | 1.0 | 1.0 | 1.4 ± 0.3 | 9.7 ± 0.4 | 0.91 ± 0.53 |

TABLE 5-continued

*Effect of crosslinker and photoinitiator concentrations on the mechanical properties of PEG(4.6k)/PAA IPNs

| Sample | Swelling Medium | Crosslinker (vol. %) | Photoinitiator (vol. %) | $E_0$ (MPa) | $\sigma_{max}$ (MPa) | $\epsilon_{max}$ |
|---|---|---|---|---|---|---|
| 3 | dH$_2$O | 10.0 | 1.0 | 0.8 ± 0.0 | 5.6 ± 3.7 | 1.07 ± 0.41 |
| 4 | PBS, pH 7.4, I = 0.15 | 0.1 | 1.0 | 5.3 ± 0.3 | 0.5 ± 0.2 | 0.12 ± 0.03 |
| 5 | PBS, pH 7.4, I = 0.15 | 1.0 | 1.0 | 8.4 ± 0.5 | 4.3 ± 0.8 | 0.44 ± 0.03 |
| 6 | PBS, pH 7.4, I = 0.15 | 10.0 | 1.0 | 6.9 ± 0.7 | 1.1 ± 0.2 | 0.20 ± 0.03 |
| 7 | dH$_2$O | 1.0 | 0.1 | 0.9 ± 0.2 | 5.2 ± 2.4 | 1.11 ± 0.08 |
| 8 | dH$_2$O | 1.0 | 1.0 | 1.4 ± 0.3 | 9.7 ± 0.4 | 0.91 ± 0.53 |
| 9 | dH$_2$O | 1.0 | 10.0 | 0.9 ± 0.0 | 4.2 ± 0.0 | 0.67 ± 0.00 |
| 10 | PBS, pH 7.4, I = 0.15 | 1.0 | 0.1 | 8.8 ± 0.0 | 3.3 ± 1.1 | 0.35 ± 0.10 |
| 11 | PBS, pH 7.4, I = 0.15 | 1.0 | 1.0 | 8.4 ± 0.5 | 4.3 ± 0.8 | 0.44 ± 0.03 |
| 12 | PBS, pH 7.4, I = 0.15 | 1.0 | 10.0 | 7.8 ± 0.2 | 1.9 ± 0.6 | 0.34 ± 0.06 |

*Samples 2 & 8 and 5 & 11 provided repeated data to aid visual comparison between experimental conditions To demonstrate that an ionizable monomer is important in the second network, a series of IPNs were prepared under conditions that disrupted the degree of ionizability in the second network. The first method used was copolymerization of the second network with non-ionic monomers. AA monomers in the second network were mixed in three different concentrations relative to the HEA monomers: 10:1, 3:1, and 1:1. Uniaxial tensile testing experiments of the hydrogels swollen in deionized water showed that the PEG/P(AA-co-HEA) IPNs with the highest ratio of AA:HEA in the second network exhibited enhanced mechanical strength. Specifically, changing tensile strength of the IPNs decreased from 9 MPa to 6 MPa and then to 3.5 MPa when the AA:HEA ratio decreased from 10:1 to 3:1 to 1:1, respectively. In other words, IPNs with higher relative HEA content exhibited almost no enhancement in mechanical properties. This result demonstrates that the presence of ionizable carboxyl acid groups in PAA is an important element in the present invention.

In another set of experiments, PEG networks were immersed in AA solutions (containing photoinitiator and crosslinker) that were partially neutralized to pH 5.5 by titration with sodium hydroxide. The monomer-swollen PEG networks were then exposed to UV light to form a partially neutralized PAA network within the PEG network. These "pre-neutralized" PEG/PAA IPNs were then washed in PBS and subjected to uniaxial tensile tests. It was found that neutralizing the AA solution prior to polymerization and then forming the second network leads to an IPN with the same elastic modulus, but with dramatically reduced fracture strength. The stress-at-break is reduced from nearly 4 MPa—in the case of the IPNs prepared under acidic conditions and then neutralized in PBS buffer—to roughly 0.5 MPa. This demonstrates the importance of the fabrication process in creating these strain-hardened IPNs; that is, in the preferred embodiment, ionization and swelling of the second network with buffered, aqueous salt solution should be carried out after the IPN is fully formed.

These results demonstrate that the PEG/PAA IPN system strain-hardens and, in turn, becomes "pre-stressed" with high values for initial stiffness moduli when swollen in buffers of physiologic pH and salt concentrations (e.g. phosphate buffered saline). The strain hardening under these conditions is the result of the constraining effect that the tightly crosslinked, neutral PEG network has on the swelling of the ionized PAA network. This constraining effect leads to additional physical crosslinks between the two networks and manifests as an increase in the initial Young's modulus of the IPN. The tensile modulus values that the hydrogel can attain (12 MPa, but tunable between about 1 to about 20 MPa) exceed those reported in the art. Of note, the hydrogel's modulus (12 MPa) is in the range of values reported for natural healthy human cartilage.

Natural cartilage is, in effect, an avascular "IPN hydrogel" comprised of collagen and negatively charged proteoglycans. By comparison, the IPN hydrogel comprised of PEG and negatively charged PAA. PEG acts as the analog of collagen while PAA acts as the analog of proteoglycans. This fundamental structural similarity of these IPNs to natural cartilage is believed to the reason for their functional similarity: the osmotic pressure created by the polyelectrolyte, coupled with the steric constraint posed by the first network, yields a "pre-stressed" material that, like cartilage, is stiff, yet flexible, and exhibits a highly lubricious surface. To explain the low friction coefficient that cartilage exhibits, a number of scientific approaches have been developed: the fluid-solid stress sharing described by the biphasic theory and the "weeping lubrication" theory are some representative examples. According to these theories, it is important that the material is permeable for low friction to occur; the combination of the permeability coefficient and the equilibrium modulus need to be such so that to allow for the so called "weeping lubrication" but at the same time prevent excessive fluid loss under continuous or repeated dynamic loading. Based on the fact that the strain-hardened IPN has similar permeability, negative charge, water content and stiffness to natural cartilage, we hypothesize that the IPN exhibits a low surface friction coefficient for the same reasons natural cartilage does through any of the aforementioned mechanisms.

We have shown that one of the defining features of the PEG/PAA IPN is its high (compared to state-of-the-art existing hydrogels) tensile stiffness modulus. The tensile stress-strain behavior of the PEG(3400)/PAA(70%) hydrogel material is shown in FIG. 17A from which the elastic tensile modulus is found to be 12 MPa. FIG. 17B presents the confined compression behavior of the above-mentioned hydrogel from which the biphasic constants can be determined. From the time-strain curve, the aggregate equilibrium modulus is found to be Ha=1.56 MPa and the permeability coefficient is K=2.4×10$^{-14}$ m$^4$/N/sec. In a preferred embodiment, the strain-hardened interpenetrating polymer network hydrogel has a permeability coefficient ranging from 1e-18 to 1e-12 m$^4$/Nsec. The hydrogel unconfined compression behavior is presented in FIG. 17C from which the unconfined compressive strength was found to be 18 MPa, with a failure strain under compression of over 80%. The tensile creep behavior of the hydrogel is also depicted in FIG. 17D. Comparison of the set of hydrogel material properties to those of cartilage shows a marked similarity.

Through pin-on-disc tribometer experiments, the wear rates of PEG/PAA hydrogel in PBS and in synovial fluid under physiologic contact stresses were determined; the hydrogel was tested for 3,000,000 cycles at ~1 Hz loading frequency and the linear wear rate was found to be 0.2 μm/million cycles equivalent to about 0.2 μm/year, suggesting that based on the thickness of the bearing region 5 wear life of the device suffices for a lifetime. The material was also tested in a gel-on-cartilage configuration under dynamic physiologic loading conditions. The test was carried out for 150,000 cycles at a sliding frequency of 1 Hz, and a 0.5-1.5 MPa dynamic loading in a synovial fluid and bovine serum solution. Gross observation showed that neither the cartilage nor PEG/PAA showed any macroscopically discernible fibrillation or wear.

Anchoring Specifications

Initial anchoring of the device is made possible by the stretch-to-fit fixation provided by the slight size difference between the hydrogel device and the underlying bone. The polymer cap is placed over the femoral head, creating a snug, compressive fit over the bone. In the case of a concave joint such as the hip socket, a slightly oversized female-type implant creates an expansion fit against the walls of the joint.

Biological anchoring of the device is achieved by means of osteointegration with the inorganic constituents of bone. In the present invention, calcium and phosphate ions are bound to PEG/PAA IPNs through their affinity for the PAA component of the hydrogel as illustrated in FIG. 3. Hydroxyapatite (HAP) is the major inorganic component of bones and teeth comprised of calcium and phosphate ions and is a known promoter of osteoblast growth. In the dental industry, polycarboxylate cements are used to adhere artificial substrates (e.g. dental caps) to enamel. The basis of these cements is electrostatic interaction between the carboxylic acid groups of PAA chains and the calcium phosphate matrix that makes up HAP. Two mechanisms have been proposed, one in which the carboxylic acid groups displace calcium phosphate in HAP and essentially "insert" into the matrix, and the other (which may work synergistically) in which calcium crosslinks HAP and PAA by ion-bridging. In experiments to show that calcium-containing bone constituents can bind to the PEG/PAA IPN, hydroxyapatite (HAP), a known osteoconductive bone mineral, was coated onto the surface PEG/PAA IPNs. A variety of hydroxyapatite particle sizes were able to bind to PEG/PAA. PEG/PAA hydrogels were incubated in 10% w/v aqueous suspensions of HAP in deionized water; this led to visible binding of HAP particles on the surface of the hydrogels. Incubation of the hydrogels in aqueous suspensions of HAP particles of different diameters (ranging from 20 nm to 5 μm), yielded a thick, opaque surface layer on the hydrogels. The samples were then prepared for scanning electron microscopy (SEM) analysis by processing them in graded ethanol solutions. Immersion in ethanol removed the physisorbed, visible layer of HAP. SEM revealed differences in the surface morphology of uncoated hydrogels (FIG. 23a) versus hydroxyapatite-coated hydrogels (FIG. 23b). Energy dispersive x-ray (EDX) spectroscopy (FIG. 23c) revealed the presence of calcium and phosphate on the surface of the hydrogel in a ratio of approximately 1.5-1.6, which is characteristic of hydroxyapatite. SEM coated hydrogel (inset) showed that the HAP (200 nm diameter, shown) was localized to its surface. The biological response to the particles was also studied by seeding osteoblast-like cells (MG-63 cell line) on the hydroxyapatite-coated hydrogels (FIG. 23d). The osteoblast-like cells exhibited evidence of spreading and growth on HAP coatings of 200 nm diameter and higher.

Three different sized particles (20 nm, 200 nm, and 5 μm) of HAP were investigated to determine the effect of particle size on surface coverage on the hydrogel as well on the biological response by osteoblast-like cells. FIG. 24 shows SEM images of the three types of HAP used on both bare silica (Row A) and the PEG/PAA hydrogels, shown in the B (center) and C (bottom) rows at low and high magnification, respectively. These images demonstrate that surface coverage of the hydrogels was inversely related to the particle diameter: the smaller the particle, the more evenly and thoroughly distributed it is on the hydrogel. This surface modification strategy takes advantage of electrostatic interactions between inorganic hydroxyapatite and the negative charge density of PAA. The hydroxyapatite can either be pre-coated on the device prior to implantation in the body, or be coated in vivo as the bone adjacent to the device is remodeled.

Chemical Anchoring

FIGS. 25A-B show according to the present invention an IPN network bonded to bone through a separate polymeric adhesive. A pre-existing IPN hydrogel 10, 11 is placed over bone 3, 4 that is either functionalized with UV-sensitive crosslinkable groups or not treated at all. At the interface between the hydrogel and the bone is a precursor solution of reactive monomers 18 or macromonomers 21. These monomers or macromonomers partially penetrate the matrix of the interpenetrating polymer network. Upon initiation of polymerization, the monomers or macromonomers polymerize and crosslink, yielding an intervening polymer that is bonded to the underlying surface and physically entangled and/or chemically bonded with the hydrogel.

In one example of this anchoring approach, the heterobifunctional crosslinking agent, 3-trimethoxysilylpropylmethacrylate at a concentration of 0.1% w/v in 95% ethanol in deionized water (with pH-adjusted to 4.5) was brushed onto the surface of previously cleaned and dried bovine bone and allowed to dry for 15 minutes and react with the phosphates in the inorganic matrix of the bone. A 25% w/v solution of PEG-dimethacrylate (MW 1000 Da) was then prepared along with 1% v/v 2-hydroxy-2-methyl propiophenone as the photoinitiator and then spread over the bone-interface surface of a PEG/PAA IPN hydrogel. The PEG-dimethacrylate solution was then allowed to diffuse into the IPN hydrogel for 1 hour. Bone was then placed on top of the PEG-dimethacrylate solution on the IPN hydrogel, and then the bone and the hydrogel were clamped together using a binder clip and glass slide (1.0 mm thick) placed on top of the hydrogel to attain even clamping pressure. The specimen was then placed under a UV light source (350 nm) for 45 seconds to cause the PEG-dimethacrylate to cure. The result was a PEG/PAA IPN hydrogel bonded to the bovine bone specimen through a PEG-dimethacrylate adhesive that is interpenetrated within the bone-interface of the IPN (FIG. 25B). Because of the presence of methacrylate groups on the bone through reaction of the trimethoxypropylsilyl methacrylate to the bone, the PEG-dimethacrylate adhesive not only filled in the pores of the bone but also is chemically bonded to the surface. Another example of a "bone-primer" is isocyanatotrimethoxysilane, which after reacting with the inorganic part of bone yields reactive isocyanate groups on the surface, which are available to react with functional groups (such as hydroxyl, amine, or carboxylic acid) on either the bone-interface of the device itself or an adhesive. This method can be used with or without silane functionalization of the underlying bone, as well as with other crosslinkable polymers.

FIG. 26 shows according to the present invention a semi-interpenetrating network in which one of the networks acts as the anchoring intervening polymer. Telechelic macromonomers 13, 15 and second network polymer 11 are mixed together in solution and cast over a bone surface that is pre-coated and/or functionalized with UV-sensitive crosslinkable groups 23. Exposure to an initiating source (e.g. UV light) in the presence of a photoinitiator leads to free-radical polymerization and crosslinking of these crosslinkable groups on both the telechelic macromonomers and the coated/functionalized bone surface. The result of free-radical polymerization and crosslinking is shown on the right. The ends 15 of the telechelic macromonomers have polymerized and have formed physical and/or chemical bonds with the surface of the bone. The linear second network polymers 11 are physically trapped within this first network, forming a second, physically crosslinked network interpenetrating the first chemically crosslinked network 10.

Chemical Surface Modification

An embodiment of the device according to the present invention comprises a bearing region and bone-interfacing region with two different polymeric compositions. In general, this approach leads to a composition gradient within the device as described in FIG. 2. FIG. 27A shows an embodiment of the present invention a fully interpenetrating network in which a third network precursor is partially interpenetrated within the pre-existing IPN by interdiffusion of the monomer for a predetermined time and then polymerized and crosslinked in the presence of the IPN. This yields what is effectively a triple network on one side of the IPN hydrogel that can serve as a bone-interfacing region, which has different properties than the other side containing only two networks. The transition zone between the two sides is determined by the diffusion depth of the third network monomers prior to polymerization of the third network.

FIG. 27B shows another embodiment of the present invention a fully interpenetrating network in which one of the networks is interfacially copolymerized with another polymer that acts as the bone-interfacing material. A pre-existing homopolymer network is swollen with the precursor monomers 14 of a second network. At the bone-interface side of the material is a precursor solution of another reactive monomer 26. These monomers partially penetrate the matrix of the overlying interpenetrating polymer network. Upon exposure to UV, the monomers co-polymerize, yielding a material with a one type of IPN containing 10 and 11 on the bearing side and another type of IPN containing 10 and 27 on the bone-interfacing side. The transition between the two sides is determined by the diffusion depth of the third monomers 26 prior to polymerization of the third network.

Another embodiment of the present invention is to use an external stimulus to create a composition gradient in the second network within the first network of the IPN as illustrated in FIG. 27C. In one example, instead of just acrylic acid monomers for the second network precursor solution, a mixture of ionizable monomer 14 (e.g. acrylic acid) and non-ionic monomers 28 (e.g. acrylamide, N-isopropylacrylamide, or hydroxylethylacrylate monomers) is used. Any combination of ionizable monomer and non-ionizable monomer can be used as comonomers to create the gradient so long as they are capable of copolymerizing with each other. The first network 10 is soaked in a salt solution of ionizable monomer 14, non-ionic monomer 28, crosslinker and photoinitiator (not shown) and then an electric field is applied to the gel (e.g. using electrophoresis equipment). Only the acrylic acid monomers will move along the electric field due to their charge. After formation of an acrylic acid concentration gradient, the gel is exposed to UV and the gradient is fixed via second network gel formation. The result is an IPN hydrogel with a poly(acrylic acid) second network localized to the bearing region and a non-ionic second network (e.g. poly(N-isopropylacrylamide, a temperature-sensitive polymer) localized to the bone-interface region. This is an approach that yields a device that is responsive to both pH and temperature, as described later in FIG. 32.

FIG. 28 shows two embodiments of another device surface modification strategy according to the present invention. This strategy involves the acrylation/methacrylation of an amine-containing or hydroxyl-containing molecule or biomolecule by reaction with a halogenated (active) acid (e.g. acryloyl chloride) (FIG. 28, Reaction A) or with an active ester (e.g. acryloxy-N-hydroxysuccinimide) (FIG. 28, Reaction B) to make it capable of copolymerizing with the precursor of one of the networks in the device. The R-group in these reaction schemes can be any amine-containing or hydroxyl-containing chemical or polymer, proteins, polypeptides, growth factors, amino acids, carbohydrates, lipids, phosphate-containing moieties, hormones, neurotransmitters, or nucleic acids. An example of this process is the reaction of dopamine with acryloyl chloride and subsequent attachment of the conjugated dopamine molecules to the surface of a PEG/PAA hydrogel during the second network formation by the process shown in either FIG. 27B or C. Dopamine hydrochloride (500 mg, 2.6 mmol, 1 eq) was dissolved in methanol (10 mL) and freshly distilled triethylamine (362 µL, 1 eq) was added. Acryloyl chloride (210 µL, 1 eq) was dissolved separately in MeOH and Triethylamine (1.1 mL, 3 eq) was added. The acryloyl chloride solution was then added dropwise to the dopamine solution and the resulting mixture was stirred overnight at room temperature (Reaction A). During the reaction, a colorless precipitate formed that was removed by filtration. Precipitation in diethylether lead to the product, an acrylated dopamine molecule (yield: 85%). In an alternative reaction (Reaction B) to achieve the same result, dopamine hydrochloride (500 mg, 2.6 mmol, 1 eq) was dissolved in methanol (10 mL) and freshly distilled Triethylamine (362 µL, 1 eq) was added. Acrylic acid N-hydroxysuccinimide ester (440 mg, 1 eq) was dissolved separately in methanol and triethylamine (1.1 mL, 3 eq) was added. The acrylic acid N-hydroxysuccinimide ester solution was then added dropwise to the dopamine solution and the resulting mixture was stirred overnight at room temperature. During the reaction a colourless precipitate formed that was removed by filtration. Precipitation in diethylether lead to the product (yield: 75%). The resulting conjugated molecule was then interfacially polymerized with an acrylic acid-based second network in separate experiments (one using the Reaction A conjugate and one using the Reaction B conjugate) as shown in FIG. 27B. A 50% v/v solution of dopamine acrylate containing 1% v/v 2-hydroxy-2-methyl-propiophenone and 1% v/v triethylene glycol dimethacrylate was spread the surface of a preformed PEG-diacrylate network that had been dabbed dry after being swollen overnight in a 50% v/v solution of acrylic acid, 1% 2-hydroxy-2-methyl-propiophenone and 1% triethylene glycol dimethacrylate. After briefly allowing the dopamine-acrylate monomers to mix with the acrylic acid monomers, the swollen gel was placed between glass slides and exposed to UV. The result was an IPN with a PEG/PAA IPN on one side and an IPN of PEG and a dopamine-conjugated polymer network on the other surface. In the transition zone between these was an IPN of PEG and a copolymer of PAA and dopamine-conjugated polymer. This method can be generalized to attain a variety of types of conjugates of the IPN surface.

Another embodiment of the device according to the present invention covalently links molecules or biomolecules to a pre-fabricated device in order to create a bone-interface region with different characteristics than the bearing region. In one such embodiment, any suitable biomolecules may be covalently linked to the IPN hydrogel. In another embodiment, a synthetic polymer is linked to the IPN hydrogel. Preferably, the biomolecules are at least one of proteins, polypeptides, growth factors (e.g. epidermal growth factor) amino acids, carbohydrates, lipids, phosphate-containing moieties, hormones, neurotransmitters, or nucleic acids. Any combination of small molecules or biomolecules can be used, including, but not limited to, drugs, chemicals, proteins, polypeptides, carbohydrates, proteoglycans, glycoproteins, lipids, and nucleic acids. This approach may rely, for example, on (a) photoinitiated attachment of azidobenzamido peptides or proteins, (b) photoinitiated functionalization of hydrogels with an N-hydroxysuccinimide ester, maleimide, pyridyl disulfide, imidoester, active halogen, carbodiimide, hydrazide, or other chemical functional group, followed by reaction with peptides/proteins, or (c) chemoselective reaction of aminooxy peptides with carbonyl-containing polymers. These biomolecules may, for example, promote bone cell adhesion or activity. In one example, a heterobifunctional crosslinker 118 (FIG. 29) with reactive endgroups 115 and 117 joined by a spacer arm 116 is used to modify the IPN hydrogel surfaces 119. One such class of heterobifunctional chemicals are described as azide-active-ester linkers, such as 5-azido-2-nitrobenzoyloxy-N-hydroxysuccinimide ester or its derivatives such as its sulfonated and/or its chain-extended derivatives. However, any coupling strategy can be used to create strain-hardened IPN hydrogels with bioactive surfaces. A detailed example of this embodiment is the attachment of collagen type I to a PEG/PAA IPN surface through the heterobifunctional crosslinker, 5-azido-2-nitrobenzoyloxy-N-hydroxysuccinimide ester, which has a phenyl azide group on one end and a protein-binding N-hydroxysuccinimide group on the other. Substituted phenyl azides have been shown to react with light (250-320 nm, 5 min) to generate aromatic nitrenes, which insert into a variety of covalent bonds. Attachment of the linker to the hydrogel via the phenyl azide group then allows the N-hydroxysuccinimide groups to react with free amines on proteins, and in turn, tether them to the hydrogel surface. The surfaces of the PEG/PAA hydrogels were dabbed dry and then 100 μL of a 0.5% w/v solution of 5-azidonitrobenzoyloxy N-hydroxysuccinimide in dimethylformamide was drop-casted onto the gel and spread evenly over its surface. The solvent was then allowed to evaporate under a fume hood to ensure deposition of the crosslinker onto the hydrogel. The air-dried gel surface was then exposed to UV light for 5 min to react the azide groups to the hydrogel surface. The surface-functionalized gels were then incubated in a 0.3% (w/v) collagen type I solution (Vitrogen) in a 37° C. oven for 16 hours to couple reactive protein amine groups to the N-hydroxysuccinimide moieties on the hydrogel surface. Finally, the gels were washed extensively in PBS to remove organic solvent and unreacted monomers. The presence of tethered protein on the surface was confirmed by X-ray photoelectron spectroscopy, which showed the presence of amide linkages of the surface of the hydrogel, confirming the presence of protein. Table 6 shows quantitative amino acid analysis data showing the presence of collagen on the surface of the gels.

TABLE 6

Results of quantitative amino acid analysis on collagen-tethered PEG/PAA hydrogels (in total micrograms).

| Residue | Reaction 1* | Reaction 2** | Reaction 3*** |
|---------|-------------|--------------|---------------|
| Asx     | 3.18 ± 1.01 | 2.62 ± 0.26  | 2.37 ± 0.39   |
| Thr     | 1.36 ± 0.50 | 1.10 ± 0.10  | 0.97 ± 0.15   |
| Ser     | 1.73 ± 0.55 | 1.40 ± 0.14  | 1.28 ± 0.19   |
| Glx     | 8.56 ± 2.75 | 7.58 ± 0.80  | 6.90 ± 1.13   |
| Pro     | 7.62 ± 2.34 | 6.18 ± 0.74  | 5.64 ± 0.97   |
| Gly     | 11.78 ± 3.06| 9.75 ± 1.10  | 8.92 ± 1.48   |
| Ala     | 4.84 ± 1.47 | 3.96 ± 0.44  | 3.60 ± 0.60   |
| Val     | 1.55 ± 0.50 | 1.09 ± 0.12  | 0.93 ± 0.15   |
| Ile     | 0.90 ± 0.29 | 0.69 ± 0.06  | 0.60 ± 0.10   |
| Leu     | 1.80 ± 0.58 | 1.38 ± 0.14  | 1.17 ± 0.19   |
| Tyr     | 0.18 ± 0.06 | 0.13 ± 0.01  | 0.11 ± 0.01   |
| Phe     | 0.96 ± 0.32 | 0.77 ± 0.09  | 0.70 ± 0.12   |
| His     | 0.52 ± 0.17 | 0.34 ± 0.04  | 0.29 ± 0.05   |
| Lys     | 1.97 ± 0.63 | 1.70 ± 0.17  | 1.57 ± 0.25   |
| Arg     | 4.97 ± 1.62 | 3.89 ± 0.47  | 3.52 ± 0.59   |
| Hy Pro  | 6.80 ± 1.99 | 5.91 ± 0.71  | 5.51 ± 0.96   |
| Hy Lys  | 0.78 ± 0.12 | 0.63 ± 0.06  | 0.55 ± 0.09   |
| Total   | 59.50 ± 17.94 | 49.13 ± 5.46 | 44.63 ± 7.42 |

*Reaction 1 involved incubation of the hydrogels with 0.3% w/v collagen type I
*Reaction 2 involved incubation of the hydrogels with 0.1% w/v collagen type I
*Reaction 3 involved incubation of the hydrogels with 0.03% w/v collagen type I FIG. 30 shows another embodiment of the present invention to attain a different surface chemistry at the bone-interface than that present in the bearing region. This approach involves activating the functional groups on the surface of the hydrogel followed by reaction of these activated functional groups with amine-containing or hydroxyl-containing molecules, macromolecules, or biomolecules. In a preferred embodiment, the carboxylic acid groups on poly(acrylic acid) within an IPN are activated to form an active ester, which subsequently forms acrylamide linkages when reacted with an amine-containing molecule, macromolecule, or biomolecule. In two examples of this strategy, a PEG/PAA IPN hydrogel according to the present invention was surface modified with dopamine functional groups. In Reaction A, the PEG/PAA hydrogel was first washed with ethanol/water mixtures containing increasing amounts of ethanol up to 100 vol. % ethanol. The hydrogel was then soaked in a solution of dicyclohexylcarbodiimide (0.1 M) and Triethylamine (0.2 M) in ethanol for 2 hours. A solution of dopamine hydrochloride (0.1 M) and triethylamine (0.1 M) was prepared and applied onto the surface of the gel. After one hour, the hydrogel was washed with ethanol and then with ethanol/water mixtures containing increasing amounts of water up to 100 vol. % water. The resulting hydrogel had dopamine molecules attached to the hydrogel surface through amide linkages where the carboxylic acids once were. In an alternative to this procedure (FIG. 31, Reaction B), the PEG/PAA hydrogel was soaked in a solution of N-hydroxysuccinimide (15 mM) and N-Ethyl-N-(3-dimethylaminopropyl)carbodiimide (75 mM) in phosphate buffer (10 mM, pH 6) for one hour. After washing with buffer and water, the surface of the gel was exposed to a solution of dopamine hydrochloride in DMF (0.1 M) and triethylamine (0.1 M) for one hour. The hydrogel was then washed with DMF, ethanol and water to remove all excess material to yield the hydrogel with dopamine tethered to its surface. These reactions can be used to tether any molecule, macromolecule, or biomolecule with accessible amine or hydroxyl functional groups to the surface of carboxyl-group containing IPNs. The resulting surface-modification would then be used as the basis of a bone-interface region of the present invention, with the unmodified side serving as the bearing region.

Stimulus-Responsive Hydrogel Arthroplasty Devices

Implantation of the device through volume changes in the device can be achieved by taking advantage of the stimulus-responsiveness of certain polymers. In addition, fabricating the device with different polymer compositions in the bearing and bone-interfacing regions makes offers an additional level of control over the implantation of the device via external stimuli while preserving certain advantageous attributes of a non-responsive polymer or by introducing new attributes to the responsive polymer. Stimuli hereafter refers to a characteristic change in a property that regulates hydrogel volume or shape; this change is caused by maintaining the hydrogel pre-surgically in an environment that is different than the environment inside the body. In an embodiment of the present invention, an external stimulus such as a change in pH, salt concentration, electric field, or temperature causes the device, after A being placed on the bone, to B shrink to conform to the contours of the convex-shaped bone it surrounds, as depicted in FIG. 32. For a concave joint, the device is designed such that the stimulus causes the device to expand against the concavity. Polyelectrolytes are a class of hydrogel polymers that swell/deswell to varying degrees in response to changes in pH, salt concentration, and electric field. Changing pH and salt to control swelling and hydrogel device size would work in the following manner. In one example, the device is pre-swollen in a state where the cap is slightly larger than a convex joint surface, and then after placement on the joint, it would be deswelled by the change after equilibrium in the pH or salt concentration that is present inside the body. The pH/salt concentration can be changed by external means (such as immersing the implant/joint in a bath prior to surgery). Alternatively, it can be implanted and allowed to reach equilibrium swelling in response to the pH and salt concentration of the surrounding body fluids (e.g. synovial fluid). Interpenetrating networks with polyelectrolyte components (e.g. poly(acrylic acid)) such as poly(ethylene glycol)/poly(acrylic acid) networks would be particularly useful in this regard. If this material is preswollen at pH>7.4 and/or salt concentration of less than the osmolarity of the body and is placed loosely over a joint surface, it will, after some time equilibrating in the body, shrink in response to the decrease in pH and/or increase in salt concentration and conform to the contours of the underlying bone. The dimensions of polyelectrolyte-based IPNs can also be modulated by application of an electric field which electrically expands the device. After the electric field is removed, the device shrinks again over the joint. Temperature-sensitive hydrogels such as poly(N-isopropylacrylamide) (NIPAAm) have a lower critical solution temperature that causes them to contract at temperatures higher than about 32° C. This makes possible a scenario where a NIPAAm-based device is placed loosely over a joint at the time of implantation, and after some time in the body, it shrinks to conform to the contours of the bone it surrounds, as depicted in FIG. 32. Thus, using stimuli to alter the hydrogel device size slightly at the time of implantation facilitates its placement without physically stretching it by hand or with a tool, enabling less invasive or arthroscopic approaches for surgical placement.

Variations and Modifications

The interpenetrating polymer networks could have two or more networks or polymeric components (such as linear chains). Examples include but are not limited to a "triple" or even "quadruple" network or a double network interpenetrated with additional polymer chains as discussed in FIGS. 25 and 27. In addition, polymeric tethers (such as poly(ethylene glycol) chains) can be used as intervening spacer arms between the bone-interface region and tethered biomolecules or attached polymer materials.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. An arthroplasty device comprising a bearing region adapted to articulate with another bearing surface and a bone-interfacing region adapted to interact with underlying bone, the bearing region comprising a hydrogel having a first interpenetrating polymer network, the bone-interfacing region comprising another polymer integrated with the first interpenetrating polymer network to form a second interpenetrating polymer network between the hydrogel in the bearing region and the other polymer in the bone-interfacing region, wherein the interpenetrating polymer network hydrogel of the bearing region comprises a first network and a second network, the other polymer in the bone-interfacing region is partially interpenetrated within the first and second networks to form a triple network in the bone-interfacing region.

2. The arthroplasty device of claim 1 wherein the interpenetrating polymer network comprises preformed non-ionic telechelic macromonomers.

3. The arthroplasty device of claim 2 wherein the macromonomer has at least one end group selected from diacrylates, dimethacrylates, diallyl ethers, divinyls, diacrylamides, dimethacrylamides.

4. The arthroplasty device of claim 2 wherein the preformed non-ionic telechelic macromonomers are polyurethane macromonomers.

5. The arthroplasty device of claim 1 wherein the interpenetrating polymer network hydrogel comprises an ionic polymer.

6. The arthroplasty device of claim 5 wherein said ionic polymer comprises carboxylic acid groups.

7. The arthroplasty device of claim 5 wherein said ionic polymer comprises sulfonic acid groups.

8. The arthroplasty device of claim 5 wherein said ionic polymer comprises both carboxylic acid and sulfonic acid functional groups.

9. The arthroplasty device of claim 5 wherein said ionic polymer comprises poly(acrylic acid).

10. The arthroplasty device of claim 1 wherein the interpenetrating polymer network comprises a network of preformed non-ionic telechelic macromonomers physically entangled with the ionic polymer network.

11. The arthroplasty device of claim 1 wherein the bone-interfacing region comprises polyurethane, silicone rubber, or derivatives or combinations thereof.

* * * * *